(12) United States Patent
Gu et al.

(10) Patent No.: US 6,992,069 B2
(45) Date of Patent: Jan. 31, 2006

(54) TRICYCLIC MACROLIDE ANTIBACTERIAL COMPOUNDS

(76) Inventors: Yu-Gui Gu, 1221 Virgina Ave., Libertyville, IL (US) 60048; Zhenkun Ma, 7215 Marquette St., Dallas, TX (US) 75225; Hong Yong, 312 Cambridge Dr., Grayslake, IL (US) 60030

(*) Notice: Subject to any disclaimer, the term of this patent is extended or adjusted under 35 U.S.C. 154(b) by 0 days.

(21) Appl. No.: 10/422,401

(22) Filed: Apr. 24, 2003

(65) Prior Publication Data

US 2004/0029818 A1    Feb. 12, 2004

Related U.S. Application Data

(60) Provisional application No. 60/398,723, filed on Jul. 26, 2002, provisional application No. 60/377,008, filed on Apr. 30, 2002, now abandoned.

(51) Int. Cl.
*A61K 31/70* (2006.01)
*C07H 17/08* (2006.01)

(52) U.S. Cl. .......................... 514/29; 536/7.4
(58) Field of Classification Search ............ 536/7.4; 514/29
See application file for complete search history.

(56) References Cited

U.S. PATENT DOCUMENTS 5,866,549 A   2/1999  Or et al. ............... 579/29

*Primary Examiner*—Elli Peselev
(74) *Attorney, Agent, or Firm*—B. Gregory Donner

(57) ABSTRACT

Antibacterial compounds having formula (I)

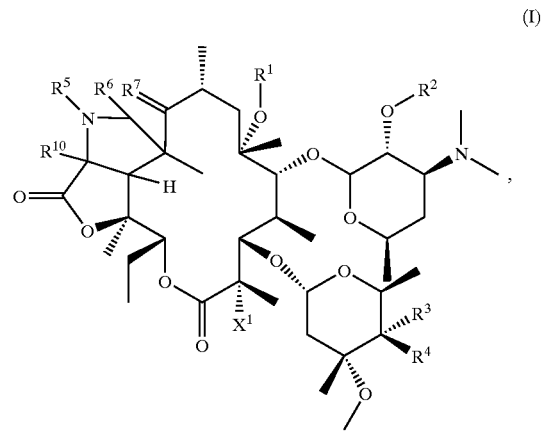

and formula (II),

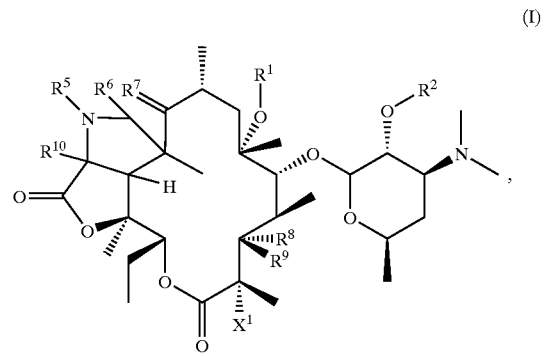

and salts, prodrugs, and salts of prodrugs thereof, processes for making the compounds and intermediates used in the processes, compositions containing the compounds, and methods for prophylaxis or treatment of bacterial infections using the compounds are disclosed.

22 Claims, No Drawings

TRICYCLIC MACROLIDE ANTIBACTERIAL COMPOUNDS

This application claims benefit of co-pending U.S. Provisional Application Ser. No. 60/398,723, filed Jul. 26, 2002, which claims benefit of U.S. Provisional Application Ser. No. 60/377,008, filed Apr. 30, 2002, now abandoned, the specifications of which are hereby incorporated by reference into this application.

FIELD OF THE INVENTION

This invention is directed to compounds which are useful as antibacterials, processes for making the compounds and intermediates used in the processes, compositions containing the compounds, and methods for prophylaxis or treatment of bacterial infections using the compounds.

BACKGROUND OF THE INVENTION

Because the effectiveness of many drugs currently available public use for prophylaxis or treatment of bacterial infections is compromised by the emergence of drug-resistant bacteria, novel antibacterial compounds would be beneficial for their therapeutic value and their contribution to the antibacterial arts.

SUMMARY OF THE INVENTION

A first embodiment of this invention, therefore, is directed to compounds which inhibit bacterial growth, and salts, prodrugs, and salts of prodrugs thereof, the compounds having formula (I)

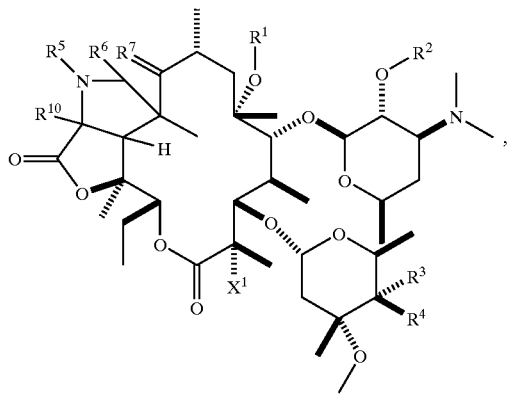

or formula (II),

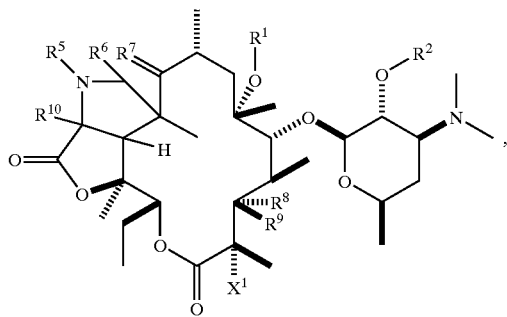

in which $R^1$ is hydrogen, —$R^{11}$, —C(O)O$R^{11}$, —C(O)NH$_2$, —C(O)NH$R^{12}$, —C(O)N$R^{12}R^{13}$, —CH$_2R^{14}$, —C(O)OCH$_2R^{14}$, —C(O)NHCH$_2R^{14}$, or —C(O)N(CH$_2R^{14}$)$_2$;

$R^2$ is hydrogen or $R^P$, in which $R^P$ is a hydroxyl protecting moiety;

one of $R^3$ or $R^4$ is hydrogen and the other is —OH, —O$R^P$, —O$R^{15}$, —OC(O)$R^{15}$, —OC(O)O$R^{15}$, —OC(O)NH$_2$, —OC(O)NH$R^{16}$, —OC(O)N$R^{16}R^{17}$, —OCH$_2R^{18}$, or —OC(O)OCH$_2R^{18}$; or $R^3$ and $R^4$ together are =O or —CH$_2$O—;

$R^5$ is hydrogen, —$R^{19}$, —C(O)O$R^{19}$, —C(O)NH$_2$, —C(O)NH$R^{20}$, —C(O)N$R^{20}R^{21}$, —CH$_2R^{22}$, —C(O)OCH$_2R^{22}$, —C(O)NHCH$_2R^{22}$, or —OC(O)N(CH$_2R^{22}$)$_2$;

$R^6$ and $R^{10}$ are independently hydrogen or —$R^{23}$;

$R^7$ is =O, =NOH, =NO$R^P$, =NO$R^{24}$, or =NO(CH$_2$)$R^{25}$;

one of $R^8$ and $R^9$ is hydrogen, and the other is —OH or —O$R^{32}$; or $R^8$ and $R^9$ together are =O;

$R^{11}$, $R^{15}$, $R^{19}$, $R^{24}$, and $R^{26}$ are independently alkyl, —(CH$_2$)alkenyl, —(CH$_2$)alkynyl, alkyl substituted with one or two or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

$R^{12}$, $R^{13}$, $R^{16}$, $R^{17}$, $R^{20}$, $R^{21}$, $R^{27}$, and $R^{28}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NH$R^{30}$, and —N$R^{30}R^{31}$, —(CH$_2$)alkenyl substituted with one substituent selected from the group consisting of cycloalkyl, aryl, heteroaryl, heterocyclyl, —NH$_2$, —NH$R^{30}$, and —N$R^{30}R^{31}$, or —(CH$_2$)alkynyl substituted with one substituent selected from the group consisting of cycloalkyl, aryl, heteroaryl, heterocyclyl, —NH$_2$, —NH$R^{30}$, and —N$R^{30}R^{31}$; or $R^{12}$ and $R^{13}$ together, $R^{16}$ and $R^{17}$ together, $R^{20}$ and $R^{21}$ together, or $R^{27}$ and $R^{28}$ together are independently $C_3$–$C_6$-alkylene, $C_5$–$C_6$-alkylene interrupted with one moiety selected from the group consisting of —O—, —NH—, —N(alkyl)-, —S—, —S(O)—, and —SO$_2$—, $C_3$–$C_6$-alkylene substituted with one substituent selected from the group consisting of —OH, —O(alkyl), =O, —NH$_2$, —NH$R^{30}$, and —N$R^{30}R^{31}$, or $C_5$–$C_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH$R^{30}$, and —N$R^{30}R^{31}$;

$R^{14}$, $R^{18}$, $R^{22}$, $R^{25}$, and $R^{29}$ are independently alkyl interrupted with one or two or three moieties independently selected from the group consisting of —O—, —NH—, —N(alkyl)-, —S—, —S(O)—, and —SO$_2$— or alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NH$R^{30}$, and —N$R^{30}R^{31}$;

$R^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one or two or three substituents independently selected from the group consisting of cycloalkyl, aryl, heteroaryl, and heterocyclyl, alkyl interrupted with one or two or three moieties independently selected from the group consisting of —O—, —NH—, —N(alkyl)-, —S—, —S(O)—, and —SO$_2$—, alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkenyl interrupted with one or two moieties independently selected from the group consisting of —O—, —NH—, —N(alkyl)-, —S—, —S(O)—, and —SO$_2$—, alkenyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkynyl interrupted with one or two moieties independently selected from the group consisting of —O—, —NH—, —N(alkyl)-, —S—, —S(O)—, and —SO$_2$—, or alkynyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

$R^{30}$ and $R^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; or $R^{30}$ and $R^{31}$ together are C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NH(alkyl), and —N(alkyl)$_2$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$;

$R^{32}$ is —R$^{26}$, —C(O)OR$^{26}$, —C(O)NH$_2$, —C(O)NHR$^{27}$, —C(O)NR$^{27}$R$^{28}$, —CH$_2$R$^{29}$, —C(O)OCH$_2$R$^{29}$, —C(O)NHCH$_2$R$^{29}$, or —C(O)N(CH$_2$R$^{29}$)$_2$; and $X^1$ is hydrogen or fluoride.

A second embodiment of this invention is directed to a process for making the compounds having formula (I)-b,

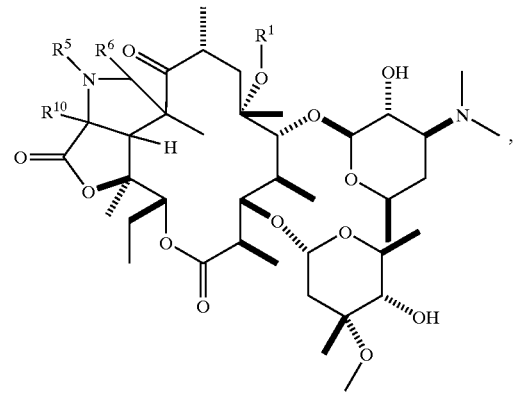

or formula (II)-f,

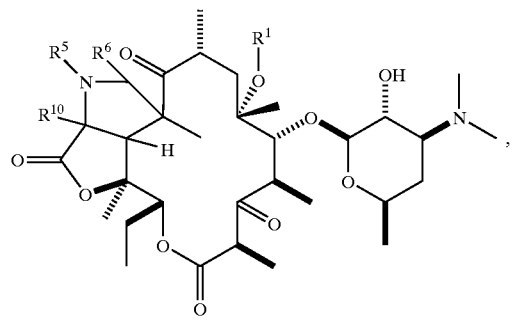

and salts, prodrugs, or salts of prodrugs thereof, in which $R^1$ is hydrogen, —R$^{11}$, —C(O)OR$^{11}$, —C(O)NH$_2$, —C(O)NHR$^{12}$, —C(O)NR$^{12}$R$^{13}$, —CH$_2$R$^{14}$, —C(O)OCH$_2$R$^{14}$, —C(O)NHCH$_2$R$^{14}$, or —C(O)N(CH$_2$R$^{14}$)$_2$;

$R^5$ is hydrogen, —R$^{19}$, —C(O)OR$^{19}$, —C(O)NH$_2$, —C(O)NHR$^{20}$, —C(O)NR$^{20}$R$^{21}$, —CH$_2$R$^{22}$, —C(O)OCH$_2$R$^{22}$, —C(O)NHCH$_2$R$^{22}$, or —CH$_2$R$^{22}$;

$R^6$ and $R^{10}$ are independently hydrogen or —R$^{23}$;

$R^{11}$ and $R^{19}$ are independently alkyl, —(CH$_2$)alkenyl, —(CH$_2$)alkynyl, alkyl substituted with one, two, or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

$R^{12}$, $R^{13}$, $R^{20}$, and $R^{21}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR$^{30}$, and —NR$^{30}$R$^{31}$, —(CH$_2$)alkenyl substituted with one substituent selected from the group consisting of cycloalkyl, aryl, heteroaryl, heterocyclyl, —NH$_2$, —NHR$^{30}$, and —NR$^{30}$R$^{31}$, or —(CH$_2$)alkynyl substituted with one substituent selected from the group consisting of cycloalkyl, aryl, heteroaryl, heterocyclyl, —NH$_2$, —NHR$^{30}$, and —NR$^{30}$R$^{31}$, or $R^{12}$ and $R^{13}$ together, or $R^{20}$ and $R^{21}$ together are $C_3$–$C_6$-alkylene, $C_5$–$C_6$-alkylene interrupted with one moiety selected from the group consisting of —O—, —NH—, —N(alkyl)-, —S—, —S(O)—, and —SO$_2$—, $C_3$–$C_6$-alkylene substituted with one substituent selected from the group consisting of —OH, —O(alkyl), =O, —NH$_2$, —NHR$^{30}$, and —NR$^{30}$R$^{31}$, or $C_5$–$C_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NHR$^{30}$, and —NR$^{30}$R$^{31}$;

$R^{14}$ and $R^{22}$ are independently alkyl interrupted with one or two or three moieties independently selected from the group consisting of —O—, —NH—, —N(alkyl)-, —S—, —S(O)—, and —SO$_2$— or alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

$R^{23}$ is alkyl, alkenyl, alkynyl, aryl, heteroaryl, heterocyclyl, alkyl substituted with one, two, or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one, two, or three substituents independently selected from the group consisting of cycloalkyl, aryl, heteroaryl, and heterocyclyl, alkyl interrupted with one or two or three moieties independently selected from the group consisting of —O—, —NH—, —N(alkyl)-, —S—, —S(O)—, and —SO$_2$—, alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkenyl interrupted with one or two moieties independently selected from the group consisting of —O—, —NH—, —N(alkyl)-, —S—, —S(O)—, and —SO$_2$—, alkenyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkynyl interrupted with one or two moieties independently selected from the group consisting of —O—, —NH—, —N(alkyl)-, —S—, —S(O)—, and —SO$_2$—, or alkynyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$; and $R^{30}$ and $R^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; or $R^{30}$ and $R^{31}$ together are $C_3$–$C_6$-alkylene, $C_5$–$C_6$-alkylene interrupted with one moiety selected from the group consisting of —O—, —NH—, —N(alkyl)-, —S—, —S(O)—, and —SO$_2$—, $C_3$–$C_6$-alkylene substituted with one substituent selected from the group consisting of —OH, —O(alkyl), =O, —NH$_2$, —NH(alkyl), and —N(alkyl)$_2$, or $C_5$–$C_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$;

the process comprising the steps of:
(a) reacting a compound having formula (X)

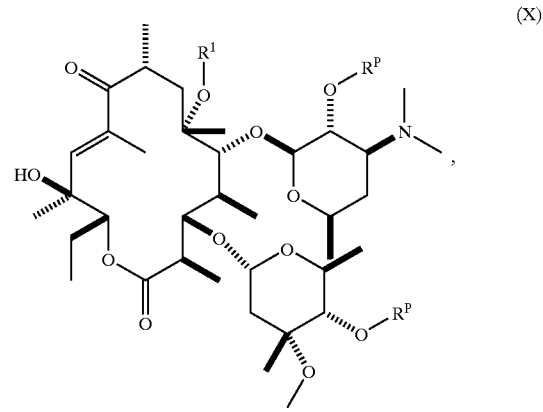

(X)

or a compound having formula (IX)

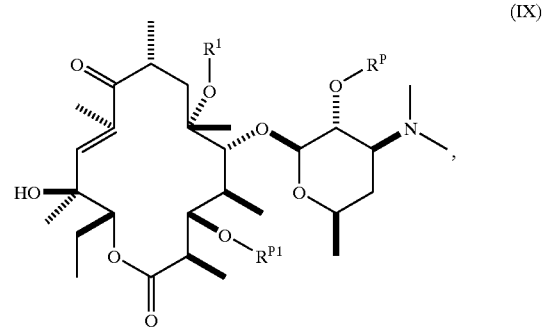

(IX)

in which $R^P$ is a hydroxyl protecting moiety and $R^{P1}$ is trimethylsilyl or triethylsilyl, a compound having formula $(X^2CHR^{10}CO)_2O$,
   in which $X^2$ is —Cl or —Br,
and a second base, with or without 4-(N,N-dimethylamino)pyridine, to provide a compound having formula (XI)

(XI)

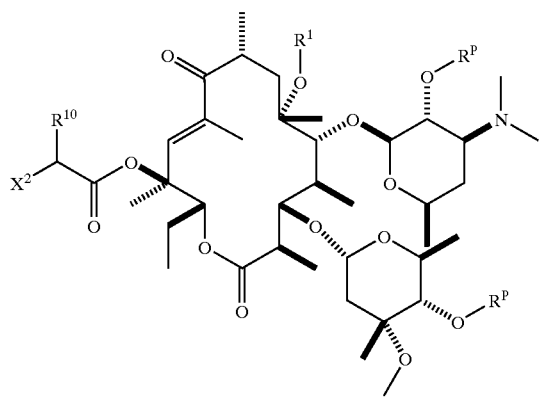

or a compound having formula (XIII)

(XIII)

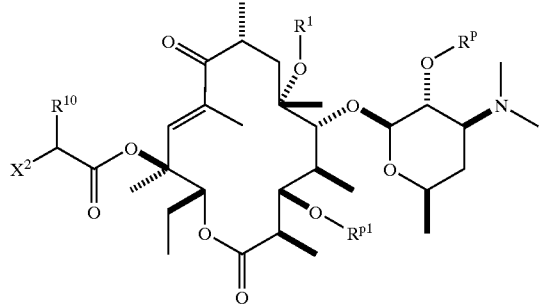

respectively;

(b) reacting the product of step (a) and a compound having formula $R^5NH_2$ to provide a compound having formula (XII)

(XII)

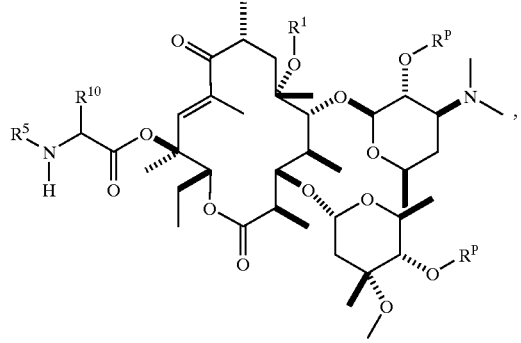

or a compound having formula (XIV)

(XIV)

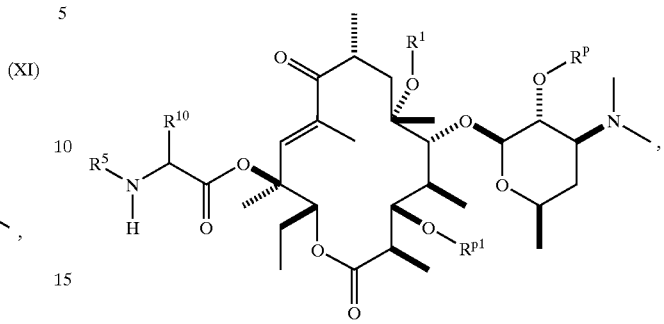

respectively;

(c) reacting the product of step (b), a compound having formula $R^6CHO$, and a first acid, between about 75° C. and about 120° C., to provide a compound having formula (I)-a (I)-a

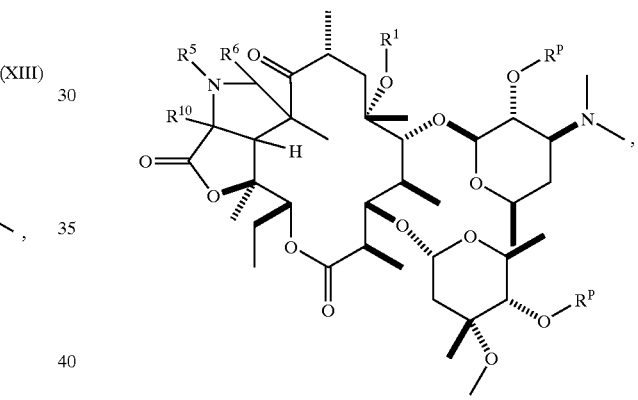

or a compound having formula (XV)

(XV)

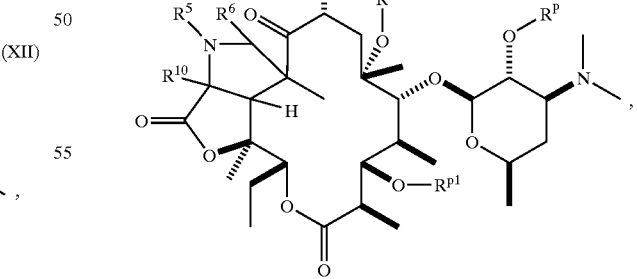

respectively;

(d) reacting the compound having formula (XV) and a fluorinating agent and reacting the product obtained therefrom and an oxidant, with or without a second base, to provide a compound having formula (II)-c

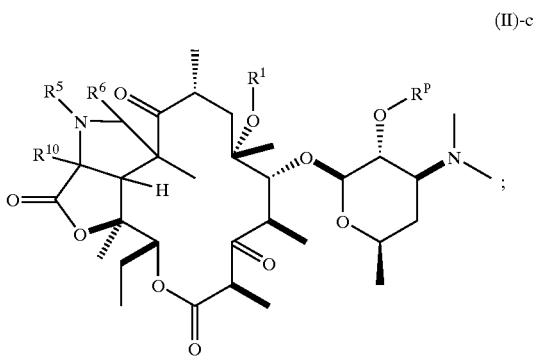

(II)-c and (e)-(1) reacting the compound having formula (I)-a and a deprotecting agent, or (e)-(2) reacting the compound having formula (II)-c and a deprotecting agent.

A third embodiment of this invention is directed to a process for making compounds having formula (II)-g

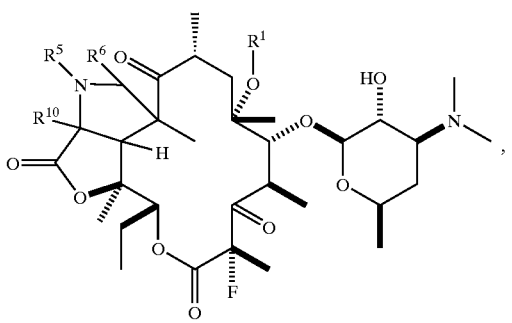

(II)-g or salts, prodrugs, or salts of prodrugs thereof, in which $R^1$ is hydrogen, —$R^{11}$, —C(O)O$R^{11}$, —C(O)NH$_2$, —C(O)NH$R^{12}$, —C(O)N$R^{12}R^{13}$, —CH$_2R^{14}$, —C(O)OCH$_2R^{14}$, —C(O)NHCH$_2R^{14}$, or —C(O)N(CH$_2R^{14}$)$_2$;

$R^5$ is hydrogen, —$R^{19}$, —C(O)O$R^{19}$, —C(O)NH$_2$, —C(O)NH$R^{20}$, —C(O)N$R^{20}R^{21}$, —CH$_2R^{22}$, —C(O)OCH$_2R^{22}$, —C(O)NHCH$_2R^{22}$, or —OC(O)N(CH$_2R^{22}$)$_2$;

$R^6$ and $R^{10}$ are independently hydrogen or —$R^{23}$;

$R^{11}$ and $R^{19}$ are independently alkyl, —(CH$_2$)alkenyl, —(CH$_2$)alkynyl, alkyl substituted with one, two, or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

$R^{12}$, $R^{13}$, $R^{20}$, and $R^{21}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR$^{30}$, and —NR$^{30}R^{31}$, —(CH$_2$)alkenyl substituted with one substituent selected from the group consisting of cycloalkyl, aryl, heteroaryl, heterocyclyl, —NH$_2$, —NHR$^{30}$, and —NR$^{30}R^{31}$, or —(CH$_2$)alkynyl substituted with one substituent selected from the group consisting of cycloalkyl, aryl, heteroaryl, heterocyclyl, —NH$_2$, —NHR$^{30}$, and —NR$^{30}R^{31}$; or $R^{12}$ and $R^{13}$ together, or $R^{20}$ and $R^{21}$ together are $C_3$–$C_6$-alkylene, $C_5$–$C_6$-alkylene interrupted with one moiety selected from the group consisting of —O—, —NH—, —N(alkyl)-, —S—, —S(O)—, and —SO$_2$—, $C_3$–$C_6$-alkylene substituted with one substituent selected from the group consisting of —OH, —O(alkyl), =O, —NH$_2$, —NHR$^{30}$, and —NR$^{30}R^{31}$, or $C_5$–$C_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NHR$^{30}$, and —NR$^{30}R^{31}$;

$R^{14}$ and $R^{22}$ are independently alkyl interrupted with one or two or three moieties independently selected from the group consisting of —O—, —NH—, —N(alkyl)-, —S—, —S(O)—, and —SO$_2$— or alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}R^{31}$;

$R^{23}$ is alkyl, alkenyl, alkynyl, aryl, heteroaryl, heterocyclyl, alkyl substituted with one, two, or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one, two, or three substituents independently selected from the group consisting of cycloalkyl, aryl, heteroaryl, and heterocyclyl, alkyl interrupted with one or two or three moieties independently selected from the group consisting of —O—, —NH—, —N(alkyl)-, —S—, —S(O)—, and —SO$_2$—, alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}R^{31}$, alkenyl interrupted with one or two moieties independently selected from the group consisting of —O—, —NH—, —N(alkyl)-, —S—, —S(O)—, and —SO$_2$—, alkenyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}R^{31}$, alkynyl interrupted with one or two moieties independently selected from the group consisting of —O—, —NH—, —N(alkyl)-, —S—, —S(O)—, and —SO$_2$—, or alkynyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$; and R$^{30}$ and R$^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; or R$^{30}$ and R$^{31}$ together are C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NH(alkyl), and —N(alkyl)$_2$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$;

the process comprising the steps of:

(a) reacting a compound having formula (II)-c

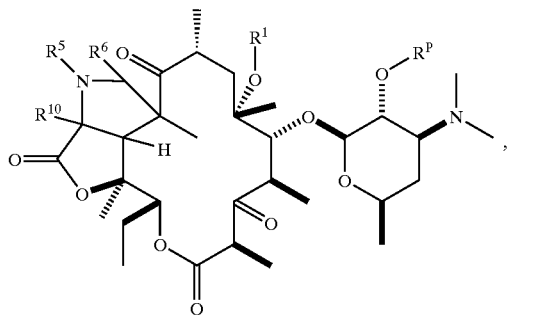

(II)-c in which R$^P$ is a hydroxyl protecting moiety, and a fluorinating agent, with or without a fourth base; and (b) reacting the product of step (a) and deprotecting agent.

A fourth embodiment of this invention is directed to compounds employed in the second embodiment, the compounds having formula (XI)

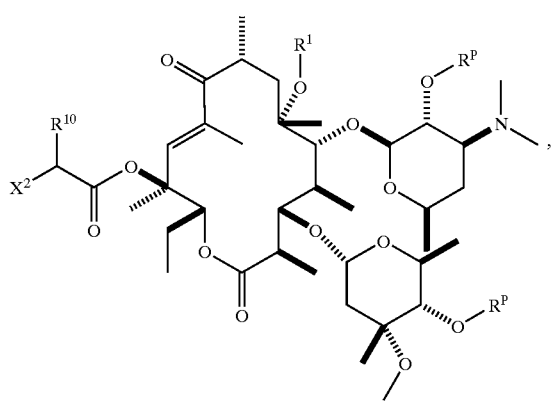

(XI)

formula (XII),

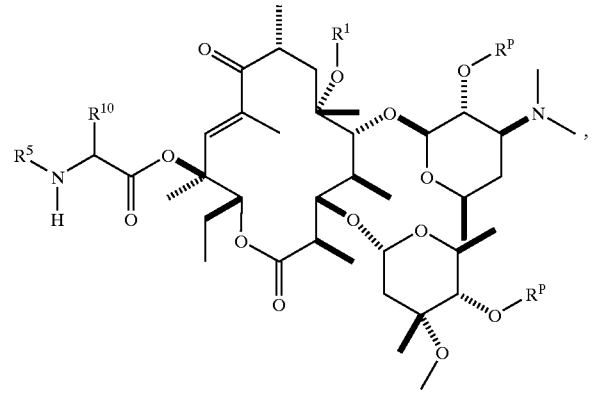

(XII)

formula (XIII),

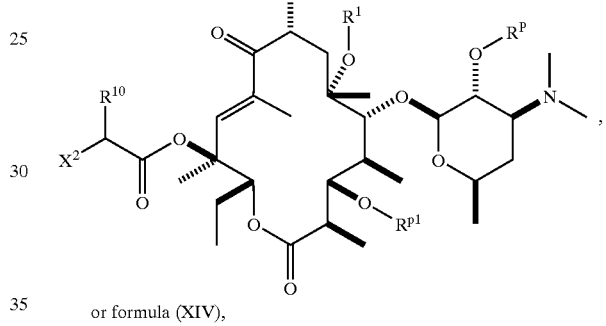

(XIII)

or formula (XIV),

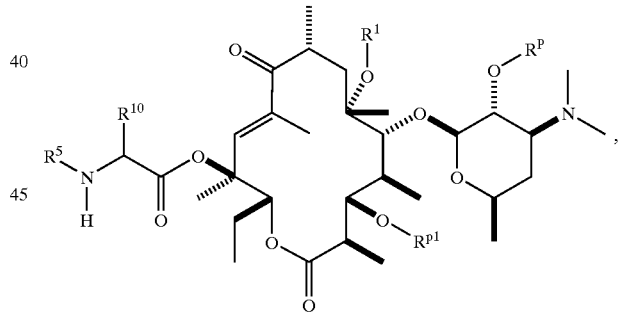

(XIV)

and salts thereof, in which

R$^1$ is hydrogen, —R$^{11}$, —C(O)OR$^{11}$, —C(O)NH$_2$, —C(O)NHR$^{12}$, —C(O)NR$^{12}$R$^{13}$, —CH$_2$R$^{14}$, —C(O)OCH$_2$R$^{14}$, —C(O)NHCH$_2$R$^{14}$, or —C(O)N(CH$_2$R$^{14}$)$_2$;

R$^5$ is hydrogen, —R$^{19}$, —C(O)OR$^{19}$, —C(O)NH$_2$, —C(O)NHR$^{20}$, —C(O)NR$^{20}$R$^{21}$, —CH$_2$R$^{22}$, —C(O)OCH$_2$R$^{22}$, —C(O)NHCH$_2$R$^{22}$, or —OC(O)N(CH$_2$R$^{22}$)$_2$;

R$^{10}$ is hydrogen or —R$^{23}$;

R$^{11}$ and R$^{19}$ are independently alkyl, —(CH$_2$)alkenyl, —(CH$_2$)alkynyl, alkyl substituted with one or two or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

$R^{12}$, $R^{13}$, $R^{20}$, and $R^{21}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR$^{30}$, and —NR$^{30}$R$^{31}$, —(CH$_2$)alkenyl substituted with one substituent selected from the group consisting of cycloalkyl, aryl, heteroaryl, heterocyclyl, —NH$_2$, —NHR$^{30}$, and —NR$^{30}$R$^{31}$, or —(CH$_2$)alkynyl substituted with one substituent selected from the group consisting of cycloalkyl, aryl, heteroaryl, heterocyclyl, —NH$_2$, —NHR$^{30}$, and —NR$^{30}$R$^{31}$; or $R^{12}$ and $R^{13}$ together, or $R^{20}$ and $R^{21}$ together are independently C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NHR$^{30}$, and —NR$^{30}$R$^{31}$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NHR$^{30}$, and —NR$^{30}$R$^{31}$;

$R^{14}$ and $R^{22}$ are independently alkyl interrupted with one or two or three moieties independently selected from the group consisting of —O—, —NH—, —N(alkyl)-, —S—, —S(O)—, and —SO$_2$— or alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

$R^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one or two or three substituents independently selected from the group consisting of cycloalkyl, aryl, heteroaryl, and heterocyclyl, alkyl interrupted with one or two or three moieties independently selected from the group consisting of —O—, —NH—, —N(alkyl)-, —S—, —S(O)—, and —SO$_2$—, alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$; alkenyl interrupted with one or two moieties independently selected from the group consisting of —O—, —NH—, —N(alkyl)-, —S—, —S(O)—, and —SO$_2$—, alkenyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkynyl interrupted with one or two moieties independently selected from the group consisting of —O—, —NH—, —N(alkyl)-, —S—, —S(O)—, and —SO$_2$—, or alkynyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

$R^{30}$ and $R^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; or $R^{30}$ and $R^{31}$ together are C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NH(alkyl), and —N(alkyl)$_2$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$;

$R^P$ is (methyl)carbonyl or (phenyl)carbonyl;

$R^{P1}$ is trimethylsilyl or triethylsilyl; and $X^2$ is chloride or bromide.

A fifth embodiment of this invention is directed to compositions which are useful for prophylaxis or treatment of bacterial infections in a fish or a mammal comprising a therapeutically effective amount of one or more of the compounds of the first embodiment and an excipient.

A sixth embodiment of this invention is directed to methods for prophylaxis or treatment of bacterial infections in a fish or a mammal comprising administering to the fish or the mammal a therapeutically effective amount of one or more of the compounds of the first embodiment.

DETAILED DESCRIPTION OF THE INVENTION

Compounds of this invention, also referred to as "the compounds," comprise both fixed and variable moieties, which variable moieties are identified by a capital letter and accompanying numerical and/or alphabetical superscript, and for which the following terms have the meanings indicated.

"Alkenyl" means monovalent, straight-chain and branched-chain hydrocarbon moieties, having two to eight carbon atoms and at least one carbon-carbon double bond, attached through a carbon atom.

Examples of alkenyl moieties include but-1,3-dienyl, butenyl, but-2-enyl, ethenyl, 1-ethylhexen-2-yl, hex-3-enyl, 1-methylbutenyl, 2-methylbutenyl, 1-methylbut-2-enyl, 1-methylbut-1,3-dienyl, pentenyl, pent-2-enyl, pent-3-enyl, and propenyl.

"Alkyl" means monovalent, saturated, straight-chain and branched-chain hydrocarbon moieties, having one to six carbon atoms, attached through a carbon atom.

Examples of alkyl moieties include butyl, 1,1,-dimethylethyl, 1,1-dimethylpropyl, 1,2-dimethylpropyl, ethyl, 1-ethylpropyl, 2-ethylpropyl, hexyl, methyl, 2-methylpropyl, 3-methylbutyl, 1-methylpentyl, 2-methylpent-3-yl, and pentyl.

"Alkylene" means divalent, saturated, straight-chain and branched-chain hydrocarbon moieties, having one to eight carbon atoms, attached through carbon atoms.

Examples of alkylene moieties include butylene, 1,1,-dimethylethylene, 1,1-dimethylpropylene, 1,2-dimethylpropylene, ethylene, 1-ethylpropylene, 2-ethylpropylene, hexylene, methylene, 2-methylpropylene, 3-methylbutylene, 1-methylpentylene, 2-methyl-2-ethylpropylene, and pentylene.

"Alkynyl" means monovalent, straight-chain and branched-chain hydrocarbon moieties, having two to six carbon atoms and at least one carbon-carbon triple bond, attached through a carbon atom.

Examples of alkynyl moieties include ethynyl (acetylenyl), pentynyl, pent-2-ynyl, pent-3-ynyl, pent-4-ynyl, 1-methylbut-2-ynyl, 2-methylbut-3-ynyl, hexynyl, hex-2-ynyl, hex-3-ynyl, hex-4-ynyl, 1-methyl-pent-2-ynyl, 1-methyl-enepent-3-ynyl, 1-methyl-pent-2,4-diynyl, and prop-2-ynyl (propargyl).

"Aryl" means monovalent, unsubstituted and substituted phenyl moieties, attached through a carbon atom and unfused or fused with another phenyl moiety or a cycloalkyl, cycloalkenyl, heteroaryl, heterocyclyl, naphthyl, or saturated part of an indanyl moiety.

Examples of phenyl moieties fused with phenyl, naphthyl, or the saturated part of an indanyl moieties are unsubstituted and substituted naphth-(1- or 2- or 3- or 4-) yl, anthracen-(1- or 2- or 3- or 4-)yl, and fluoren-(1- or 2- or 3- or 4-)yl, respectively.

Examples of phenyl moieties fused with cycloalkyl moieties are unsubstituted and substituted indan-(4- or 5- or 6- or 7-)yl and 1,2,3,4-tetrahydronaphth-(5- or 6- or 7- or 8-)yl.

Examples of phenyl moieties fused with cycloalkenyl moieties are unsubstituted and substituted inden-(4- or 5- or 6- or 7-)yl, 1,2-dihydronaphth-(5- or 6- or 7- or 8-)yl and 1,2-dihydronaphth-(5- or 6- or 7- or 8-)yl.

Examples of phenyl moieties fused with heteroaryl moieties include unsubstituted and substituted benzimidazol-(4- or 5- or 6- or 7-)yl, 1-benzofuran-(4- or 5- or 6- or 7-yl, 1,2-benzisothiazol-(4- or 5- or 6- or 7-yl, benzthiazol-(4- or 5- or 6- or 7-)yl, 1-benzothiophen-(4- or 5- or 6- or 7-)yl, cinnolin-(5- or 6- or 7- or 8-)yl, indol-(4- or 5- or 6- or 7-)yl, isoquinolin-(5- to 8-)yl, phthalazin-(5- to 8-)yl, quinazolin-(5- to 8-)yl, quinolin-(5- or 6- or 7- or 8-)yl, and quinoxalin-(5- or 6- or 7- or 8-)yl.

Examples of phenyl moieties fused with heterocyclyl moieties include unsubstituted and substituted 1,3-benzodiox-(4- or 5- or 6- or 7-)yl, 1,4-benzodiox-(5- or 6- or 7- or 8-)yl, 1,3-dihydro-2-benzofuran-(4- or 5- or 6- or 7-)yl, 2,3-dihydro-1-benzofuran-(4- or 5- or 6- or 7-)yl, 1,3-dihydro-2-benzothiophen-(4- or 5- or 6- or 7-)yl, 2,3-dihydro-1-benzothiophen-(4- or 5- or 6- or 7-)yl, and indolin-(4- or 5- or 6- or 7-)yl.

"Cycloalkyl" means monovalent, unsubstituted and substituted, saturated cyclic hydrocarbon moieties, having three to six carbon atoms, attached through a carbon atom.

Examples of cycloalkyl moieties are unsubstituted and substituted cyclopropyl, cyclobutyl, cyclopentyl, and cyclohexyl.

"Cycloalkenyl" means means monovalent, unsubstituted and substituted, cyclic hydrocarbon moieties having four to six carbon atoms and at least one carbon-carbon double bond, attached through a carbon atom.

Examples of cycloalkenyl moieties are unsubstituted and substituted 1,3-cyclohexadienyl, 1,4-cyclohexadienyl, cyclohexenyl, cyclopentadienyl, and cyclopentenyl.

"Halo" means fluoro (—F), chloro (—Cl), bromo (—Br), and iodo (—I) moieties.

"Heteroaryl" means (1) monovalent, aromatic, unsubstituted and substituted five-membered ring moieties having two double bonds and (a) one oxygen or one sulfur atom, (b) one, two, three, or four nitrogen atoms, or (c) one or two nitrogen atoms and one oxygen or one sulfur atom, in which, for (a), (b) and (c), the remaining atoms are carbon atoms and the rings themselves may be attached through a carbon atom or a nitrogen atom; and (2) monovalent six-membered ring moieties having three double bonds and one or two or three nitrogen atoms and the remaining atoms are carbon atoms, and the rings themselves are attached through a carbon atom; in which the heteroaryl moieties (1) and (2) are unfused or fused with another heteroaryl moiety or an aryl moiety.

Examples of five-membered heteroaryl moieties are unsubstituted and substituted furanyl, imidazolyl, isothiazolyl, isoxazolyl, 1,2,3-oxadiazolyl, oxazolyl, pyrazolyl, pyrrolyl, tetrazolyl, 1,3,4-thiadiazolyl, thiazolyl, thiophenyl (thienyl), 1H-tetrazolyl, 2H-tetraäzolyl, and 1,2,3-triazolyl.

Examples of five-membered heteroaryl moieties fused with aryl moieties include unsubstituted and substituted benzimidazol-(1- or 2-)yl, 1-benzofuran-(2- or 3-)yl, 1,2-benzisothiazol-3-yl, benzthiazol-2-yl, 1-benzothiophen-(2- or 3-)yl, cinnolin-(3- or 4-)yl, indol-(1- or 2- or 3-)yl, isoquinolin-(1- or 3- or 4-)yl, phthalazin-(1- or 4-)yl, quinazolin-(2- or 4-)yl, quinolin-(2- or 3- or 4-)yl, and quinoxalin-(2- or 3-)yl.

Examples of five-membered heteroaryl moieties fused with other five-membered heteroaryl moieties include unsubstituted and substituted (1,3)thiazolo(4,5-d) (1,3)oxazolyl, (1,3)thiazolo(4,5-d) (1,3)thiazolyl, thieno(3,2-d) (1,3)oxazolyl, thieno(3,2-d) (1,3)thiazolyl, and thieno(2,3-b)thiophenyl.

Examples of five-membered heteroaryl moieties fused with six-membered heteroaryl moieties include unsubstituted and substituted furo(2,3-b)pyridin-(2- or 3-)yl, 3H-imidazo(4,5-b)pyridin-(2- or 3-)yl, (1,3)thiazolo(4,5-b)pyrazin-2-yl, (1,3)thiazolo(4,5-b)pyridin-2-yl, and thieno(2,3-b)pyridin-(2- or 3-)yl.

Examples of six-membered heteroaryl moieties are unsubstituted and substituted pyrazinyl, pyridazinyl, pyridyl, pyrimidinyl, and 1,3,5-triazinyl.

Six-membered heteroaryl moieties fused with aryl moieties include unsubstituted and substituted cinnolin-(3- or 4-)yl, isoquinolin-(1- or 3- or 4-)yl, phthalazin-(1- or 4-)yl, quinazolin-(2- or 4-)yl, quinolin-(2- or 3- or 4-)yl, and quinoxalin-(2- or 3-)yl.

Six-membered heteroaryl moieties fused with five-membered heteroaryl moieties include unsubstituted and substituted furo(2,3-b)pyridin-(4- or 5- or 6-)yl, 3H-imidazo(4,5-b)pyridin-(5- or 6- or 7-)yl, (1,3)thiazolo(4,5-b)pyrazin-(5- or 6-)yl, (1,3)thiazolo(4,5-b)pyridin-(5- or 6- or 7-)yl, and thieno(2,3-b)pyridin-(4- or 5- or 6-)yl.

Six-membered heteroaryl moieties fused with other six-membered heteroaryl moieties include unsubstituted and substituted 1,5-naphthyridinyl, 1,7-naphthyridinyl, 1,8-naphthyridinyl, pteridinyl, pyridazino(4,5-d)pyridazinyl, pyrido(2,3-d)pyridazinyl, and pyrido(3,4-d)pyridazinyl.

"Heterocyclyl" means (a) monovalent, non-aromatic, unsubstituted and substituted four-membered ring moieties having one nitrogen, oxygen, or sulfur atom and the remaining atoms are carbon atoms, zero double bonds, attached through a carbon atom or a nitrogen atom, (b) monovalent, non-aromatic, unsubstituted and substituted five-membered ring moieties having one or two nitrogen, oxygen, or sulfur atoms and the remaining atoms are carbon atoms, and zero or one double bonds, attached through a carbon atom or a nitrogen atom, and (c) monovalent, non-aromatic, unsubstituted and substituted six-membered ring moieties having one or two or three nitrogen, oxygen, or sulfur atoms and the remaining atoms are carbon atoms, and zero, one, or two double bonds, attached through a carbon atom or a nitrogen atom.

Examples of four-membered heterocyclyl moieties are unsubstituted and substituted oxetane, thietane, and azetidine.

Examples of five-membered heterocyclyl moieties include unsubstituted and substituted 1,4-dioxanyl, 1,3-dioxolanyl, imidazolidinyl, 2-imidazolinyl, 4,5-dihydroisoxazolyl, pyrazolidinyl, 2-pyrazolinyl, pyrrolidinyl, 2-pyrrolinyl, 3-pyrrolinyl, and 2H-pyrrolyl.

Examples of six-membered heterocyclyl moieties include unsubstituted and substituted 1,3-dithianyl, 1,4-dithianyl, morpholinyl, piperidinyl, piperazinyl, pyranyl, 2H-pyranyl, 4H-pyranyl, and thiomorpholinyl.

Substituted aryl and heteroaryl moieties are those moieties substituted with one, two, three, four, or five substituents independently selected from the group consisting of alkyl, alkenyl, alkynyl, cycloalkyl, halo, —CN, —OH, —SH, —NH$_2$, —NO$_2$, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)(alkyl), —SO$_2$(alkyl), —C(O)H, —C(O)(alkyl), —C(O)OH, —C(O)O(alkyl), —NH(alkyl), —N(alkyl)$_2$, —C(O)NH$_2$, —C(O)NH(alkyl), —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and R$^{40}$, in which R$^{30}$ is alkyl or alkyl substituted with one substituent selected from the group consisting of halo, —O(alkyl), and —S(alkyl), and R$^{40}$ is furyl, imidazolyl, indazolidinyl, isoquinolinyl, isothiazolyl, isoxazolyl, morpholinyl, naphthyl, naphthyridyl, 1,2,3-oxadiazolyl, oxazolyl, phenyl, piperidinyl, piperazinyl, pyrazinyl, pyrazolyl, pyridyl, pyrimidinyl, pyrrolidinyl, pyrrolyl, quinazolyl, quinolinyl, quinoxalyl, tetrazolyl, 1,2,3-thiadiazolyl, 1,3,4-thiadiazolyl, thiazolyl, thienyl, 1,2,3-triazolyl, or thiomorpholinyl, in which each R$^{40}$ moiety is unsubstituted or substituted with one or two or three substituents independently selected from the group consisting of alkyl, alkenyl, alkynyl, cycloalkyl, halo, =O, —CN, —OH, —SH, —NO$_2$, —CF$_3$, —CH$_2$CF$_3$, —CF$_2$CF$_3$, —OCF$_3$, —OCH$_2$CF$_3$, —OCF$_2$CF$_3$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), and —SO$_2$N(alkyl)$_2$.

Substituted cycloalkyl, cycloalkenyl, and heterocyclyl moieties are those moieties substituted with one or two or three substituents independently selected from the group consisting of alkyl, phenyl, halo, —CN, —OH, —NH$_2$, —CF$_3$, —OR$^{30}$, —SR$^{30}$, —S(O)(alkyl), —SO$_2$(alkyl), —C(O)H, —C(O)(alkyl), —C(O)OH, —C(O)O(alkyl), —NH(alkyl), —N(alkyl)$_2$, —C(O)NH$_2$, —C(O)NH(alkyl), and —C(O)N(alkyl)$_2$, in which the phenyl is unsubstituted or substituted with one or two or three substituents independently selected from the group consisting of halo, —CN, —OH, —NH$_2$, and —CF$_3$.

"Hydroxyl protecting moiety" means selectively introducible and removable moieties which protect —OH moieties against undesirable side reactions. Hydroxyl protecting moieties include 4-nitrobenzyloxycarbonyl, 4-bromobenzyloxycarbonyl, 4-methoxybenzyloxycarbonyl, 3,4-dimethoxybenzyloxycarbonyl, tert-butoxycarbonyl, diphenylmethoxycarbonyl, 2,2,2-trichloroethoxycarbonyl, 2,2,2-tribromoethoxycarbonyl, 2-(trimethylsilyl)-ethoxycarbonyl, 2-(phenylsulfonyl)ethoxycarbonyl, allyloxycarbonyl, acetyl, chloroacetyl, dichloroacetyl, trichloroacetyl, trifluoroacetyl, methoxyacetyl, phenoxyacetyl, pivaloyl, propionyl, 2-methylpropionyl, benzoyl, tert-butyl, 2,2,2-trichloroethyl, 2-trimethylsilylethyl, 1,1-dimethyl-2-propenyl, 3-methyl-3-butenyl, para-methoxybenzyl, 3,4-dimethoxybenzyl, diphenylmethyl, triphenylmethyl, tetrahydrofuryl, benzyloxymethyl, 2-methoxyethoxymethyl, 2,2,2-trichloroethoxymethyl, 2-(trimethylsilyl)-ethoxymethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

These variable moieties may combine to provide a seventh embodiment of this invention, which embodiment is directed to compounds having formula (I) or formula (II), and pharmaceutically acceptable salts, prodrugs, and salts of prodrugs thereof, in which R$^1$ is hydrogen, —R$^{11}$, —C(O)OR$^{11}$, —C(O)NH$_2$, —C(O)NHR$^{12}$, or —C(O)NR$^{12}$R$^{13}$;

R$^2$ is hydrogen or R$^P$, in which R$^P$ is a hydroxyl protecting moiety;

one of R$^3$ or R$^4$ is hydrogen and the other is —OH, —OR$^P$, —OR$^{15}$, —OC(O)R$^{15}$, —OC(O)OR$^{15}$, —OC(O)NH$_2$, —OC(O)NHR$^{16}$, or —OC(O)NR$^{16}$R$^{17}$; or R$^3$ and R$^4$ together are =O or —CH$_2$O—;

R$^5$ is hydrogen, —R$^{19}$, —C(O)OR$^{19}$, —C(O)NH$_2$, —C(O)NHR$^{20}$, or —C(O)NR$^{20}$R$^{21}$;

R$^6$ and R$^{10}$ are independently hydrogen or —R$^{23}$;

R$^7$ is =O, =NOH, =NOR$^P$, or =NOR$^{24}$;

one of R$^8$ and R$^9$ is hydrogen, and the other is —OH or —OR$^{32}$; or

R$^8$ and R$^9$ together are =O;

R$^{11}$, R$^{15}$, R$^{19}$, R$^{24}$, and R$^{26}$ are independently alkyl, —(CH$_2$)alkenyl, —(CH$_2$)alkynyl, alkyl substituted with one or two or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

R$^{12}$, R$^{13}$, R$^{16}$, R$^{17}$, R$^{20}$, R$^{21}$, R$^{27}$, and R$^{28}$ are independently alkyl, cycloalkyl, —(CH$_2$)alkenyl, —(CH$_2$)alkynyl, cycloalkyl, aryl, heteroaryl, heterocyclyl, alkyl substituted with one substituent selected from the group consisting of cycloalkyl, aryl, heteroaryl, heterocyclyl, —NH$_2$, —NHR$^{30}$, and —NR$^{30}$R$^{31}$, —(CH$_2$)alkenyl substituted with one substituent selected from the group consisting of cycloalkyl, aryl, heteroaryl, heterocyclyl, —NH$_2$, —NHR$^{30}$, and —NR$^{30}$R$^{31}$, or —(CH$_2$)alkynyl substituted with one substituent selected from the group consisting of cycloalkyl, aryl, heteroaryl, heterocyclyl, —NH$_2$, —NHR$^{30}$, and —NR$^{30}$R$^{31}$;

$R^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, or alkynyl substituted with one or two or three substituents independently selected from the group consisting of cycloalkyl, aryl, heteroaryl, and heterocyclyl;

$R^{30}$ and $R^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$;

$R^{32}$ is —$R^{26}$, —C(O)O$R^{26}$, —C(O)NH$_2$, —C(O)NH$R^{27}$, or —C(O)N$R^{27}R^{28}$; and $X^1$ is hydrogen or fluoride;

compounds having formula (I) or formula (II), and pharmaceutically acceptable salts, prodrugs, and salts of prodrugs thereof, in which $R^1$ is hydrogen, —$R^{11}$, —C(O)O$R^{11}$, —C(O)NH$_2$, —C(O)NH$R^{12}$, or —C(O)N$R^{12}R^{13}$;

$R^2$ is hydrogen or $R^P$, in which $R^P$ is a hydroxyl protecting moiety;

one of $R^3$ or $R^4$ is hydrogen and the other is —OH, —OR$^P$, or —OC(O)$R^{15}$; or $R^3$ and $R^4$ together are =O or —CH$_2$O—;

$R^5$ is hydrogen, —$R^{19}$, —C(O)O$R^{19}$, —C(O)NH$_2$, —C(O)NH$R^{20}$, or —C(O)N$R^{20}R^{21}$;

$R^6$ and $R^{10}$ are independently hydrogen or —$R^{23}$;

$R^7$ is =O, =NOH, =NO$R^P$, or =NO$R^{24}$;

one of $R^8$ and $R^9$ is hydrogen, and the other is —OH or —OR$^{32}$; or $R^8$ and $R^9$ together are =O;

$R^{11}$, $R^{15}$, $R^{19}$, $R^{24}$, and $R^{26}$ are independently alkyl, —(CH$_2$)alkenyl, —(CH$_2$)alkynyl, alkyl substituted with one or two or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

$R^{12}$, $R^{13}$, $R^{20}$, $R^{21}$, $R^{27}$, and $R^{28}$ are independently alkyl, cycloalkyl, —(CH$_2$)alkenyl, —(CH$_2$)alkynyl, cycloalkyl, aryl, heteroaryl, heterocyclyl, alkyl substituted with one substituent selected from the group consisting of cycloalkyl, aryl, heteroaryl, heterocyclyl, —NH$_2$, —NH$R^{30}$, and —N$R^{30}R^{31}$, —(CH$_2$)alkenyl substituted with one substituent selected from the group consisting of cycloalkyl, aryl, heteroaryl, heterocyclyl, —NH$_2$, —NH$R^{30}$, and —N$R^{30}R^{31}$, or —(CH$_2$)alkynyl substituted with one substituent selected from the group consisting of cycloalkyl, aryl, heteroaryl, heterocyclyl, —NH$_2$, —NH$R^{30}$, and —N$R^{30}R^{31}$;

$R^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, or alkynyl substituted with one or two or three substituents independently selected from the group consisting of cycloalkyl, aryl, heteroaryl, and heterocyclyl;

$R^{30}$ and $R^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$;

$R^{32}$ is —$R^{26}$, —C(O)O$R^{26}$, —C(O)NH$_2$, —C(O)NH$R^{27}$, or —C(O)N$R^{27}R^{28}$; and $X^1$ is hydrogen or fluoride;

compounds having formula (I) or formula (II), and pharmaceutically acceptable salts, prodrugs, and salts of prodrugs thereof, in which $R^1$ is methyl, ethyl, prop-2-ynyl, or prop-2-enyl, each of which is unsubstituted or substituted with one substituent selected from the group consisting of phenyl, quinolinyl, isoquinolinyl, quinazolinyl, and quinoxalinyl in which each substitutuent is unsubstituted or substituted with one or two substitutuents independently selected from the group consisting of —F, —Cl, —Br, —I and —NO$_2$; $R^2$ is hydrogen; $R^3$ is —OH, ((phenyl)carbonyl)oxy, ((methyl)carbonyl)oxy, (trimethylsilyl)oxy, or (triethylsilyl)oxy and $R^4$ is hydrogen, or $R^3$ and $R^4$ together are =O or —CH$_2$O—; $R^5$ is hydrogen, methyl, ethyl, propyl, prop-2-ynyl, prop-2-enyl, phenylmethyl, 4-methoxyphenylmethyl or 2,4-dimethoxyphenylmethyl; $R^6$ is hydrogen, methyl, ethyl, ethynyl, or phenyl; $R^7$ is =O; $R^8$ is hydrogen and $R^9$ is —OH, or $R^8$ and $R^9$ together are =O; $R^{10}$ is hydrogen, methyl, ethyl, prop-2-ynyl or prop-2-enyl; and $X^1$ is hydrogen or fluoride;

compounds having formula (I) or formula (II), and pharmaceutically acceptable salts, prodrugs, and salts of prodrugs thereof, in which $R^1$ is prop-2-ynyl substituted with isoxazoyl, in which the isoxazolyl is substituted with one substituent selected from the group consisting of furyl, imidazolyl, isoquinolinyl, isothiazolyl, isoxazolyl, 1,2,3-oxadiazolyl, oxazolyl, pyridyl, pyrimidinyl, quinolinyl, tetrazolyl, 1,2,3-thiadiazolyl, 1,3,4-thiadiazolyl, thiazolyl, thienyl, and 1,2,3-triazolyl, in which each substitutuent is unsubstituted or substituted with one or two substitutuents independently selected from the group consisting of —F, —Cl, —Br, —I and —NO$_2$; $R^2$ is hydrogen; $R^3$ is —OH, ((phenyl)carbonyl)oxy, ((methyl)carbonyl)oxy, (trimethylsilyl)oxy, or (triethylsilyl)oxy and $R^4$ is hydrogen, or $R^3$ and $R^4$ together are =O or —CH$_2$O—; $R^5$ is hydrogen, methyl, ethyl, propyl, prop-2-ynyl, prop-2-enyl, phenylmethyl, 4-methoxyphenylmethyl, or 2,4-dimethoxyphenylmethyl; $R^6$ is hydrogen, methyl, ethyl, ethenyl, or phenyl; $R^7$ is =O; $R^8$ is hydrogen and $R^9$ is —OH, or $R^8$ and $R^9$ together are =O; $R^{10}$ is hydrogen, methyl, ethyl, prop-2-ynyl or prop-2-enyl; and $X^1$ is hydrogen or fluoride;

compounds having formula (I) or formula (II), and pharmaceutically acceptable salts, prodrugs, and salts of prodrugs thereof, in which $R^1$ is prop-2-ynyl substituted with thienyl, in which the thienyl is substituted with one substituent selected from the group consisting of furyl, imidazolyl, isoquinolinyl, isothiazolyl, isoxazolyl, 1,2,3-oxadiazolyl, oxazolyl, pyridyl, pyrimidinyl, quinolinyl, tetrazolyl, 1,2,3-thiadiazolyl, 1,3,4-thiadiazolyl, thiazolyl, thienyl, and 1,2,3-triazolyl, in which each substitutuent is unsubstituted or substituted with one or two substitutuents independently selected from the group consisting of —F, —Cl, —Br, —I and —NO$_2$; R$^2$ is hydrogen; R$^3$ is —OH, ((phenyl)carbonyl)oxy, ((methyl)carbonyl)oxy, (trimethylsilyl)oxy, or (triethylsilyl)oxy and R$^4$ is hydrogen, or R$^3$ and R$^4$ together are =O or —CH$_2$O—; R$^5$ is hydrogen, methyl, ethyl, propyl, prop-2-ynyl, prop-2-enyl, phenylmethyl, 4-methoxyphenylmethyl, or 2,4-dimethoxyphenylmethyl; —R$^6$ is hydrogen, methyl, ethyl, ethenyl, or phenyl; R$^7$ is =O; R$^8$ is hydrogen and R$^9$ is —OH, or R$^8$ and R$^9$ together are =O; R$^{10}$ is hydrogen, methyl, ethyl, prop-2-ynyl or prop-2-enyl; and X$^1$ is hydrogen or fluoride;

compounds having formula (I) or formula (II), and pharmaceutically acceptable salts, prodrugs, and salts of prodrugs thereof, in which R$^1$ is prop-2-enyl substituted with isoxazoyl, in which the isoxazolyl is substituted with one substituent selected from the group consisting of furyl, imidazolyl, isoquinolinyl, isothiazolyl, isoxazolyl, 1,2,3-oxadiazolyl, oxazolyl, pyridyl, pyrimidinyl, quinolinyl, tetrazolyl, 1,2,3-thiadiazolyl, 1,3,4-thiadiazolyl, thiazolyl, thienyl, and 1,2,3-triazolyl, in which each substitutuent is unsubstituted or substituted with one or two substitutuents independently selected from the group consisting of —F, —Cl, —Br, —I and —NO$_2$; R$^2$ is hydrogen; R$^3$ is —OH, ((phenyl)carbonyl)oxy, ((methyl)carbonyl)oxy, (trimethylsilyl)oxy, or (triethylsilyl)oxy and R$^4$ is hydrogen, or R$^3$ and R$^4$ together are =O or —CH$_2$O—; R$^5$ is hydrogen, methyl, ethyl, propyl, prop-2-ynyl, prop-2-enyl, phenylmethyl, 4-methoxyphenylmethyl, or 2,4-dimethoxyphenylmethyl; R$^6$ is hydrogen, methyl, ethyl, ethenyl, or phenyl; R$^7$ is =O; R$^8$ is hydrogen and R$^9$ is —OH, or R$^8$ and R$^9$ together are =O; R$^{10}$ is hydrogen, methyl, ethyl, prop-2-ynyl or prop-2-enyl; and X$^1$ is hydrogen or fluoride;

compounds having formula (I) or formula (II), and pharmaceutically acceptable salts, prodrugs, and salts of prodrugs thereof, in which R$^1$ is prop-2-enyl substituted with thienyl, in which the thienyl is substituted with one substituent selected from the group consisting of furyl, imidazolyl, isoquinolinyl, isothiazolyl, isoxazolyl, 1,2,3-oxadiazolyl, oxazolyl, pyridyl, pyrimidinyl, quinolinyl, tetrazolyl, 1,2,3-thiadiazolyl, 1,3,4-thiadiazolyl, thiazolyl, thienyl, and 1,2,3-triazolyl, in which each substitutuent is unsubstituted or substituted with one or two substitutuents independently selected from the group consisting of —F, —Cl, —Br, —I and —NO$_2$; R$^2$ is hydrogen; R$^3$ is —OH, ((phenyl)carbonyl)oxy, ((methyl)carbonyl)oxy, (trimethylsilyl)oxy, or (triethylsilyl)oxy and R$^4$ is hydrogen, or R$^3$ and R$^4$ together are =O or —CH$_2$O—; R$^5$ is hydrogen, methyl, ethyl, propyl, prop-2-ynyl, prop-2-enyl, phenylmethyl, 4-methoxyphenylmethyl, or 2,4-dimethoxyphenylmethyl; R$^6$ is hydrogen, methyl, ethyl, ethenyl, or phenyl; R$^7$ is =O; R$^8$ is hydrogen and R$^9$ is —OH, or R$^8$ and R$^9$ together are =O; R$^{10}$ is hydrogen, methyl, ethyl, prop-2-ynyl or prop-2-enyl; and X$^1$ is hydrogen or fluoride; and compounds having formula (I) or formula (II), and pharmaceutically acceptable salts, prodrugs, and salts of prodrugs thereof, in which R$^1$ is methyl, prop-2-ynyl, 3-(5-pyridin-2-ylthien-2-yl)prop-2-ynyl, 3-(quinolin-3-yl)prop-2-enyl, 3-(3-pyridin-2-ylisoxazol-5-yl)prop-2-ynyl, or 3-(5-pyrimidin-2-ylthien-2-yl)prop-2-ynyl; R$^2$ is hydrogen; R$^3$ is —OH, ((phenyl)carbonyl)oxy, ((methyl)carbonyl)oxy, (trimethylsilyl)oxy, or (triethylsilyl)oxy and R$^4$ is hydrogen, or R$^3$ and R$^4$ together are =O or —CH$_2$O—; R$^5$ is hydrogen, methyl, ethyl, propyl, prop-2-ynyl, prop-2-enyl, phenylmethyl, 4-methoxyphenylmethyl, or 2,4-dimethoxyphenylmethyl; R$^6$ is hydrogen, methyl, ethyl, ethenyl, or phenyl; R$^7$ is =O; R$^8$ is hydrogen and R$^9$ is —OH, or R$^8$ and R$^9$ together are =O; R$^{10}$ is hydrogen, methyl, ethyl, prop-2-ynyl or prop-2-enyl; and X$^1$ is hydrogen or fluoride.

Specific examples of R$^1$ moieties for the practice of this invention are methyl, prop-2-ynyl, and 3-(5-pyridin-2-ylthien-2-yl)prop-2-ynyl.

A specific example of a R$^2$ moiety for the practice of this invention is hydrogen.

A specific example of a R$^3$ moiety for the practice of this invention is ((phenyl)carbonyl)oxy.

A specific example of a R$^4$ moiety for the practice of this invention is hydrogen.

Specific examples of R$^5$ moieties for the practice of this invention are hydrogen and methyl.

A specific example of a R$^6$ moiety for the practice of this invention is hydrogen.

A specific example of a R$^7$ moiety for the practice of this invention is =O.

A specific example of R$^8$ and R$^9$ moieties for the practice of this invention is R$^8$ and R$^9$ together are =O.

A specific example of a R$^{10}$ moiety for the practice of this invention is hydrogen.

A specific example of a X$^1$ moiety for the practice of this invention is hydrogen.

These specific moieties may combine to provide an eighth embodiment of this invention, which embodiment is directed to compounds having formula (I) or formula (II), and pharmaceutically acceptable salts, prodrugs, or salts of prodrugs thereof, in which R$^1$ is alkyl, —(CH$_2$)alkynyl, or —(CH$_2$)alkynyl substituted with thienyl, in which the thienyl is substituted with pyridyl; R$^2$ is hydrogen; R$^3$ is ((phenyl)carbonyl)oxy; R$^4$ is hydrogen; R$^5$ is hydrogen or alkyl; R$^6$ is hydrogen; R$^7$ is =O; R$^8$ and R$^9$ together are =O; R$^{10}$ is hydrogen; and X$^1$ is hydrogen;

compounds having formula (I) or formula (II), and pharmaceutically acceptable salts, prodrugs, or salts of prodrugs thereof, in which R$^1$ is methyl, prop-2-ynyl or prop-2-ynyl substituted with thienyl, in which the thienyl is substituted with pyridyl; R$^2$ is hydrogen; R$^3$ is ((phenyl)carbonyl)oxy; R$^4$ is hydrogen; R$^5$ is hydrogen or methyl; R$^6$ is hydrogen; R$^7$ is =O; R$^8$ and R$^9$ together are =O; R$^{10}$ is hydrogen; and X$^1$ is hydrogen;

compounds having formula (I) or formula (II), and pharmaceutically acceptable salts, prodrugs, and salts of prodrugs thereof, in which R$^1$ is methyl; R$^2$ is hydrogen; R$^3$ is ((phenyl)carbonyl)oxy; R$^4$ is hydrogen; R$^5$ is hydrogen or methyl; R$^6$ is hydrogen; R$^7$ is =O; R$^8$ and R$^9$ together are =O; R$^{10}$ is hydrogen; and X$^1$ is hydrogen;

compounds having formula (I) or formula (II), and pharmaceutically acceptable salts, prodrugs, and salts of prodrugs thereof, in which R$^1$ is prop-2-ynyl; R$^2$ is hydrogen; R$^3$ is ((phenyl)carbonyl)oxy; R$^4$ is hydrogen; R$^5$ is hydrogen or methyl; R$^6$ is hydrogen; R$^7$ is =O; R$^8$ and R$^9$ together are =O; R$^{10}$ is hydrogen; and X$^1$ is hydrogen;

compounds having formula (I) or formula (II), and pharmaceutically acceptable salts, prodrugs, or salts of prodrugs thereof, in which R$^1$ is 3-(5-pyridin-2-ylthien-2-yl)prop-2-ynyl; R$^2$ is hydrogen; R$^3$ is ((phenyl)carbonyl)oxy; R$^4$ is hydrogen; R$^5$ is hydrogen or methyl; R$^6$ is hydrogen; R$^7$ is =O; R$^8$ and R$^9$ together are =O; R$^{10}$ is hydrogen; and X$^1$ is hydrogen; and compounds, and pharmaceutically acceptable salts, prodrugs, and salts of prodrugs thereof, which are (2aR,4aS,6R,8S,9R,10R,12R,15R,15aS,15bS)-15-ethyl-12-fluoro-8-methoxy-3,4a,6,8,10,12,15a-heptamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-8-methoxy-4a,6,8,10,12,15a-hexamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-8-methoxy-4a,6,8,10,12,15a-hexamethyl-2,5,11,13-tetraoxohexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-8-methoxy-3,4a,6,8,10,12,15a-heptamethyl-2,5,13-trioxo-9-(( 3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-8-methoxy-4a-6,8,10,12,15a-hexamethyl-2,5,13-trioxo-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-8-methoxy-4a-6,8,10,12,15a-hexamethyl-2,5,13-trioxo-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-12-fluoro-8-methoxy-4a-6,8,10,12,15a-hexamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-3,4a,6,8,10,12,15a-heptamethyl-2,5,11,13-tetraoxo-8-(prop-2-ynyloxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6,8,10,12,15a-hexamethyl-2,5,11,13-tetraoxo-8-(prop-2-ynyloxy)hexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,6,8,10,12,15a-hexamethyl-2,5,11,13-tetraoxo- 8-(prop-2-ynyloxy)hexadecahydro-2H-1,14-dioxa-3-azacyclotetradeca(1,2,3-cd)pentalen-9-yl 3,4,6-trideoxy-3(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-(prop-2-ynyloxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-(prop-2-ynyloxy)hexadecahydro-2H-1,14-dioxa3azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,13-trioxo-8-(prop-2-ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-4a,6,8,10,12,15a-hexamethyl-2,5,13-trioxo-8-(prop-2-ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-β-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-(prop-2-ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-12-fluoro-3,4a-6,8,10,12,15a-heptamethyl-2,5,11,13-tetraoxo-8-(( 3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6,8,10,12,15a-hexamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a-6,8,10,12,15a-hexamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,13-trioxo-8-((3-(5-(pyridin-2-yl)thien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-4a,6,8,10,12,15a-hexamethyl-2,5,13-trioxo-8-((3-(5-(pyridin-2-yl)thien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-((3-(5-pyridin-2-yl)thien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylohexopyranoside;

(2aR,4aS,6R,8S,9R,10R,12R,15R,15aS,15bS)-15-ethyl-12-fluoro-3,4a,6,8,10,12,15a-heptamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6,8,10,12,15a-hexamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,6,8,10,12,15a-hexamethyl-2,5,11,13-tetraoxo-8-((3-(5-pyrimidin-2-ylthien-2-yl)prop-2-ynyl)oxy)hexadecahydro- 2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,13-trioxo-8-((3-(5-pyrimidin-2-ylthien-2-yl)prop-2-ynyl)oxy)-9-((3,4,6-trideoxy-3-(dimethylamino)-β-D-xylo-hexopyranosyl)oxy)-hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15ethyl-4a,6,8,10,12,15a-hexamethyl-2,5,13-trioxo-8-((3-(5-pyrimidin-2-ylthien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-((3-(5-pyrimidin-2-ylthien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca( 1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-3,4a,6,8,10,12,15a-heptamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6,8,10,12,15a-hexamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,-6,8,10,12,15a-hexamethyl-2,5,11,13-tetraoxo-8-((3-(3-pyridin-2-ylisoxazol-5-yl)prop-2-ynyl)oxy)hexadecahydro-2H-1,14-dioxa-3azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca( 1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,11,13-trioxo-8-((3-(3-pyridin-2-ylisoxazol-5-yl)prop-2-ynyl)oxy)-9-((3,4,6-trideoxy-3-(dimethylamino)-β-D-xylo-hexopyranosyl)oxy)-hexadecahydro-2H-1,14-dioxa-3-azacyclotetradeca(1,2,3-cd)-pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-4a,6,8,10,12,15a-hexamethyl-2,5,13-trioxo-8-((3-(3-pyridin-2-ylisoxazol-5-yl)prop-2-ynyl)oxy)-9-((3,4,6-trideoxy-3-(dimethylamino)-β-D-xylo-hexopyranosyl)oxy)-hexadecahydro-2H-1,14-dioxa-3-azacyclotetradeca(1,2,3-cd)-pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-((3-(3-pyridin-2-ylisoxazol-5-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-3,4a,6,8,10,12,15a-heptamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6,8,10,12,15a-hexamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,6,8,10,12,15a-hexamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd) pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,13-trioxo-8-(((2E)-3-quinolin-3-ylprop-2-enyl)oxy)-9-((3,4,6-trideoxy-3(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15ethyl-4a,6,8,10,12,15a-hexamethyl-2,5,13-trioxo-8-(((2E)-3-quinolin-3-ylprop-2-enyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopryranoside;

(2aR,4aS,6R,8S,9R,10R,12R,15R,15aS,15bS)-15-ethyl-4a,6,8,10,12,15a-hexamethyl-2,5,13-trioxo-8-(((2E)-3-quinolin-3-ylprop-2-enyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-8-methoxy-3,4a,6,8,10,12,15a-heptamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aS,4aR,6R,8S,9R,10R,12R,15R,15aS,15bR)-15-ethyl-8-methoxy-3,4a,6,8,10,12,15a-heptamethyl-2,5,11,13-tetraoxohexadecahydro-2H-1,14-dioxa-3-azacyiotetradeca-(1,2,3-cd)pentalen-9-yl 3,4,6-trideoxy-3-(dimethylamino)-β-D-xylo-hexopyranoside;

(2aR,4aS,6R,8S,9R,10S,11S,12R,15R,15aS,15bS)-15-ethyl-3,4a,6,8,10,12,15a-heptamethyl-2,5,13-trioxo-8-(prop-2-ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 4-O-benzoyl-2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-(prop-2-ynyloxy)hexadecahydro-2H-1,14-dioxa-3-azacyclotetradeca-(1,2,3-cd)pentalen-9-yl 3,4,6-trideoxy-3-(dimethylamino)-β-D-xylo-hexopyranoside; and (2aR,4aS,6R,8S,9R,10R,12R,15R,15aS,15bS)-15-ethyl-8-methoxy-4a,6,8,10,12,15a-hexamethyl-2,5,11,13-tetraoxohexa-decahydro-2H-1,14-dioxa-3-azacyclotetradeca (1,2,3-cd)-pentalen-9-yl 3,4,6-trideoxy-3-(dimethylamino)-β-D-xylo-hexopyranoside.

Compounds of this invention contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13–10. Compounds having asymmetrically substituted carbon atoms with equal amounts of R and S configurations are racemic at those carbon atoms. Atoms with an excess of one configuration over the other are assigned the configuration which is present in the higher amount, preferably an excess of about 85%–90%, more preferably an excess of about 95%–99%, and still more preferably an excess greater than about 99%. Accordingly, this invention is meant to embrace all stereoisomers of the compounds including racemic mixtures, enantiomers, mixtures of enantiomers, diastereomers, and mixtures of diastereomers.

Individual stereoisomers of the compounds may be prepared by any one of a number of methods within the knowledge of the ordinarily skilled practioner. These methods include stereospecific synthesis, chromatographic separation of diastereomers, chromatographic resolution of enantiomers, enzymatic resolution, and conversion of enantiomers in an enantiomeric mixture to diastereomers and chromatographically separating the diastereomers and regeneration of the individual enantiomers.

Stereospecific synthesis involves the use of appropriate chiral starting materials and synthetic reactions which do not cause racemization or inversion of stereochemistry at the chiral centers.

Diastereomeric mixtures of compounds resulting from a synthetic reaction can be separated by chromatographic techniques which are well-known to the ordinarily skilled practioner.

Chromatographic resolution of enantiomers can be accomplished on chiral commercially available chromatography resins. In practice, the racemate is placed in solution and loaded onto the column containing a chiral stationary phase. The enantiomers are then separated by high performance liquid chromatography.

Enzymes, such as esterases, phosphatases and lipases, may be useful for resolution of derivatives of the enantiomers in an enantiomeric mixture. For example, an ester derivative of a carboxyl group of the compounds to be separated can be prepared. Certain enzymes will selectively hydrolyze only one of the enantiomers in the mixture. Then the resulting enantiomerically pure acid can be separated from the unhydrolyzed ester.

Resolution of enantiomers may also be accomplished by converting the enantiomers in the mixture to diastereomers by reacting of the former and chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and reused.

Compounds of this invention may also contain carbon-carbon double bonds in the Z or E configuration, in which the term "Z" represents the larger two substituents on the same side of a carbon-carbon double bond and the term "E"

represents the larger two substituents on opposite sides of a carbon-carbon double bond. The compounds may also exist as an equilibrium mixture of Z or E configurations.

Compounds of this invention which contain hydroxyl, amino, or carboxylic acids may have attached thereto prodrug-forming moieties. The prodrug-forming moieties are removed by metabolic processes and release the compounds having the freed hydroxyl, amino, or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Compounds of this invention may exist as acid addition salts, basic addition salts, or zwitterions. Salts of the compounds are prepared during their isolation or following their purification. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maieate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate, salts of the compounds and prodrugs thereof are embraced by this invention. When the compounds contain carboxylic acids, basic addition salts may be prepared therefrom by reaction with a base such as the hydroxide, carbonate, and bicarbonate of cations such as lithium, sodium, potassium, calcium, and magnesium.

Compounds of this invention may be administered with or without an excipient. Excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof. Excipients for orally administered compounds in solid dosage forms include agar, alginic acid, aluminum hydroxide, benzyl alcohol, benzyl benzoate, 1,3-butylene glycol, castor oil, cellulose, cellulose acetate, cocoa butter, corn starch, corn oil, cottonseed oil, ethanol, ethyl acetate, ethyl carbonate, ethyl cellulose, ethyl laureate, ethyl oleate, gelatin, germ oil, glucose, glycerol, groundnut oil, isopropanol, isotonic saline, lactose, magnesium hydroxide, magnesium stearate, malt, olive oil, peanut oil, potassium phosphate salts, potato starch, propylene glycol, Ringer's solution, talc, tragacanth, water, safflower oil, sesame oil, sodium carboxymethyl cellulose, sodium lauryl sulfate, sodiumphosphate salts, soybean oil, sucrose, tetrahydrofurfuryl alcohol, and mixtures. Excipients for ophthalmically and orally administered compounds in liquid dosage forms include benzyl alcohol, benzyl benzoate, 1,3-butylene glycol, castor oil, corn oil, cottonseed oil, ethanol, ethyl acetate, ethyl carbonate, fatty acid esters of sorbitan, germ oil, groundnut oil, glycerol, isopropanol, olive oil, polyethylene glycols, propylene glycol, sesame oil, tetrahydrofurfuryl alcohol, water, and mixtures thereof. Excipients for osmotically administered compounds include chlorofluorohydrocarbons, ethanol, isopropanol, water, and mixtures thereof. Excipients for parenterally administered compounds include 1,3-butanediol, castor oil, corn oil, cottonseed oil, germ oil, groundnut oil, liposomes, oleic acid, olive oil, peanut oil, Ringer's solution, safflower oil, sesame oil, soybean oil, U.S.P. or isotonic sodium chloride solution, water, and mixtures thereof. Excipients for rectally and vaginally administered compounds include cocoa butter, polyethylene glycol, wax, and mixtures thereof.

Compounds of this invention may be administered orally, ophthalmically, osmotically, parenterally (subcutaneously, intramuscularly, intrasternally, intravenously), rectally, topically, transdermally, and vaginally. Orally administered compounds in solid dosage forms may be administered as capsules, dragees, granules, pills, powders, and tablets. Ophthalmically and orally administered compounds in liquid dosage forms may be administered as elixirs, emulsions, microemulsions, solutions, suspensions, and syrups. Osmotically and topically administered compounds may be administered as creams, gels, inhalants, lotions, ointments, pastes, powders, solutions, and sprays. Parenterally administered compounds may be administered as aqueous or oleaginous solutions or aqueous or oleaginous and suspensions, in which suspensions comprise crystalline, amorphous, or otherwise insoluble forms of the compounds. Rectally and vaginally administered compounds may be administered as creams, gels, lotions, ointments, and pastes.

Therapeutically effective amounts of compounds of this invention depend on the recepient of treatment, the disorder being treated and the severity of the disorder, the composition comprising the compounds, the time of administration, the route of administration, the duration of treatment, the potency of the compounds, and the rate of excretion of the compounds. The daily therapeutically effective amount of the compounds administered to a patient in single or divided doses range from about 0.1 to about 200 mg/kg body weight, preferably from about 0.25 to about 100 mg/kg body weight. Single dose compositions contain these amounts of the compounds or combinations of submultiples thereof.

To determine antibacterial activity of the compounds of this invention, twelve petri dishes, each containing successive aqueous dilutions of test compounds in sterilized Brain Heart Infusion agar (Difco 0418-01-5) (10 mL), were inoculated with 1:100 dilutions of the representative microorganisms in TABLE 1 using a Steers replicator block (or 1:10 dilutions for slow-growing Streptococcus strains), co-incubated at 35–37° C. for 20–24 hours with a plate with a control plate having no compound, and inspected visually to provide the minimum inhibitory concentration (MIC), in $\mu$g/mL, by which is meant the lowest concentration of the test compound which yielded no growth, a slight haze, or sparsely isolated colonies on the inoculums spot as compared to growth in the control plate.

TABLE 1

| Microorganism | Code |
| --- | --- |
| Staphylococcus aureus NCTC10649M | AA |
| Staphylococcus aureus A5177 | BB |
| Staphylococcus aureus PIU 2043 | CC |
| Staphylococcus aureus 1775 | DD |
| Streptococcus pyrogenes EES61 | EE |
| Streptococcus pyrogenes 930 | FF |
| Streptococcus pyrogenes PIU 2548 | GG |
| Streptococcus pneumoniae ATCC 6303 | HH |

TABLE 1-continued

| Microorganism | Code |
| --- | --- |
| *Streptococcus pneumoniae* 5979 | JJ |
| *Streptococcus pneumoniae* 5649 | KK |
| *Enterococcus faecalis* PIU 1967 | LL |
| *Enterococcus faecium* GYR 1632 | MM |
| *Moraxella catarrhalis* 2604 | NN |
| *Haemophilus influenzae* GYR 1435 | PP |
| *Escherichia coli* JUHL | QQ |

The ability of the compounds to inhibit bacterial growth was superior to the control and in the range of about 0.5 μg/mL to greater than about 128 μg/mL against the microorganisms listed in TABLE 1. These data demonstrate the usefulness of the compounds as antibacterials.

It is meant to be understood that certain metabolites of compounds of this invention, which metabolites are produced by in vitro or in vivo metabolic processes, would also be useful as antibacterials and are meant to be embraced by this invention.

It is still also meant to be understood that certain precursor compounds, which precursor compounds may be metabolized in vitro or in vivo to form compounds of this invention, are meant to be embraced by this invention.

Compounds of this invention may also be prepared by synthetic chemical processes, examples of which synthetic chemical processes, and intermediates employed in the processes, are shown hereinbelow. It is meant to be understood that the order of the steps in the processes may be varied, reagents, solvents, and reaction conditions may be substituted for those specifically mentioned, and vulnerable moieties may be protected and deprotected, as necessary, during the process.

Abbreviations used herein are DMF for N,N-dimethylformamide; THF for tetrahydrofuran.

SCHEME 1

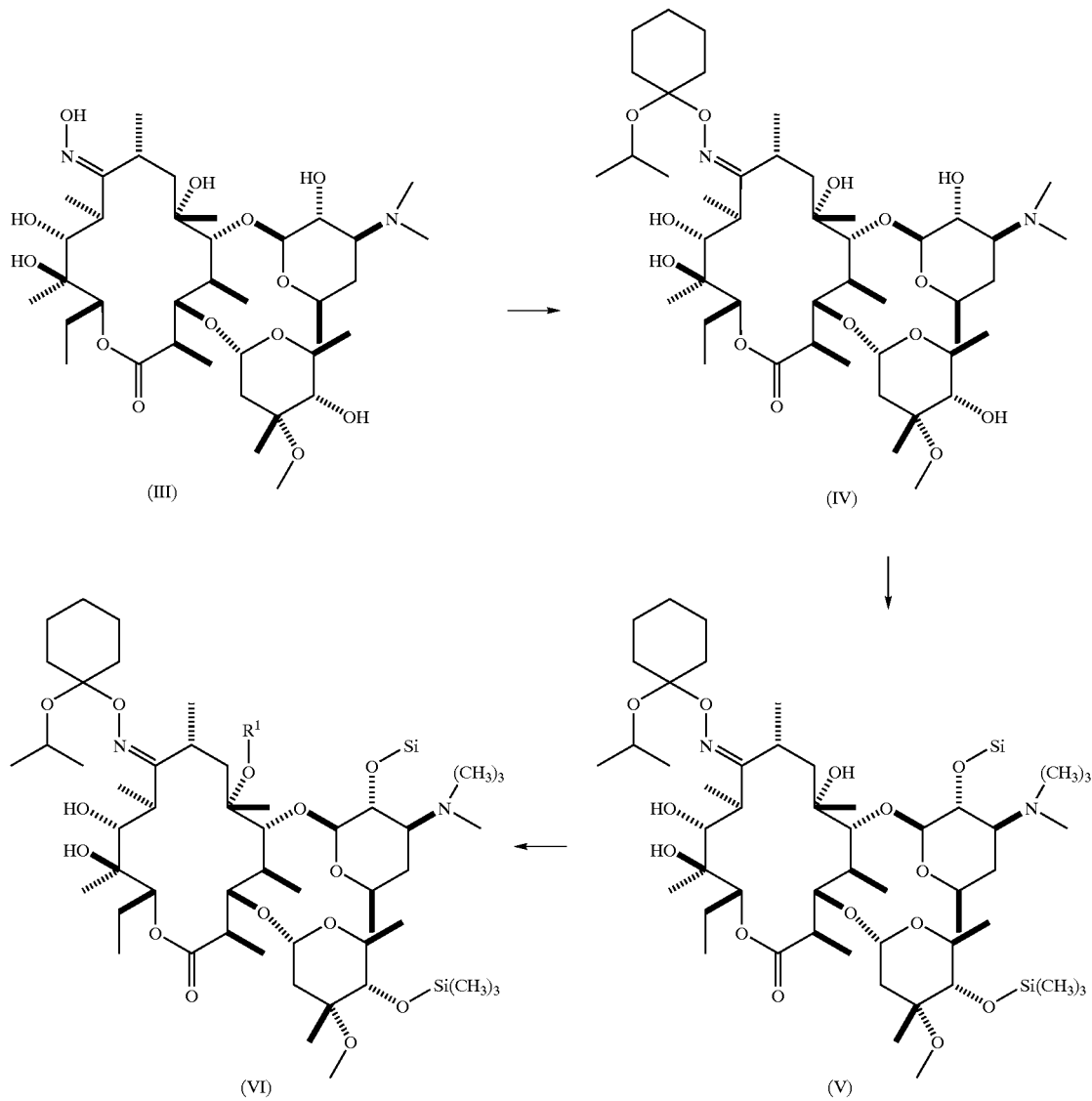

The compound having formula (III) may be prepared from erythromycin A as described in U.S. Pat. No. 5,274,085, column 3, lines 41–48 and U.S. Pat. No. 5,808,017, column 4, lines 37–53.

The compound having formula (III) may be converted to the compound having formula (IV) as described in U.S. Pat. No. 4,990,602, column 23, lines 11–19.

The compound having formula (IV) may be converted to the compound having formula (V) as described in U.S. Pat. No. 4,990,602, column 23, lines 34–42.

The compound having formula (V) may be converted to compounds having formula (VI) by reacting the former, a compound having formula $X^2—R^1$, in which $X^2$ is —Cl or —Br, and a first base.

Examples of compounds having formula $X^2—R^1$ include compounds having formula $X^2—R^{11}$, $X^2—C(O)OR^{11}$, $X^2—C(O)NH_2$, $X^2—C(O)NHR^{12}$, and $X^2—C(O)NR^{12}R^{13}$.

Examples of compounds having formula $X^2—R^{11}$ include bromomethane, 3-bromoprop-1-ene, 3-bromoprop-1-yne, benzyl bromide, 2-fluoroethyl bromide, 4-nitrobenzyl bromide, 4-chlorobenzyl bromide, 4-methoxybenzyl bromide, (3-bromoprop-1-enyl)benzene, 1-bromobut-2-ene, 2-(5-(3-bromoprop-1-ynyl)thien-2-yl)pyridine, 1-bromopent-2-ene, 2-(3-bromoprop-1-enyl)naphthalene, 5-(3-bromoprop-1-ynyl)-2-thien-2-ylpyridine, 2-(3-bromoprop-1-ynyl)pyridine, 3-((1E)-3-bromoprop-1-enyl)quinoline, 2-(5-(3-bromoprop-1-ynyl)isoxazol-3-yl)pyridine, and 2-(5-(3-bromoprop-1-ynyl)thien-2-yl)pyrimidine.

Examples of compounds having formula $X^2—C(O)OR^{11}$ include ethyl chloroformate, methyl chloroformate, phenyl chloroformate, propargyl chloroformate, allyl chloroformate, 2-bromoethyl chloroformate, 1-chloroethyl chloroformate, 3-chloropropyl formate, 4-chlorobutyl formate, 3-butenyl chloroformate, 2-methoxyphenyl chloroformate, para-toluene chloroformate, and 4-methoxyphenyl chloroformate.

Examples of compounds having formula formula $X_2—C(O)NH_2$ are carbamic chloride and carbamic bromide.

Examples of compounds having formula $X^2—C(O)NHR^{12}$ include 4-chlorophenylcarbamic chloride, 5-bromo-1,1'-biphenyl-2-ylcarbamic chloride, quinolin-8-ylcarbamic chloride, 2-methoxyphenylcarbamic chloride, methylcarbamic chloride, cyclohexylcarbamic chloride, 2-(dimethylamino)-4-methoxyphenylcarbamic chloride, prop-2-ynylcarbamic chloride, 3-(5-(pyridin-2-yl)thien-2-yl)prop-2-ynylcarbamic chloride, and 2,6-dimethylphenylcarbamic chloride.

Examples of compounds having formula $X^2—C(O)NR^{12}R^{13}$ include dimethylcarbamic chloride, diethylcarbamic chloride, diisopropylcarbamic chloride, diallylcarbamic chloride, 4-ethoxyphenyl(pyridin-2-yl)carbamic chloride, methyl(phenyl)carbamic chloride, methyl(vinyl)carbamic chloride, diphenylcarbamic chloride, ethyl(3-(trifluoromethyl)-1,2,4-thiadiazol-5-yl)carbamic chloride, and 2-chloroprop-2-enyl(propyl)carbamic chloride.

Examples of first bases include pyridine, triethylamine, diisopropylethylamine, 4-(N,N-dimethylamino)pyridine, sodium hydroxide, potassium hydroxide, potassium tert-butoxide, sodium carbonate, sodium bicarbonate, cesium hydroxide, tetramethylammonium hydroxide, sodium hydride, potassium hydride, potassium isopropoxide, potassium isobutoxide, and mixtures thereof.

The reaction is typically conducted over about 0.5 hours to about 8 hours, at about −15° C. to about 50° C., in solvents such as tetrahydrofuran, diethylether, ethyl acetate, acetone, N,N-dimethylformamide, dimethylsulfoxide, diethylsulfoxide, 1,2-dimethoxyethane, dichloromethane, chloroform, and mixtures thereof.

SCHEME 2

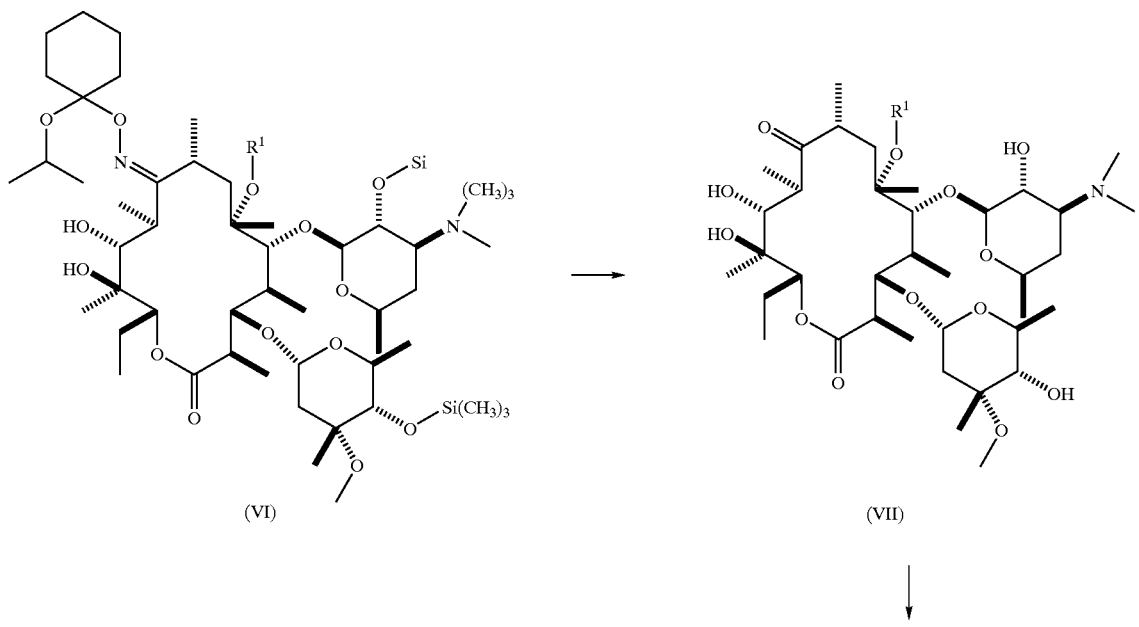

(VI)     (VII)

-continued

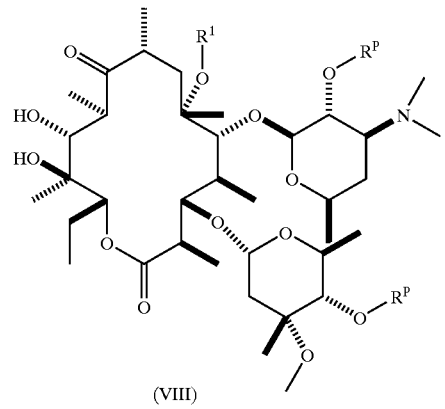

(VIII)

Compounds having formula (VI) may be converted to compounds having formula (VII) as described in U.S. Pat. No. 4,672,109, column 19–20, lines 54–64 and 1–2, respectively and U.S. Pat. No. 5,808,017, column 4, lines 21–29.

Compounds having formula (VII) may be converted to compounds having formula (VIII), in which $R^P$ is acetyl ($CH_3C(O)$—), or benzoyl ($C_6H_5C(O)$—), by reacting the former, a hydroxyl protecting group precursor and a second base, with or without 4-(N,N-dimethylamino)pyridine.

Examples of hydroxyl protecting group precursors include acetic anhydride and benzoic anhydride.

Examples of second bases include triethylamine, diisopropylethylamine, and pyridine.

The reaction is typically conducted over about 1 hour to about 24 hours, at about 25° C. to about 75° C., in solvents such as tetrahydrofuran, dimethylsulfoxide, acetonitrile, dichloromethane, chloroform, N,N-dimethylformamide, and mixtures thereof.

SCHEME 3

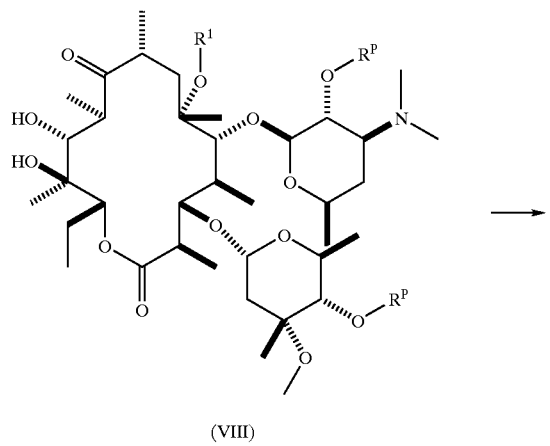

(VIII)

-continued

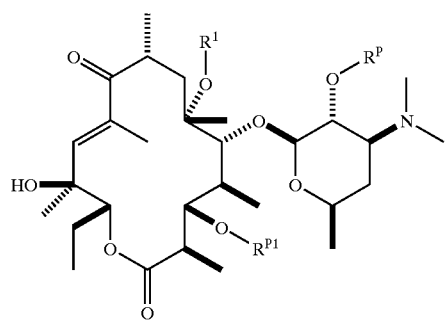

(IX)

Compounds having formula (VIII) may be converted to compounds having formula (IX), in which $R^{P1}$ is trialkylsilyl, by (a) protecting the 11,12-diol using the same reagents and under the same conditions as described in J.Org. Chem., Vol. 53, No. 10, 1988, p.2344, (b) removing the cladinose moiety from the product obtained from step (a) using the same reagents and under the same conditions described for the conversion of the compounds having formula (I)-a to the compounds having formula (II)-a in SCHEME 9, (c) silylating the product obtained from step (b) using the same reagents and under the same conditions described for the conversion of the compounds having formula (IV) to the compounds having formula (V) in SCHEME 1, and (d) dehydrating the product from step (c) using the same reagents and under the same conditions described in J.Org. Chem., Vol. 53, No. 10, 1988, p.2344.

SCHEME 4

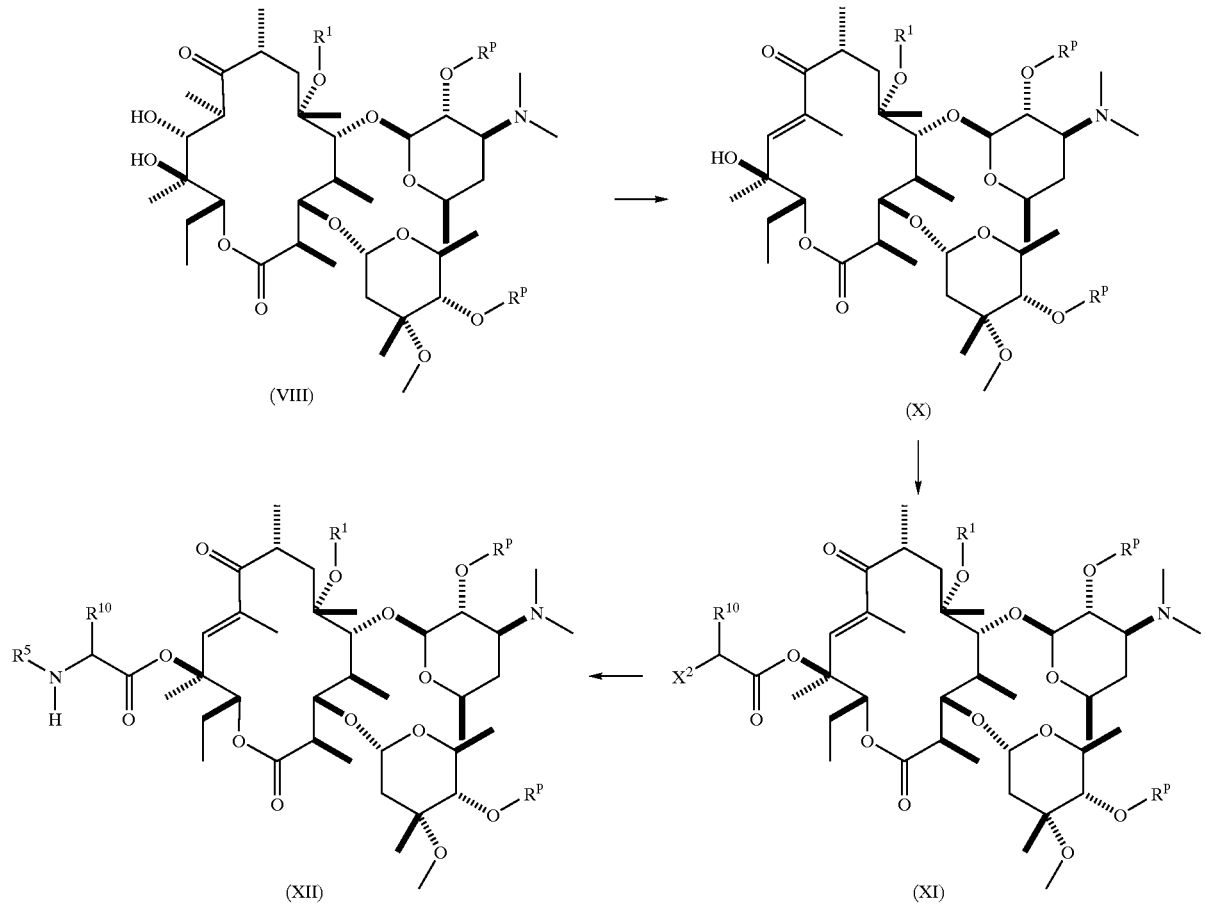

Compounds having formula (VIII) may be converted to compounds having formula (X) by (a) reacting the former and an activating agent, with or without the second base, and with or without 4-(N,N-dimethylamino)pyridine, and (b) reacting the product of step (a) and a third base.

Examples of activating agents include methanesulfonyl chloride, methanesulfonic anhydride, para-toluenesulfonyl chloride, and acetic anhydride.

Examples of third bases include sodium bis(trimethylsilyl)amide, potassium bis(trimethylsilyl)amide, lithium diisopropylamide, lithium tetramethylpiperidide, tetramethylguanidine, 1,8-diazabicyclo(5.4.0)undec-7-ene, and mixtures thereof.

Step (a) is typically conducted over about 1 hour to about 24 hours, at about −10° C. to about 40° C., in solvents such as pyridine, tetrahydrofuran, ether, dichloromethane, chloroform, dimethylsulfoxide, N,N-dimethylformamide, acetonitrile, and mixtures thereof.

Step (b) is typically conducted over about 1 hour to about 3 days, at about −78° C. to about 80° C., in solvents such as acetone, tetrahydrofuran, N,N-dimethylformamide, dioxane, 1,2-dimethoxyethane, acetonitrile, and mixtures thereof.

Compounds having formula (X) may be converted to compounds having formula (XI) by reacting the former, a compound having formula $(X^2CHR^{10}CO)_2O$, and the second base, with or without 4-(N,N-dimethylamino)pyridine.

Examples of compounds having formula $(X^2CHR^{10}CO)_2O$ include chloroacetic anhydride, 2-chloropropanoic anhydride, and 2-chlorobutanoic anhydride, bis(1-chlorobut-3-enyl)carbonate, and bis(1-chlorobut-3-ynyl)carbonate.

The reaction is typically conducted over about 1 hour to about 72 hours, at about −10° C. to about 35° C., in solvents such as dichloromethane, tetrahydrofuran, acetonitrile, chloroform, N,N-dimethylformamide, 1,2-dimethoxyethane, and mixtures thereof.

Compounds having formula (XI) may be converted to compounds having formula (XII) by reacting the former and a compound having formula $R^5NH_2$.

Examples of compounds having formula $R^5NH_2$ include allylamine, benzylamine, 2,4-dimethoxybenzylamine, ethylamine, 4-methoxybenzylamine, methylamine, propylamine, propargylamine, propylamine, 3-(5-pyridin-2-yl-thiophen-2-yl)allylamine, 3-(5-pyridin-2-yl-thiophen-2-yl)propargylamine, and (2E)-3-quinolin-3-ylprop-2-en-1-amine.

The reaction is typically conducted over about 1 hour to about 72 hours, at about −10° C. to about 50° C., in the compound having $R^5NH_2$ itself or in solvents such as N,N-dimethylformamide, pyridine, dichloromethane, chloroform, tetrahydrofuran, and mixtures thereof.

SCHEME 5

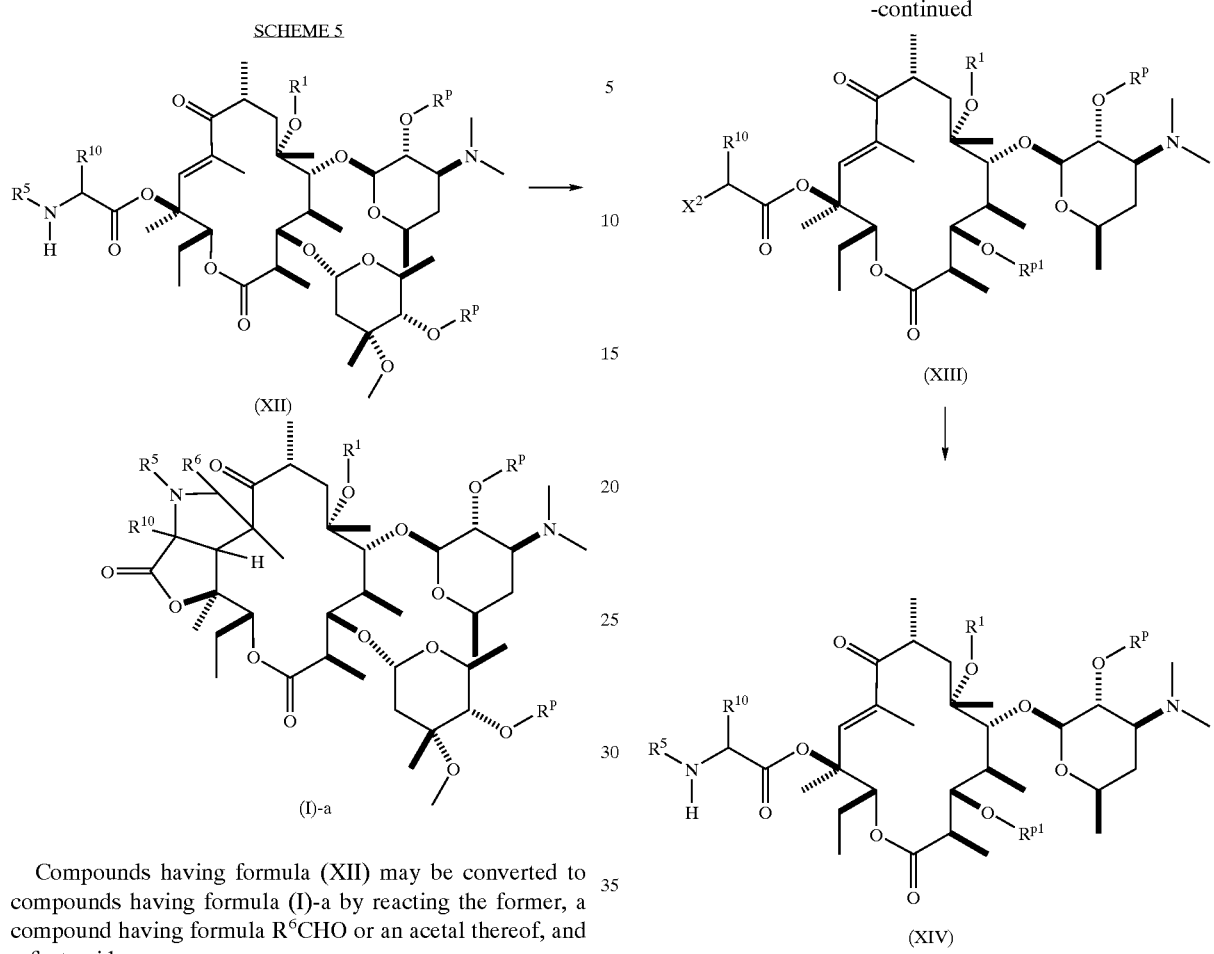

Compounds having formula (XII) may be converted to compounds having formula (I)-a by reacting the former, a compound having formula R⁶CHO or an acetal thereof, and a first acid.

Examples of compounds having formula R⁶CHO include acetaldehyde, acrolein, benzaldehyde, formaldehyde, 4-pentenaldehyde, and propionaldehyde.

Examples of first acids include hydrochloric acid, paratoluenesulfonic acid, acetic acid, formic acid, boron trifluoride, and aluminum chloride.

The reaction is typically conducted at about 25° C. to about 150° C., over about 1 hour to about 10 days, in solvents such as toluene, benzene, xylene, and mixtures thereof.

Compounds having formula (IX), in which $R^{P1}$ is trimethylsilyl or triethylsilyl, may be converted to compounds having formula (XIV) using the same reagents and under the same conditions described for the conversion of compounds having formula (X) to compounds having formula (XII) in SCHEME 4.

SCHEME 6 / SCHEME 7

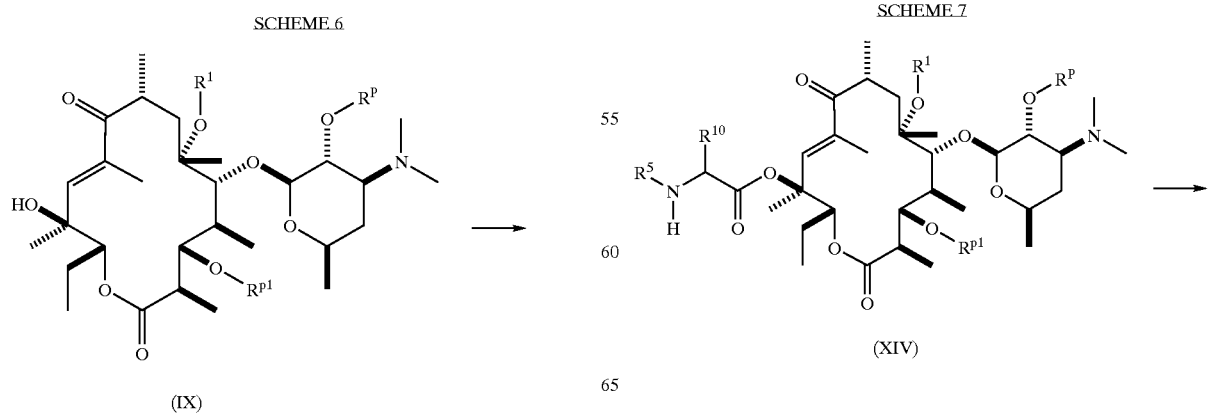

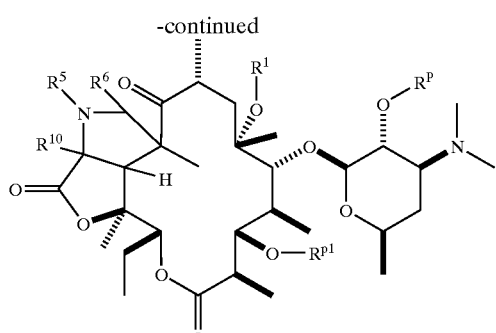

(XV)

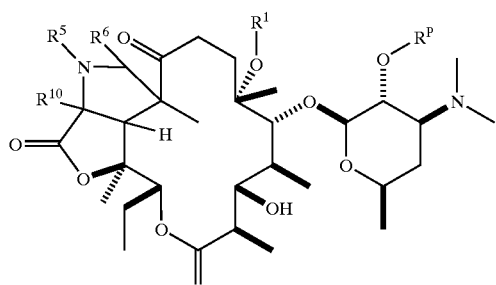

(II)-a

Compounds having formula (XIV) may be converted to compounds having formula (XV) using the same reagents and under the same conditions described for the conversion of compounds having formula (XII) to compounds having formula (I)-a in SCHEME 5.

Compounds having formula (XV) may be converted to compounds having formula (II)-a by reacting the former and a fluoride-donating agent.

Examples of fluoride-donating agents include tetrabutylammonium fluoride, tetrabutylammonium chloride/potassium fluoride monohydrate, HF.pyridine, hydrogen fluoride, and ammonium fluoride.

The reaction is typically conducted at about 25° C. to about 100° C., over about 1 hour to about 48 hours, in solvents such as benzene, toluene, tetrahydrofuran, water, acetone, and mixtures thereof.

SCHEME 8

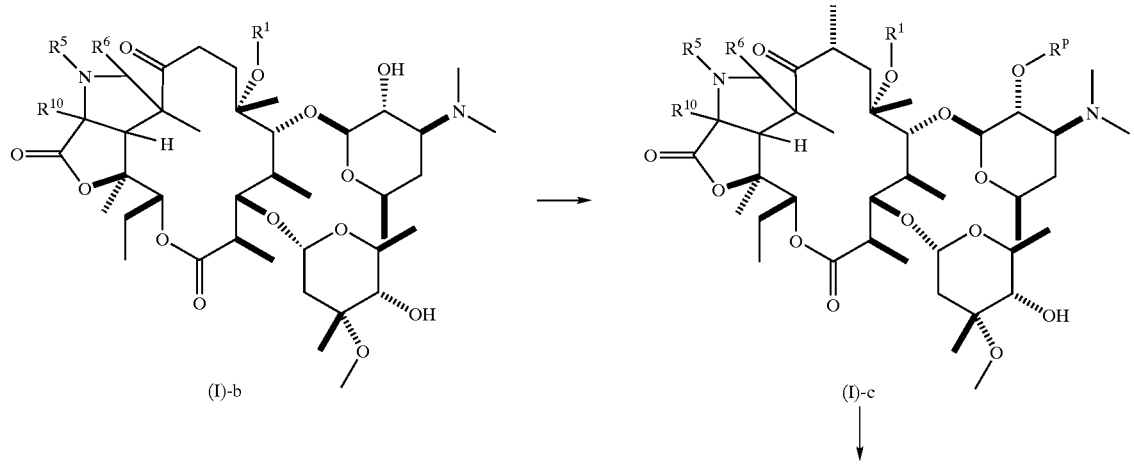

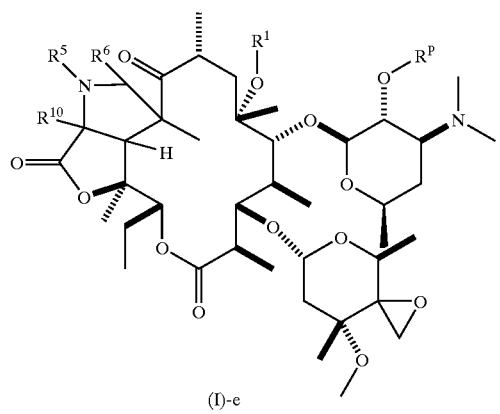

(I)-e

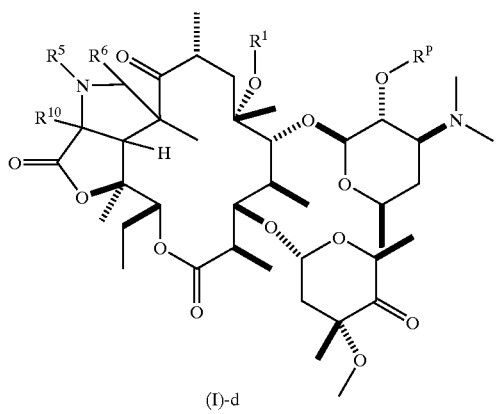

(I)-d

Compounds having formula (I)-b may be converted to compounds having formula (I)-c using the same reagents and under the same conditions described for the conversion of compounds having formula (VII) to compounds having formula (VIII) in SCHEME 2 except using only one equivalent of the hydroxyl protecting group precursor.

Compounds having formula (I)-c may be converted to compounds having formula (I)-d by reacting the former and an oxidant, with or without the second base.

Examples of oxidants include triacetoxy periodinane, N-chlorosuccinimide.dimethyl sulfide, dicyclohexyl carbodiimide.dimethyl sulfoxide.pyridinium trifluoroacetate, oxalyl chloride.dimethylsulfoxide, and sulfur trioxide.pyridine.dimethylsulfoxide.

The reaction is typically conducted at about −20° C. to about 35° C., over about 1 hour to about 72 hours, in solvents such as water, dichloromethane, acetonitrile, chloroform, tetrahydrofuran, and mixtures thereof.

Compounds having formula (I)-d may be converted to compounds having formula (I)-e by reacting the former and a sulfur ylide.

Examples of sulfur ylides include dimethyloxosulfonium methylide and dimethylsulfonium methylide.

SCHEME 9

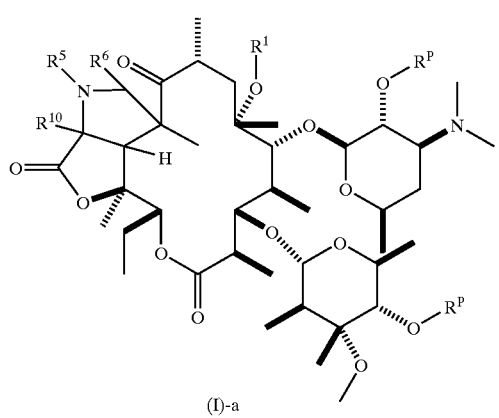

(I)-a

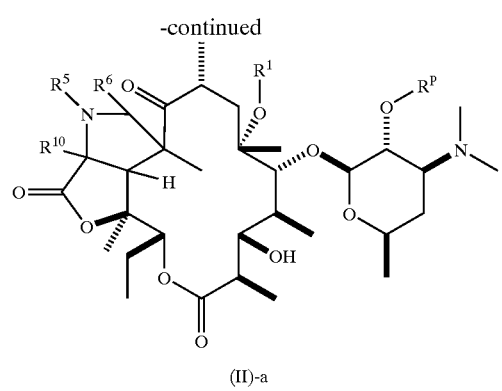

(II)-a

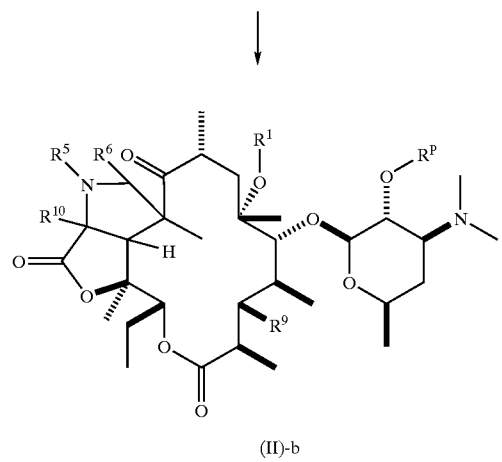

(II)-b

Compounds having formula (I)-a may be converted to compounds having formula (II)-a by reacting the former and a second acid.

Examples of second acids include hydrochloric acid, sulfuric acid, perchloric acid, chloroacetic acid, dichloroacetic acid, and trifluoroacetic acid.

The reaction is typically conducted at about −10° C. to about 70° C., over about 1 hour to about 72 hours, in solvents such as dichloromethane, tetrahydrofuran, methanol, ethanol, isopropanol, butanol, and mixtures thereof.

Compounds having formula (II)-a may be converted to compounds having formula (II)-b, in which $R^9$ is other than —OH, by reacting the former and a compound having formula $X^2$—$R^{32}$ using the same reagents and under the same conditions described for the conversion of compounds having formula (V) to compounds having formula (VI) in SCHEME 1.

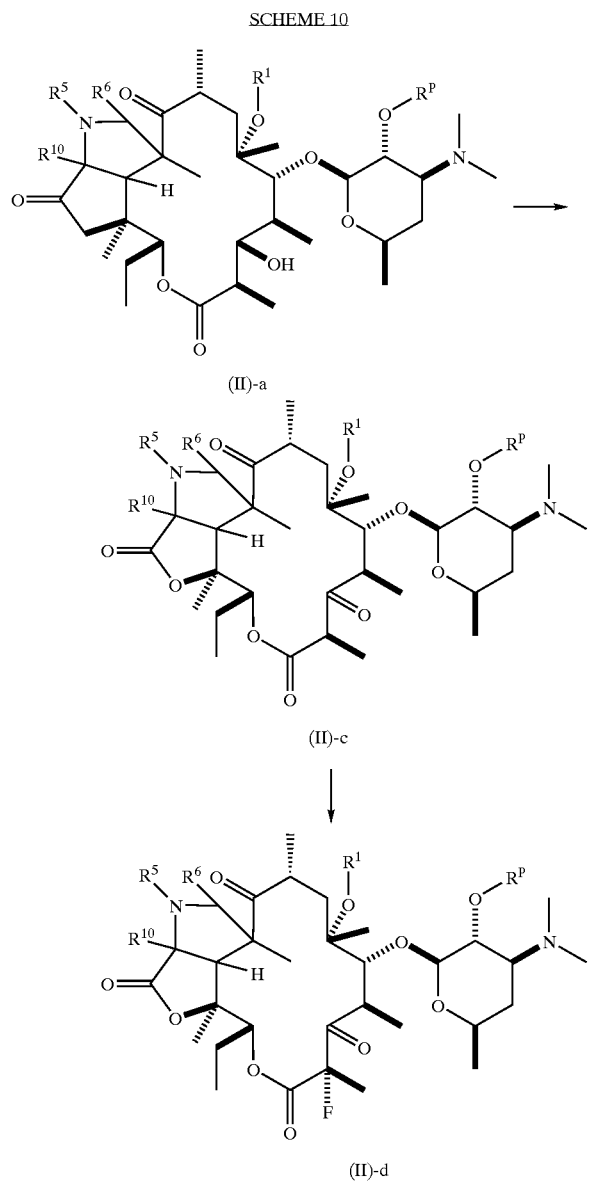

esulfonimide, N-fluoro-N-methyl-para-toluenesulfonamide, N-fluoropyridinim triflate, 1-(chloromethyl)-4-fluoro-1,4-diazoniabicyclo(2.2.2)octane bis(tetrafluoroborate) (SELECTFLUOR™), and N-fluoroperfluoropiperidine.

Examples of fourth bases include sodium hydride, potassium hydride, trimethylamine, lithium bis(triethylsilyl)amide, sodium bis(trimethylsilyl)amide, and potassium bis(trimethylsilyl)amide.

Compounds having formula (I) or formula (II), in which $R^p$ is acetyl or benzoyl, may be converted to compounds having formula (I) or formula (II), in which $R^2$ is hydrogen, by reacting the former and a deprotecting agent.

Examples of deprotecting agents include acids such as methanol, ethanol, acetic acid, and formic acid and bases such as lithium hydroxide, sodium hydroxide, potassium hydroxide, potassium carbonate, and ammonia.

The reaction is typically conducted at about 25° C. to about 70° C., over about 1 hour to about 72 hours, in solvents such as water, methanol, ethanol, and mixtures thereof.

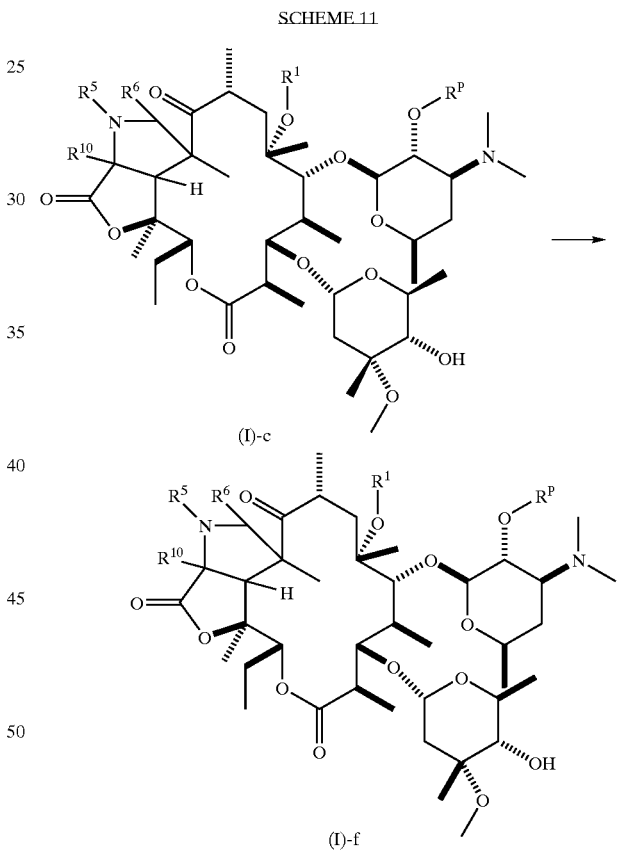

Compounds having formula (II)-a may be converted to compounds having formula (II)-c using the same reagents and under the same conditions described for the conversion of compounds of formula (I)-c to compounds of formula (I)-d in SCHEME 8.

Compounds having formula (II)-c may be converted to compounds having formula (II)-d by reacting the former and a fluorinating agent, with or without a fourth base.

Examples of fluorinating agents used without the fourth base include 10% $F_2$ in formic acid, 3,5-dichloro-1-fluoropyridinium tetrafluoroborate, 3,5-dichloro-1-fluoropyridinium triflate, and N-tetrafluoro-N-((trifluoromethyl) sulfonyl) methanesulfonamide. Examples of fluorinating agents used with the fourth base include N-fluorobenz- Compounds having formula (I)-c may be converted to compounds having formula (I)-f by (a) reacting the former, a third acid, a diazo compound, and a phosphine, and (b) reacting the product of step (a) and an alkali metal hydroxide.

Examples of third acids include benzoic acid and 4-nitrobenzoic acid.

Examples of diazo compounds include diethyl azodicarboxylate and diisopropyl azodicarboxylate.

Examples of phosphines include triphenyl phosphine and tributyl phosphine.

Examples of alkali metal hydroxides include lithium hydroxide, sodium hydroxide, and potassium hydroxide.

Step (a) is typically conducted over about 1 hour to about 8 hours, at about 0° C. to about 85° C., in solvents such as tetrahydrofuran, dichloromethane, chloroform, benzene, toluene, xylene, and mixtures thereof.

Step (b) is typically conducted over about 1 hour to about 24 hours, at about 25° C. to about 55° C., in solvents such as methanol, ethanol, isopropanol, and mixtures thereof.

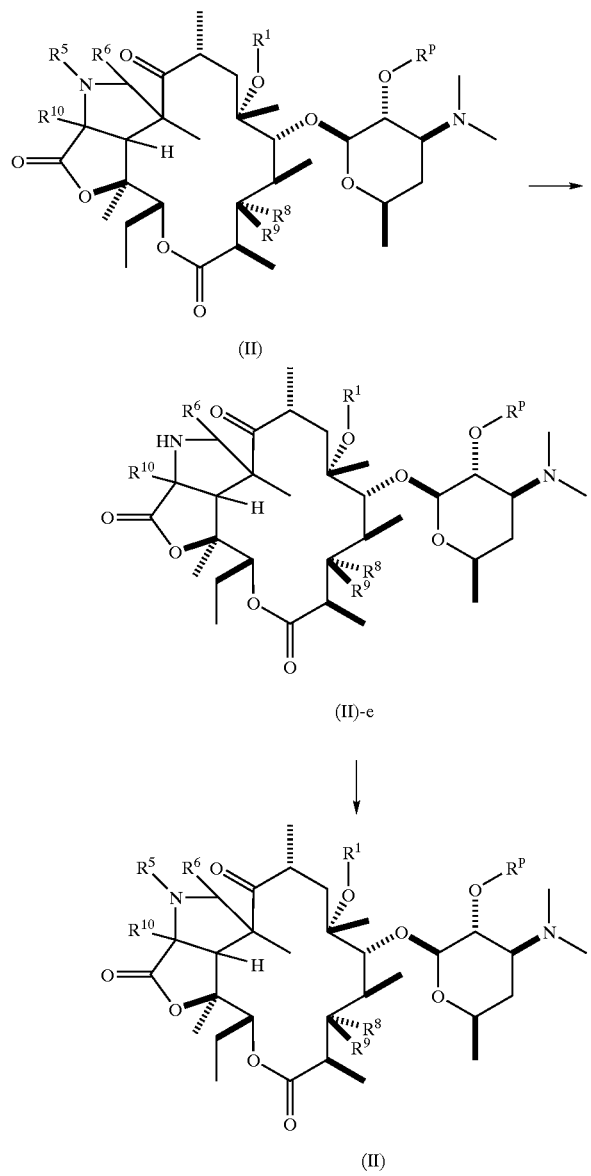

Compounds having formula (II), in which $R^5$ is prop-2-enyl, may be converted to compounds having formula (II)-e by reacting the former, a palladium reagent, and a fourth acid.

The reaction is typically conducted at about 25° C. to about 100° C., over about 2 hours to about 48 hours, in solvents such as toluene, tetrahydrofuran, dichloromethane, 1,2-dimethoxyethane, and mixtures thereof.

Examples of the palladium reagents include palladium on carbon, tetrakis palladium(0) (triphenylphosphine), and Pd(dibenzylidineacetone)diphenylphosphinobutane.

Examples of the fourth acids include methanesulfonic acid, thiobenzoic acid, and N,N-dimethylbarbituric acid.

Compounds having formula (II), in which $R^5$ is 2,4-dimethoxybenzyl, may be converted to compounds having formula (II)-e by reacting the former and trifluoroacetic acid.

The reaction is typically conducted at about 25° C. to about 75° C., over about 2 hours to about 48 hours, in solvents such as dichloromethane, chloroform, acetonitrile, tetrahydrofuran, and mixtures thereof.

Compounds having formula (II)-e may be converted to compounds having formula (II) by reacting the former and a compound having formula $X^2$—$R^5$ under the same conditions described for the conversion of compounds of formula (V) to compounds of formula (VI) in SCHEME 1.

Examples of compounds having formula $X^2$—$R^5$ include compounds having formula $X^2$—$R^{19}$, $X^2$—C(O)O$R^{19}$, $X^2$—C(O)NH$_2$, $X^2$—C(O)NH$R^{20}$, and $X^2$—C(O)N$R^{20}R^{21}$.

Examples of compounds having formula $X^2$—$R^{19}$ include bromomethane, 3-bromoprop-1-ene, 3-bromoprop-1-yne, benzyl bromide, 2-fluoroethyl bromide, 4-nitrobenzyl bromide, 4-chlorobenzyl bromide, 4-methoxybenzyl bromide, (3-bromoprop-1-enyl)benzene, 1-bromobut-2-ene, 2-(5-(3-bromoprop-1-ynyl)thien-2-yl)pyridine, 1-bromopent-2-ene, 2-(3-bromoprop-1-enyl)naphthalene, 5-(3-bromoprop-1-ynyl)-2-thien-2-ylpyridine, 2-(3-bromoprop-1-ynyl)pyridine, 3-((1E)-3-bromoprop-1-enyl)quinoline, 2-(5-(3-bromoprop-1-ynyl)isoxazol-3-yl)pyridine, and 2-(5-(3-bromoprop-1-ynyl)thien-2-yl)pyrimidine.

Examples of compounds having formula $X^2$—C(O)O$R^{19}$ include ethyl chloroformate, methyl chloroformate, phenyl chloroformate, propargyl chloroformate, allyl chloroformate, 2-bromoethyl chloroformate, 1-chloroethyl chloroformate, 3-chloropropyl formate, 4-chlorobutyl formate, 3-butenyl chloroformate, 2-methoxyphenyl chloroformate, para-toluene chloroformate, and 4-methoxyphenyl chloroformate.

Examples of compounds having formula formula $X^2$—C(O)NH$_2$ are carbamic chloride and carbamic bromide.

Examples of compounds having formula $X^2$—C(O)NH$R^{20}$ include 4-chlorophenylcarbamic chloride, 5-bromo-1,1'-biphenyl-2-ylcarbamic chloride, quinolin-8-ylcarbamic chloride, 2-methoxyphenylcarbamic chloride, methylcarbamic chloride, cyclohexylcarbamic chloride, 2-(dimethylamino)-4-methoxyphenylcarbamic chloride , prop-2-ynylcarbamic chloride, 3-(5-(pyridin-2-yl)thien-2-yl)prop-2-ynylcarbamic chloride, and 2,6-dimethylphenylcarbamic chloride.

Examples of compounds having formula $X^2$—C(O)N$R^{20}R^{21}$ include dimethylcarbamic chloride, diethylcarbamic chloride, diisopropylcarbamic chloride, diallylcarbamic chloride, 4-ethoxyphenyl(pyridin-2-yl)carbamic chloride, methyl(phenyl)carbamic chloride, methyl(vinyl)carbamic chloride, diphenylcarbamic chloride, ethyl(3-(trifluoromethyl)-1,2,4-thiadiazol-5-yl)carbamic chloride, and 2-chloroprop-2-enyl(propyl)carbamic chloride.

Compounds having formula (II)-e may also be converted to compounds having formula (II), in which $R^5$ is —$R^{19}$, by reacting the former, a compound having formula $R^5$CHO or the corresponding acetal, and a reducing agent, with or without the first acid.

Examples of reducing agents include sodium borohydride, sodium cyanoborohydride, sodium triacetoxyborohydride, zinc/hydrochloric acid, iron pentacarbonyl/alcoholic potassium hydroxide, borane.pyridine, and formic acid.

Examples of compounds having formula $R^5CHO$ include formaldehyde, acrolein, 4-pentenaldehyde, acetaldehyde, propionaldehyde, and benzaldehyde.

The reaction is typically conducted at about −10° C. to about 150° C., over about 1 hour to about 10 days, in solvents such as tetrahydrofuran, dichloromethane, toluene, benzene, xylene, N,N-dimethylformamide, and mixtures thereof.

The following examples illustrate methods by which certain preferred first embodiments of the invention may be prepared.

EXAMPLE 1

Compound having Formula (VIII): $R^1$ is —$CH_2C\equiv C$—H; $R^P$ is —C(O)(phenyl)

This example was prepared from erythromycin A (obtained from Abbott Laboratories) as described in SCHEME 1 and SCHEME 2. $^{13}C$ NMR (CDCl$_3$) δ 219.9, 174.9, 166.1, 165.4, 133.4, 132.6, 130.8, 129.8, 129.6, 128.4, 128.2, 99.9, 95.9, 81.1, 80.4, 80.1, 78.8, 78.2, 76.6, 74.4, 73.8, 72.9, 72.6, 68.7, 67.5, 63.6, 51.6, 49.6, 45.2, 44.6, 40.9, 38.0, 37.8, 37.4, 35.4, 31.6, 26.9, 21.3, 21.1, 20.2, 18.5, 18.2, 16.2, 16.1, 12.3, 10.5, 9.5.

EXAMPLE 2

Compound having Formula (X): $R^1$ is —$CH_2C\equiv C$—H, $R^P$ is —C(O)(phenyl)

A solution of EXAMPLE 1 (2.605 g) in pyridine (13 mL) at 10° C. was treated with methansulfonic anhydride (1.2 g), stirred at 25° C. for 20 hours, and concentrated. The concentrate was dissolved in dichloromethane (50 mL), washed with saturated aqueous NaHCO$_3$, and dried (Na$_2$SO$_4$), filtered, and concentrated. A solution of the concentrate and 1,8-diazabicyclo(5.4.0)undec-7-ene (0.60 mL) in acetone (15 mL) was stirred for 20 hours and concentrated; and the concentrate was flash chromatographed on silica gel with 15–40% acetone/hexane. $^1H$ NMR (CDCl$_3$) δ 8.06–7.98 (m, 4H), 7.63–7.38 (m, 6H), 6.48 (s, 1H), 5.05 (dd, J=10.5, 7.4 Hz, 1H), 4.97–4.87 (m, 3H), 4.82 (d, J=7.2 Hz, 1H), 4.51 (m, 1H), 4.23 (m, 2H), 3.94 (d, J=7.8 Hz, 1H), 3.82 (m, 1H), 3.63 (d, J=6.6 Hz, 1H), 3.48 (s, 3H), 3.34 (m, 1H), 2.93 (m, 1H), 2.75 (m, 1H), 2.58 (d, J=15.3 Hz, 1H), 2.36 (t, J=2.1 Hz, 1H), 2.31 (s, 6H), 2.00 (d, J=0.9 Hz, 2H), 1.91–1.70 (m, 6H), 1.54 (s, 3H), 1.51 (m, 2H), 1.43 (m, 4H), 1.28–1.16 (m, 13H), 1.00 (d, J=6 Hz, 3H), 0.86 (t, J=7.2 Hz, 3H), 0.75 (d, J=7.5 Hz, 3H).

EXAMPLE 3A

Compound having Formula (XI): $R^1$ is —$CH_2C\equiv C$—H, $R^{10}$ is Hydrogen, $R^P$ is —C(O)(phenyl)

A solution of EXAMPLE 2 (2.19 g), triethylamine (300 μL), and 4-(N,N-dimethylamino)pyridine (20 mg) in dichloromethane (50 mL) at 0° C. was treated with chloroacetic anhydride (840 mg), stirred at 25° C. for 30 minutes, washed with saturated aqueous NaHCO$_3$, and dried (Na$_2$SO$_4$), filtered, and concentrated; and the concentrate was flash chromatographed on silica gel with 15–50% acetone/hexane. $^1H$ NMR (CDCl$_3$) δ 8.07–7.98 (m, 4H), 7.63–7.38 (m, 6H), 6.60 (s, 1H), 5.75 (dd, J=10.2, 3.3 Hz, 1H), 5.03 (m, 2H), 4.94 (d, J=9.9 Hz, 1H), 4.82 (d, J=7.8 Hz, 1H), 4.51 (m, 1H), 4.22 (m, 2H), 3.96 (s, 2H), 3.81 (m, 2H), 3.62 (d, J=6.6 Hz, 1H), 3.46 (s, 3H), 3.41 (m, 1H), 2.91 (m, 1H), 2.79 (m, 1H), 2.45 (d, J=14.7 Hz, 1H), 2.38 (t, J =2.1 Hz, 1H), 2.30 (s, 6H), 1.83 (s, 2H), 1.75 (m, 4H), 1.54 (s, 3H), 1.50 (m, 4H), 1.36 (s, 3H), 1.24 (m, 11H), 1.15 (d, J=6.3 Hz, 3H), 1.00 (m, 2H), 0.84 (t, J=7.5 Hz, 3H), 0.75 (d, J=7.5 Hz, 3H).

EXAMPLE 3B

Compound having Formula (XII): $R^1$ is —$CH_2C\equiv C$—H, $R^5$ is Methyl, $R^{10}$ is Hydrogen, $R^P$ is —C(O) (phenyl)

A solution of EXAMPLE 3A (2.38 g) and 2M methylamine in THF (3.5 mL) in DMF (20 mL) at 25° C. was stirred for 18 hours, treated with more 2M methylamine in tetrahydrofuran (3 mL), stirred for 48 hours, and concentrated; and the concentrate was flash chromatographed on silica gel with 0.25% concentrated ammonium hydroxide/ (95:5 dichloromethane/methanol). $^{13}C$ NMR (CDCl$_3$) δ 205.8, 174.0, 169.8, 166.2, 165.2, 140.2, 137.2, 133.4, 132.5, 130.7, 129.8, 129.7, 128.4, 128.1, 100.5, 96.5, 81.9, 81.0, 80.4, 79.7, 79.1, 78.9, 76.6, 75.6, 73.4, 72.9, 72.3, 67.9, 63.6, 63.5, 51.9, 51.8, 49.7, 45.1, 40.8, 39.6, 39.1, 36.0, 35.6, 32.0, 23.6, 21.7, 21.25, 21.2, 19.0, 18.5, 17.2, 16.1, 13.0, 10.1.

EXAMPLE 3C

Compound having Formula (I)-a: $R^1$ is —$CH_2C\equiv C$—H, $R^5$ is Methyl, $R^{10}$ is Hydrogen, $R^P$ is —C(O) (phenyl)

A solution of EXAMPLE 3B (1.57 g), 37% aqueous formaldehyde (115 μL), and acetic acid (2 drops) in toluene (40 mL) was stirred for 30 minutes at 25° C. and at 110° C. for 1.5 hours under a Dean-Stark trap, and concentrated; and the concentrate was flash chromatographed on silica gel with 10–25% acetone/hexane. $^{13}C$ NMR (CDCl$_3$) δ 217.4, 178.1, 176.8, 166.2, 165.3, 133.3, 132.6, 130.7, 129.9, 129.8, 129.6, 128.4, 128.2, 100.8, 95.4, 86.4, 83.0, 80.7, 79.6, 79.0, 78.5, 76.5, 74.9, 70.3, 72.2, 67.8, 67.2, 66.2, 63.7, 63.4, 56.5, 53.0, 52.0, 49.7, 45.1, 42.0, 41.3, 40.9, 39.9, 37.8, 35.0, 32.2, 23.9, 23.6, 21.5, 21.3, 21.2, 19.6, 18.4, 16.2, 15.2, 10.5, 9.5.

EXAMPLE 3D (2aR,4aS,6R,8S,9R,10S,11S,12R,15R,15aS,15bS)-15-ethyl-3,4a,6,8,10,12,15a-heptamethyl-2,5,13-trioxo-8-(prop-2-ynyloxy)-9-((3,4,6-trideoxy-3-(dimethylamino)-β-D-xylo-hexopyranosyl)oxy) hexadecahydro-2H-1,14-dioxa-3-azacyclotetradeca (1,2,3-cd)pentalen-11-yl 4-O-benzoyl-2,6-dideoxy-3-C-methyl-3-O-methyl-α-L-ribo-hexopyranoside A solution of EXAMPLE 3C (60 mg) in methanol (10 mL) was refluxed for 24 hours and concentrated; and the concentrate was flash chromatographed on silica gel with 84:15:1 dichloromethane/methanol/concentrated ammonium hydroxide. $^{13}C$ NMR (CDCl$_3$) δ 217.0, 178.2, 176.9, 166.1, 133.3, 130.0, 129.6, 128.3, 102.8, 95.4, 86.5, 83.0, 80.7, 79.6, 79.1, 78.8, 76.7, 75.0, 72.8, 71.0, 68.1, 67.2, 66.2, 65.4, 63.4, 56.6, 53.0, 52.1, 49.6, 45.3, 42.0, 41.4, 40.5, 40.4, 37.7, 34.9, 29.3, 23.9, 23.6, 21.5, 21.4, 21.2, 19.7, 18.3, 16.3, 15.1, 10.5, 9.3.

EXAMPLE 3E

A solution of EXAMPLE 3C (815 mg) in dichloromethane (20 mL) and trifluoroacetic acid (1 mL) at 25° C. was stirred for one hour, treated with more trifluoroacetic acid (1 mL), stirred for another hour, washed with saturated aqueous NaHCO$_3$, and dried (Na$_2$SO$_4$), filtered, and concentrated; and the concentrate was flash chromatographed on silica gel with 10–40% acetone/hexane. $^1$H NMR (CDCl$_3$) δ 8.05 (m, 2H), 7.55 (m, 1H), 7.43 (m, 2H), 5.05 (dd, J=10.5, 7.8 Hz, 1H), 4.75 (d, J=7.8 Hz, 1H), 4.59 (dd, J=10.5, 2.1 Hz, 1H), 4.00 (m, 2H), 3.71 (d, J=2.7 Hz, 1H), 3.61–3.45 (m, 4H), 2.91 (m, 3H), 2.70 (m, 2H), 2.66 (s, 3H), 2.40 (t, J=2.4 Hz, 1H), 2.32 (m, 1H), 2.28 (s, 6H), 1.77 (m, 2H), 1.67 (s, 3H), 1.60 (m, 2H), 1.54 (s, 3H), 1.51 (m, 2H), 1.44 (d, J=3.3 Hz, 3H), 1.28 (d, J=6.0 Hz, 3H), 1.16 (d, 3H, J=6.9 Hz), 0.92 (d, J=6.9 Hz, 3H), 0.81 (d, J=7.2 Hz 3H), 0.79 (t, J=7.5 Hz, 3H).

EXAMPLE 3F

A solution of EXAMPLE 3E (612 mg) and triacetoxy periodinane (430 mg) in dichloromethane (10 mL) at 25° C. was stirred for 1 hour, diluted with dichloromethane, washed sequentially with saturated aqueous NaHCO$_3$, saturated aqueous sodium thiosulfate, and brine, and dried (Na$_2$SO$_4$), filtered, and concentrated. $^1$H NMR (CDCl$_3$) δ 8.02 (m, 2H), 7.56 (m, 1H), 7.44 (m, 2H), 5.03 (dd, J=10.5, 7.5 Hz, 1H), 4.57 (dd, J=9.9, 2.4 Hz, 1H), 4.51 (d, J=7.5,Hz, 1H), 4.20 (d, J=7.5 Hz, 1H), 3.76 (q, J=7.2 Hz, 1H), 3.70 (t, J=2.1 Hz, 2H), 3.62 (m, 1H), 3.53 (d, J=8.1 Hz, 1H), 3.45 (d, J=10.5 Hz, 1H), 3.04–2.80 (m, 4H), 2.68 (d, J=10.5 Hz, 1H), 2.64 (s, 3H), 2.36 (t, J=2.1 Hz, 1H), 2.27 (s, 6H), 2.17 (dd, J=15, 9 Hz, 1H), 1.80 (m, 2H), 1.70 (s, 3H), 1.60 (m, 3H), 1.49 (s, 3H), 1.47 (s, 3H), 1.33 (d, 3H, J=7.2 Hz), 1.30 (d, J=5.7 Hz, 3H), 1.00 (d, J=3.3 Hz, 3H), 0.98 (d, J=3.3 Hz, 3H), 0.80 (t, J=7.2 Hz, 3H).

EXAMPLE 3G (2aR,4aS,6R,8S,9R,10R,12R,15R,15aS,15bS)-15-ethyl-3,4a,6,8,10,12,15a-heptamethyl-2,5,11,13-tetraoxo-8-(prop-2-ynyloxy)hexadecahydro-2H-1,14-dioxa-3-azacyclotetradeca-(1,2,3-cd)pentalen-9-yl 3,4,6-trideoxy-3-(dimethylamino)-β-D-xylo-hexopyranoside A solution of EXAMPLE 3F (60 mg) in methanol (5 mL) was heated at 60° C. for 36 hours and concentrated; and the concentrate was flash chromatographed on silica gel with 84:15:1 of dichloromethane/methanol/concentrated ammonium hydroxide. $^{13}$C NMR (CDCl$_3$) δ 216.9, 205.8, 176.5, 170.4, 104.0, 85.7, 83.9, 80.4, 80.2, 78.8, 77.4, 74.4, 70.4, 69.5, 67.5, 66.1, 65.8, 56.6, 52.7, 51.4, 50.7, 48.5, 41.9, 40.3, 39.2, 36.6, 28.5, 22.3, 21.8, 21.2, 19.6, 16.9, 15.8, 14.3, 10.4.

EXAMPLE 4A

A solution of EXAMPLE 3F (520 mg), triethylamine (5 mL), 2-(5-bromothien-2-yl)pyridine (250 mg), tris(dibenzylideneacetone)dipalladium(0) (55 mg), bis(1,2-diphenylphosphino)ethane (48 mg), and copper(I) iodide (4 mg) in acetonitrile (10 mL) at 80° C. was stirred for 3 hours, cooled to room temperature, and concentrated; and the concentrate was flash chromatographed on silica gel with 10–40% acetone/hexane. $^1$H NMR (CDCl$_3$) δ 8.56 (m, 1H), 8.03 (m, 2H), 7.73–7.54 (m, 3H), 7.47–7.41 (m, 3H), 7.17 (m, 1H), 7.13 (d, J=4.2 Hz, 1H), 5.05 (dd, J=10.5, 7.2 Hz, 1H), 4.59 (dd, J=10.5, 2.7 Hz, 1H), 4.53 (d, J=7.8 Hz, 1H), 4.29 (d, J=8.1 Hz, 1H), 3.95 (s, 2H), 3.80 (q, J=6.9 Hz, 1H), 3.62 (m, 1H), 3.48 (d, J=8.1 Hz, 1H), 3.41 (d, J=10.2 Hz, 1H), 3.06 (quintet, J=7.5 Hz, 1H), 2.91 (d, J=8.1 Hz, 1H), 2.95–2.80 (m, 2H), 2.67 (d, J=10.5 Hz, 1H), 2.52 (s, 3H), 2.28 (s, 6H), 2.23 (m, 1H), 1.80 (m, 2H), 1.72 (s, 3H), 1.60 (m, 1H), 1.54 (s, 3H), 1.50 (m, 2H), 1.48 (s, 3H), 1.35 (d, J=6.9 Hz, 3H), 1.31 (d, J=5.7 Hz, 3H), 1.02 (d, J=2.7 Hz, 3H), 1.00 (d, J=3.3 Hz, 3H), 0.81 (t, J=7.5 Hz, 3H).

EXAMPLE 4B (2aR,4aS,6R,8S,9R,10R,12R,15R,15aS,15bS)-15-ethyl-3,4a,6,8,10,12,15a-heptamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside A solution of EXAMPLE 4A (445 mg) in methanol (20 mL) was refluxed for 20 hours and concentrated; and the concentrate was flash chromatographed on silica gel with 90:10:0.5 dichloromethane/methanol/concentrated ammonium hydroxide. 13C NMR (CDCl$_3$) δ 217.1, 205.9, 176.6, 170.6, 151.7, 149.7, 146.0, 136.7, 132.6, 124.5, 124.1, 122.4, 118.7, 104.1, 94.4, 85.8, 80.3, 80.2, 79.7, 78.5, 70.4, 69.6, 67.4, 66.1, 65.8, 56.6, 52.7, 52.4, 50.6, 48.6, 42.2, 40.3, 39.6, 37.0, 28.4, 22.7, 22.5, 21.7, 21.3, 19.7, 16.9, 15.9, 14.3, 10.4.

EXAMPLE 5

(2aR,4aS,6R,8S,9R,10R,12R,15R,15aS,15bS)-3-allyl-15-ethyl-8-methoxy-4a,6,8,10,12,15a-hexamethyl-2,5,13-trioxo-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside This example was prepared as described in SCHEME 3.

EXAMPLE 6A

A solution of EXAMPLE 5 (1.13 g), triethylamine (0.5 mL), and 4-(N,N-dimethylamino)pyridine (10 mg) in dichloromethane (80 mL) at 0° C. was treated with chioroacetic anhydride (1.18 g), stirred at 25° C. for 3 hours, washed with saturated aqueous NaHCO$_3$, and dried (Na$_2$SO$_4$), filtered, and concentrated; and the concentrate was flash chromatographed on silica gel with 30% acetone/hexane.

EXAMPLE 6B

A solution of EXAMPLE 6A (4.08 g) and allylamine (2.5 mL) at 25° C. was stirred for 20 hours and concentrated; and the concentrate was flash chromatographed on silica gel with 89:10:1 dichloromethane/methanol/concentrated ammonium hydroxide.

EXAMPLE 6C

A solution of EXAMPLE 6B (2.77 g), 37% aqueous formaldehyde (160 μL) and acetic acid (10 drops) in toluene (80 mL) was stirred for 30 minutes at 25° C. and at 110° C. for 1.5 hours under a Dean-Stark trap, and concentrated; and the concentrate was flash chromatographed on silica gel with 10–50% acetone/hexane.

A solution of the product from the preceeding paragraph (2.48 g) in THF (50 mL) at 25° C. was treated with 1M tetrabutylammonium fluoride in THF (3.3 mL), stirred for 2 hours, and concentrated. The concentrate was dissolved in dichloromethane (60 mL), treated with triacetoxy periodinane (3.56 g), stirred at 25° C. for 2 hours, diluted with dichloromethane, washed sequentially with saturated aqueous $NaHCO_3$, saturated aqueous sodium thiosulfate, and brine, and dried ($Na_2SO_4$), filtered and concentrated; and the concentrate was flash chromatographed on silica gel with 1:1 of acetone/hexane.

EXAMPLE 6D

A solution of EXAMPLE 6C (100 mg), tetrakis palladium (0) (triphenylphosphine) (16 mg), and N,N-dimethylbarbituric acid (65 mg) in dichloromethane (1 mL) at 35° C. was stirred for 5 hours, treated with dichloromethane (70 mL), washed with saturated aqueous $NaHCO_3$ and brine, and dried ($Na_2SO_4$), filtered and concentrated; and the concentrate was flash chromatographed on silica gel with 29.5:70:0.5 acetone/hexane/triethylamine.

EXAMPLE 6E (2aR,4aS,6R,8S,9R,10R,12R,15R,15aS,15bS)-15-ethyl-8-methoxy-4a,6,8,10,12,15a-hexamethyl-2,5,11,13-tetraoxohexa-decahydro-2H-1,14-dioxa-3-azacyclotetradeca(1,2,3-cd)-pentalen-9-yl 3,4,6-trideoxy-3-(dimethylamino)-β-D-xylo-hexopyranoside A solution of EXAMPLE 6D in methanol (1 mL) at 25° C. was stirred for 24 hours and concentrated; and the concentrate was flash chromatographed on silica gel with 94.5:5:0.5 dichloromethane/methanol/concentrated ammonium hydroxide. $^{13}C$ NMR ($CDCl_3$) δ 217.2, 205.5, 177.0, 170.3, 104.0, 86.4, 79.3, 78.5, 78.1, 70.4, 69.5, 65.7, 60.3, 59.2, 56.6, 52.6, 51.1, 50.6, 48.6, 40.8, 40.2, 36.7, 28.4, 21.6, 21.4, 21.2, 21.0, 19.8, 16.9, 16.1, 14.4, 10.3.

EXAMPLE 7A

A solution of EXAMPLE 6A (480 mg) and 2M methylamine in THF (1.5 mL) in N,N-dimethylformamide (3 mL) was stirred at 25° C. for 6 hours and concentrated.

EXAMPLE 7B

A solution of EXAMPLE 7A (76 mg), 37% aqueous formaldehyde (7.2 μL), and acetic acid (one drop) in toluene (20 mL) was stirred for 30 minutes at 25° C. and at 110° C. for 1.5 hours under a Dean-Stark trap, and concentrated; and the concentrate was flash chromatographed on silica gel with 10–50% acetone/hexane.

EXAMPLE 7C

A solution of EXAMPLE 7B (283 mg) in THF (5 mL) at 25° C. was treated with 1M tetrabutylammonium fluoride in THF (0.4 mL), stirred for 1.5 hours, and concentrated. A solution of the concentrate (260 mg) in dichloromethane (8 mL) at 25° C. was treated with triacetoxy periodinane (190 mg), stirred for 1 hour, diluted with dichloromethane, washed with saturated aqueous $NaHCO_3$, saturated aqueous sodium thiosulfate, and brine, and dried ($Na_2SO_4$), filtered and concentrated; and the concentrate was flash chromatographed on silica gel with 1:1 acetone/hexane.

EXAMPLE 7D (2aR,4aS,6R,8S,9R,10R,12R,15R,15aS,15bS)-15-ethyl-8-methoxy-3,4a,6,8,10,12,15a-heptamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside A solution of EXAMPLE 7C (225 mg) in methanol (5 mL) at 55° C. was stirred for 3 hours and concentrated; and the concentrate was flash chromatographed on silica gel with 89/10/1 dichloromethane/methanol/concentrated ammonium hydroxide.

The foregoing is merely illustrative of the invention and is not intended to limit the same. Variations and changes which are obvious to one skilled in the art are intended to be within the scope and nature of the invention as defined in the claims.

What is claimed is:
1. A compound having formula (I)

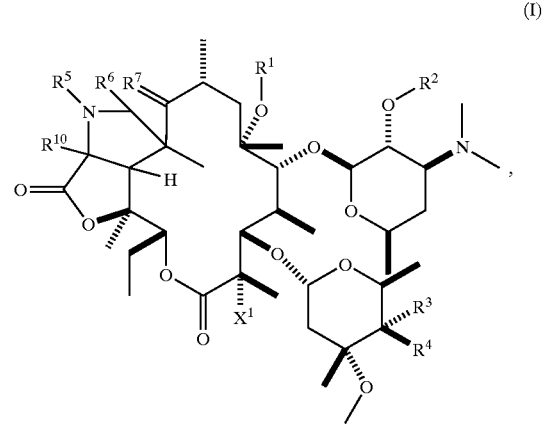

or formula (II),

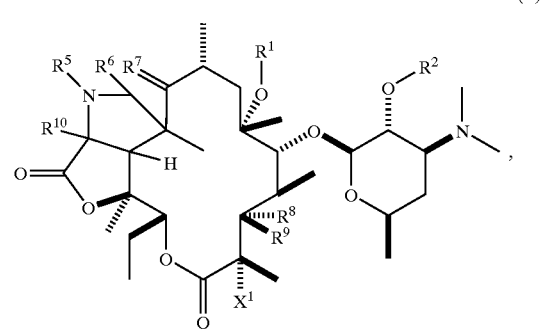

or a salt, prodrug, or salt of a prodrug thereof, in which
$R^1$ is hydrogen, $—R^{11}$, $—C(O)OR^{11}$, $—C(O)NH_2$, $—C(O)NHR^{12}$, $—C(O)NR^{12}R^{13}$, $—CH_2R^{14}$, $—C(O)OCH_2R^{14}$, $—C(O)NHCH_2R^{14}$, or $—C(O)N(CH_2R^{14})_2$;

$R^2$ is hydrogen or $R^P$, in which $R^P$ is a hydroxyl protecting moiety;

one of $R^3$ or $R^4$ is hydrogen and the other is —OH, —$OR^P$, —$OR^{15}$, —$OC(O)R^{15}$, —$OC(O)OR^{15}$, —$OC(O)NH_2$, —$OC(O)NHR^{16}$, —$OC(O)NR^{16}R^{17}$, —$OCH_2R^{18}$, or —$OC(O)OCH_2R^{18}$; or $R^3$ and $R^4$ together are =O or —$CH_2O$—;

$R^5$ is hydrogen, —$R^{19}$, —$C(O)OR^{19}$, —$C(O)NH_2$, —$C(O)NHR^{20}$, —$C(O)NR^{20}R^{21}$, —$CH_2R^{22}$, —$C(O)OCH_2R^{22}$, —$C(O)NHCH_2R^{22}$, or —$OC(O)N(CH_2R^{22})_2$;

$R^6$ and $R^{10}$ are independently hydrogen or —$R^{23}$;

$R^7$ is =O, =NOH, =$NOR^P$, =$NOR^{24}$, or =$NO(CH_2)R^{25}$;

one of $R^8$ and $R^9$ is hydrogen, and the other is —OH or —$OR^{32}$; or $R^8$ and $R^9$ together are =O;

$R^{11}$, $R^{15}$, $R^{19}$, $R^{24}$, and $R^{26}$ are independently alkyl, —($CH_2$)alkenyl, —($CH_2$)alkynyl, alkyl substituted with one or two or three substituents independently selected from the group consisting of cycloalkyl, halo, aryl, heteroaryl, and heterocyclyl, —($CH_2$)alkenyl substituted with one or two or three substituents independently selected from the group consisting of cycloalkyl, halo, aryl, heteroaryl, and heterocyclyl, or —($CH_2$)alkynyl substituted with one or two or three substituents independently selected from the group consisting of cycloalkyl, aryl, heteroaryl, and heterocyclyl;

$R^{12}$, $R^{13}$, $R^{16}$, $R^{17}$, $R^{20}$, $R^{21}$, $R^{27}$, and $R^{28}$ are independently alkyl, cycloalkyl, —($CH_2$)alkenyl, —($CH_2$)alkynyl, aryl, heteroaryl, heterocyclyl, alkyl substituted with one substituent selected from the group consisting of cycloalkyl, aryl, heteroaryl, heterocyclyl, —$NH_2$, —$NHR^{30}$, and —$NR^{30}R^{31}$, —($CH_2$)alkenyl substituted with one substituent selected from the group consisting of cycloalkyl, aryl, heteroaryl, heterocyclyl, —$NH_2$, —$NHR^{30}$, and —$NR^{30}R^{31}$, or —($CH_2$)alkynyl substituted with one substituent selected from the group consisting of cycloalkyl, aryl, heteroaryl, heterocyclyl, —$NH_2$, —$NHR^{30}$, and —$NR^{30}R^{31}$; or $R^{12}$ and $R^{13}$ together, $R^{16}$ and $R^{17}$ together, $R^{20}$ and $R^{21}$ together, or $R^{27}$ and $R^{28}$ together are independently $C_3$–$C_6$-alkylene, $C_5$–$C_6$-alkylene interrupted with one moiety selected from the group consisting of —O—, —NH—, —N(alkyl)-, —S—, —S(O)—, and —$SO_2$—, $C_3$–$C_6$-alkylene substituted with one substituent selected from the group consisting of —OH, —O(alkyl), =O, —$NH_2$, —$NHR^{30}$, and —$NR^{30}R^{31}$, or $C_5$–$C_6$-alkylene interrupted with one moiety selected from the group consisting of —O—, —NH—, —N(alkyl)-, —S—, —S(O)—, and —$SO_2$— and substituted with one substituent selected from the group consisting of —OH, —O(alkyl), =O, —$NH_2$, —$NHR^{30}$, and —$NR^{30}R^{31}$;

$R^{14}$, $R^{18}$, $R^{22}$, $R^{25}$, and $R^{29}$ are independently alkyl interrupted with one or two or three moieties independently selected from the group consisting of —O—, —NH—, —N(alkyl)-, —S—, —S(O)—, and —$SO_2$— or alkyl interrupted with one or two or three moieties independently selected from the group consisting of —O—, —NH—, —N(alkyl)-, —S—, —S(O)—, and —$SO_2$— and substituted with one or two or three substituents independently selected from the group consisting of cycloalkyl, halo, aryl, heteroaryl, heterocyclyl, —OH, =O, —O(alkyl), —$NH_2$, —$NHR^{30}$, and —$NR^{30}R^{31}$;

$R^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one or two or three substituents independently selected from the group consisting of cycloalkyl, aryl, heteroaryl, and heterocyclyl, alkyl interrupted with one or two or three moieties independently selected from the group consisting of —O—, —NH—, —N(alkyl)-, —S—, —S(O)—, and —$SO_2$—, alkyl interrupted with one or two or three moieties independently selected from the group consisting of —O—, —NH—, —N(alkyl)-, —S—, —S(O)—, and —$SO_2$— and substituted with one or two or three substituents independently selected from the group consisting of cycloalkyl, halo, aryl, heteroaryl, heterocyclyl, —OH, =O, —O(alkyl), —$NH_2$, —$NHR^{30}$, and —$NR^{30}R^{31}$, alkenyl interrupted with one or two moieties independently selected from the group consisting of —O—, —NH—, —N(alkyl)-, —S—, —S(O)—, and —$SO_2$—, alkenyl interrupted with one or two moieties independently selected from the group consisting of —O—, —NH—, —N(alkyl)-, —S—, —S(O)—, and —$SO_2$— and substituted with one or two or three substituents independently selected from the group consisting of cycloalkyl, halo, aryl, heteroaryl, heterocyclyl, —OH, =O, —O(alkyl), —$NH_2$, —$NHR^{30}$, and —$NR^{30}R^{31}$, alkynyl interrupted with one or two moieties independently selected from the group consisting of —O—, —NH—, —N(alkyl)-, —S—, —S(O)—, and —$SO_2$—, or alkynyl interrupted with one or two moieties independently selected from the group consisting of —O—, —NH—, —N(alkyl)-, —S—, —S(O)—, and —$SO_2$— and substituted with one or two or three substituents independently selected from the group consisting of cycloalkyl, halo, aryl, heteroaryl, heterocyclyl, —OH, =O, —O(alkyl), —$NH_2$, —$NHR^{30}$, and —$NR^{30}R^{31}$;

$R^{30}$ and $R^{31}$ are independently alkyl, cycloalkyl, aryl, heteroaryl, heterocyclyl, —($CH_2$)alkenyl, —($CH_2$)alkynyl, cycloalkyl, alkyl substituted with one substituent selected from the group consisting of cycloalkyl, aryl, heteroaryl, heterocyclyl, —$NH_2$, —NH(alkyl), and —N(alkyl)$_2$, —($CH_2$)alkenyl substituted with one substituent selected from the group consisting of cycloalkyl, aryl, heteroaryl, heterocyclyl, —$NH_2$, —NH(alkyl), and —N(alkyl)$_2$, or —($CH_2$)alkynyl substituted with one substituent selected from the group consisting of cycloalkyl, aryl, heteroaryl, heterocyclyl, —$NH_2$, —NH(alkyl), and —N(alkyl)$_2$; or $R^{30}$ and $R^{31}$ together are $C_3$–$C_6$-alkylene, $C_5$–$C_6$-alkylene interrupted with one moiety selected from the group consisting of —O—, —NH—, —N(alkyl)-, —S—, —S(O)—, and —SO$_2$—, C$_3$-C$_6$-alkylene substituted with one substituent selected from the group consisting of —OH, —O(alkyl), =O, —NH$_2$, —NH(alkyl), and —N(alkyl)$_2$, or C$_5$-C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$;

R$^{32}$ is —R$^{26}$, —C(O)OR$^{26}$, —C(O)NH$_2$, —C(O)NHR$^{27}$, —C(O)NR$^{27}$R$^{28}$, —CH$_2$R$^{29}$, —C(O)OCH$_2$R$^{29}$, —C(O)NHCH$_2$R$^{29}$, or —C(O)N(CH$_2$R$^{29}$)$_2$; and X$^1$ is hydrogen or fluoride.

2. The compound of claim 1 having formula (I) or formula (II), or a pharmaceutically acceptable salt, prodrug, or salt of a prodrug thereof, in which R$^1$ is hydrogen, —R$^{11}$, —C(O)OR$^{11}$, —C(O)NH$_2$, —C(O)NHR$^{12}$, or —C(O)NR$^{12}$R$^{13}$;

R$^2$ is hydrogen or R$^P$, in which R$^P$ is a hydroxyl protecting moiety;

one of R$^3$ or R$^4$ is hydrogen and the other is —OH, —OR$^P$, —OR$^{15}$, —OC(O)R$^{15}$, —OC(O)OR$^{15}$, —OC(O)NH$_2$, —OC(O)NHR$^{16}$, or —OC(O)NR$^{16}$R$^{17}$; or R$^3$ and R$^4$ together are =O or —CH$_2$O—;

R$^5$ is hydrogen, —R$^{19}$, —C(O)OR$^{19}$, —C(O)NH$_2$, —C(O)NHR$^{20}$, or —C(O)NR$^{20}$R$^{21}$;

R$^6$ and R$^{10}$ are independently hydrogen or —R$^{23}$;

R$^7$ is =O, =NOH, =NOR$^P$, or =NOR$^{24}$;

one of R$^8$ and R$^9$ is hydrogen, and the other is —OH or —OR$^{32}$; or

R$^8$ and R$^9$ together are =O;

R$^{11}$, R$^{15}$, R$^{19}$, R$^{24}$, and R$^{26}$ are independently alkyl, —(CH$_2$)alkenyl, —(CH$_2$)alkynyl, alkyl substituted with one or two or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

R$^{12}$, R$^{13}$, R$^{16}$, R$^{17}$, R$^{20}$, R$^{21}$, R$^{27}$, and R$^{28}$ are independently alkyl, cycloalkyl, —(CH$_2$)alkenyl, —(CH$_2$)alkynyl, cycloalkyl, aryl, heteroaryl, heterocyclyl, alkyl substituted with one substituent selected from the group consisting of cycloalkyl, aryl, heteroaryl, heterocyclyl, —NH$_2$, —NHR$^{30}$, and NR$^{30}$R$^{31}$, —(CH$_2$)alkenyl substituted with one substituent selected from the group consisting of cycloalkyl, aryl, heteroaryl, heterocyclyl, —NH$_2$, —NHR$^{30}$, and —NR$^{30}$R$^{31}$, or —(CH$_2$) alkynyl substituted with one substituent selected from the group consisting of cycloalkyl, aryl, heteroaryl, heterocyclyl, —NH$_2$, —NHR$^{30}$, and —NR$^{30}$R$^{31}$;

R$^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, or alkynyl substituted with one or two or three substituents independently selected from the group consisting of cycloalkyl, aryl, heteroaryl, and heterocyclyl;

R$^{30}$ and R$^{31}$ are independently alkyl, cycloalkyl, aryl, heteroaryl, heterocyclyl, —(CH$_2$)alkenyl, —(CH$_2$) alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$;

R$^{32}$ is —R$^{26}$, —C(O)OR$^{26}$, —C(O)NH$_2$, —C(O)NHR$^{27}$, or —C(O)NR$^{27}$R$^{28}$; and X$^1$ is hydrogen or fluoride.

3. The compound of claim 2 having formula (I) or formula (II), or a pharmaceutically acceptable salt, prodrug, or salt of a prodrug thereof, in which R$^1$ is hydrogen, —R$^{11}$, —C(O)OR$^{11}$, —C(O)NH$_2$, —C(O)NHR$^{12}$, or —C(O)NR$^{12}$R$^{13}$;

R$^2$ is hydrogen or R$^P$, in which R$^P$ is a hydroxyl protecting moiety;

one of R$^3$ or R$^4$ is hydrogen and the other is —OH, —OR$^P$, or —OC(O)R$^{15}$; or R$^3$ and R$^4$ together are =O or —CH$_2$O—;

R$^5$ is hydrogen, —R$^{19}$, —C(O)OR$^{19}$, —C(O)NH$_2$, —C(O)NHR$^{20}$, or —C(O)NR$^{20}$R$^{21}$;

R$^6$ and R$^{10}$ are independently hydrogen or —R$^{23}$;

R$^7$ is =O, =NOH, =NOR$^P$, or =NOR$^{24}$;

one of R$^8$ and R$^9$ is hydrogen, and the other is —OH or —OR$^{32}$; or

R$^8$ and R$^9$ together are =O;

R$^{11}$, R$^{15}$, R$^{19}$, R$^{24}$, and R$^{26}$ are independently alkyl, —(CH$_2$)alkenyl, —(CH$_2$)alkynyl, alkyl substituted with one or two or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$) alkynyl substituted with one or two or three substituents independently selected from the group consisting of cycloalkyl, aryl, heteroaryl, and heterocyclyl;

R$^{12}$, R$^{13}$, R$^{20}$, R$^{21}$, R$^{27}$, and R$^{28}$ are independently alkyl, cycloalkyl, —(CH$_2$)alkenyl, —(CH$_2$)alkynyl, cycloalkyl, aryl, heteroaryl, heterocyclyl, alkyl substituted with one substituent selected from the group consisting of cycloalkyl, aryl, heteroaryl, heterocyclyl, —NH$_2$, —NHR$^{30}$, and —NR$^{30}$R$^{31}$, —(CH$_2$)alkenyl substituted with one substituent selected from the group consisting of cycloalkyl, aryl, heteroaryl, heterocyclyl, —NH$_2$, —NHR$^{30}$, and —NR$^{30}$R$^{31}$, or —(CH$_2$) alkynyl substituted with one substituent selected from the group consisting of cycloalkyl, aryl, heteroaryl, heterocyclyl, —NH$_2$, —NHR$^{30}$, and —NR$^{30}$R$^{31}$;

R$^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, or alkynyl substituted with one or two or three substituents independently selected from the group consisting of cycloalkyl, aryl, heteroaryl, and heterocyclyl;

$R^{30}$ and $R^{31}$ are independently alkyl, cycloalkyl, aryl, heteroaryl, heterocyclyl, —($CH_2$)alkenyl, —($CH_2$) alkynyl, cycloalkyl, alkyl substituted with one substituent selected from the group consisting of cycloalkyl, aryl, heteroaryl, heterocyclyl, —$NH_2$, —NH(alkyl), and —N(alkyl)$_2$, —($CH_2$)alkenyl substituted with one substituent selected from the group consisting of cycloalkyl, aryl, heteroaryl, heterocyclyl, —$NH_2$, —NH(alkyl), and —N(alkyl)$_2$, or —($CH_2$)alkynyl substituted with one substituent selected from the group consisting of cycloalkyl, aryl, heteroaryl, heterocyclyl, —$NH_2$, —NH(alkyl), and —N(alkyl)$_2$;

$R^{32}$ is —$R^{26}$, —C(O)O$R^{26}$, —C(O)N$H_2$, —C(O)NH$R^{27}$, or —C(O)N$R^{27}R^{28}$; and $X^1$ is hydrogen or fluoride.

4. The compound of claim 3 having formula (I) or formula (II), or a pharmaceutically acceptable salt, prodrug, or salt of a prodrug thereof, in which $R^1$ is methyl, ethyl, prop-2-ynyl, or prop-2-enyl, each of which is unsubstituted or substituted with one substituent selected from the group consisting of phenyl, quinolinyl, isoquinolinyl, quinazolinyl, and quinoxalinyl in which each substitutuent is unsubstituted or substituted with one or two substitutuents independently selected from the group consisting of —F, —Cl, —Br, —I and —$NO_2$; $R^2$ is hydrogen; $R^3$ is —OH, ((phenyl)carbonyl)oxy, ((methyl)carbonyl)oxy, (trimethylsilyl)oxy, or (triethylsilyl)oxy and $R^4$ is hydrogen, or $R^3$ and $R^4$ together are =O or —$CH_2$O—; $R^5$ is hydrogen, methyl, ethyl, propyl, prop-2-ynyl, prop-2-enyl, phenylmethyl, 4-methoxyphenylmethyl or 2,4-dimethoxyphenylmethyl; $R^6$ is hydrogen, methyl, ethyl, ethynyl, or phenyl; $R^7$ is =O; $R^8$ is hydrogen and $R^9$ is —OH, or $R^8$ and $R^9$ together are =O; $R^{10}$ is hydrogen, methyl, ethyl, prop-2-ynyl or prop-2-enyl; and $X^1$ is hydrogen or fluoride.

5. The compound of claim 3 having formula (I) or formula (II), or a pharmaceutically acceptable salt, prodrug, or salt of a prodrug thereof, in which $R^1$ is prop-2-ynyl substituted with isoxazoyl, in which the isoxazolyl is substituted with one substituent selected from the group consisting of furyl, imidazolyl, isoquinolinyl, isothiazolyl, isoxazolyl, 1,2,3-oxadiazolyl, oxazolyl, pyridyl, pyrimidinyl, quinolinyl, tetrazolyl, 1,2,3-thiadiazolyl, 1,3,4-thiadiazolyl, thiazolyl, thienyl, and 1,2,3-triazolyl, in which each substitutuent is unsubstituted or substituted with one or two substitutuents independently selected from the group consisting of —F, —Cl, —Br, —I and —$NO_2$; $R^2$ is hydrogen; $R^3$ is —OH, ((phenyl)carbonyl)oxy, ((methyl)carbonyl)oxy, (trimethylsilyl)oxy, or (triethylsilyl)oxy and $R^4$ is hydrogen, or $R^3$ and $R^4$ together are =O or —$CH_2$O—; $R^5$ is hydrogen, methyl, ethyl, propyl, prop-2-ynyl, prop-2-enyl, phenylmethyl, 4-methoxyphenylmethyl, or 2,4-dimethoxyphenylmethyl; $R^6$ is hydrogen, methyl, ethyl, ethenyl, or phenyl; $R^7$ is =O; $R^8$ is hydrogen and $R^9$ is —OH, or $R^8$ and $R^9$ together are =O; $R^{10}$ is hydrogen, methyl, ethyl, prop-2-ynyl or prop-2-enyl; $X^1$ and is hydrogen or fluoride.

6. The compound of claim 3 having formula (I) or formula (II), or a pharmaceutically acceptable salt, prodrug, or salt of a prodrug thereof, in which $R^1$ is prop-2-ynyl substituted with thienyl, in which the thienyl is substituted with one substituent selected from the group consisting of furyl, imidazolyl, isoquinolinyl, isothiazolyl, isoxazolyl, 1,2,3-oxadiazolyl, oxazolyl, pyridyl, pyrimidinyl, quinolinyl, tetrazolyl, 1,2,3-thiadiazolyl, 1,3,4-thiadiazolyl, thiazolyl, thienyl, and 1,2,3-triazolyl, in which each substitutuent is unsubstituted or substituted with one or two substitutuents independently selected from the group consisting of —F, —Cl, —Br, —I and —$NO_2$; $R^2$ is hydrogen; $R^3$ is —OH, ((phenyl)carbonyl)oxy, ((methyl)carbonyl)oxy, (trimethylsilyl)oxy, or (triethylsilyl)oxy and $R^4$ is hydrogen, or $R^3$ and $R^4$ together are =O or —$CH_2$O—; $R^5$ is hydrogen, methyl, ethyl, propyl, prop-2-ynyl, prop-2-enyl, phenylmethyl, 4-methoxyphenylmethyl, or 2,4-dimethoxyphenylmethyl; $R^6$ is hydrogen, methyl, ethyl, ethenyl, or phenyl; $R^7$ is =O; $R^8$ is hydrogen and $R^9$ is —OH, or $R^8$ and $R^9$ together are =O; $R^{10}$ is hydrogen, methyl, ethyl, prop-2-ynyl or prop-2-enyl; and $X^1$ is hydrogen or fluoride.

7. The compound of claim 3 having formula (I) or formula (II), or a pharmaceutically acceptable salt, prodrug, or salt of a prodrug thereof, in which $R^1$ is prop-2-enyl substituted with isoxazoyl, in which the isoxazolyl is substituted with one substituent selected from the group consisting of furyl, imidazolyl, isoquinolinyl, isothiazolyl, isoxazolyl, 1,2,3-oxadiazolyl, oxazolyl, pyridyl, pyrimidinyl, quinolinyl, tetrazolyl, 1,2,3-thiadiazolyl, 1,3,4-thiadiazolyl, thiazolyl, thienyl, and 1,2,3-triazolyl, in which each substitutuent is unsubstituted or substituted with one or two substitutuents independently selected from the group consisting of —F, —Cl, —Br, —I and —$NO_2$; $R^2$ is hydrogen; $R^3$ is —OH, ((phenyl)carbonyl)oxy, ((methyl)carbonyl)oxy, (trimethylsilyl)oxy, or (triethylsilyl)oxy and $R^4$ is hydrogen, or $R^3$ and $R^4$ together are =O or —$CH_2$O—; $R^5$ is hydrogen, methyl, ethyl, propyl, prop-2-ynyl, prop-2enyl, phenylmethyl, 4-methoxyphenylmethyl, or 2,4-dimethoxyphenylmethyl; $R^6$ is hydrogen, methyl, ethyl, ethenyl, or phenyl; $R^7$ is =O; $R^8$ is hydrogen and $R^9$ is —OH, or $R^8$ and $R^9$ together are =O; $R^{10}$ is hydrogen, methyl, ethyl, prop-2-ynyl or prop-2-enyl; and is hydrogen or fluoride.

8. The compound of claim 3 having formula (I) or formula (II), or a pharmaceutically acceptable salt, prodrug, or salt of a prodrug thereof, in which $R^1$ is prop-2-enyl substituted with thienyl, in which the thienyl is substituted with one substituent selected from the group consisting of furyl, imidazolyl, isoquinolinyl, isothiazolyl, isoxazolyl, 1,2,3-oxadiazolyl, oxazolyl, pyridyl, pyrimidinyl, quinolinyl, tetrazolyl, 1,2,3-thiadiazolyl, 1,3,4-thiadiazolyl, thiazolyl, thienyl, and 1,2,3-triazolyl, in which each substitutuent is unsubstituted or substituted with one or two substitutuents independently selected from the group consisting of —F, —Cl, —Br, —I and —$NO_2$; $R^2$ is hydrogen; $R^3$ is —OH, ((phenyl)carbonyl)oxy, ((methyl)carbonyl)oxy, (trimethylsilyl)oxy, or (triethylsilyl)oxy and $R^4$ is hydrogen, or $R^3$ and $R^4$ together are =O or —$CH_2$O—; $R^5$ is hydrogen, methyl, ethyl, propyl, prop-2-ynyl, prop-2-enyl, phenylmethyl, 4-methoxyphenylmethyl, or 2,4-dimethoxyphenylmethyl;

$R^6$ is hydrogen, methyl, ethyl, ethenyl, or phenyl; $R^7$ is =O; $R^8$ is hydrogen and $R^9$ is —OH, or $R^8$ and $R^9$ together are =O; $R^{10}$ is hydrogen, methyl, ethyl, prop-2-ynyl or prop-2-enyl; and is hydrogen or fluoride.

9. The compound of claim 3 having formula (I) or formula (II), or a pharmaceutically acceptable salt, prodrug, or salt of a prodrug thereof, in which $R^1$ is methyl, prop-2-ynyl, 3-(5-pyridin-2-ylthien-2-yl)prop-2-ynyl, 3-(quinolin-3-yl)prop-2-enyl, 3-(3-pyridin-2-ylisoxazol-5-yl)prop-2-ynyl, or 3-(5-pyrimidin-2-ylthien-2-yl)prop-2-ynyl; $R^2$ is hydrogen; $R^3$ is —OH, ((phenyl)carbonyl)oxy, ((methyl)carbonyl)oxy, (trimethylsilyl)oxy, or (triethylsilyl)oxy and $R^4$ is hydrogen, or $R^3$ and $R^4$ together are =O or —CH$_2$O—; $R^5$ is hydrogen, methyl, ethyl, propyl, prop-2-ynyl, prop-2-enyl, phenylmethyl, 4-methoxyphenylmethyl, or 2,4-dimethoxyphenylmethyl; $R^6$ is hydrogen, methyl, ethyl, ethenyl, or phenyl; $R^7$ is =O; $R^8$ is hydrogen and $R^9$ is —OH, or $R^8$ and $R^9$ together are =O; $R^{10}$ is hydrogen, methyl, ethyl, prop-2-ynyl or prop-2-enyl; $X^1$ and is hydrogen or fluoride.

10. The compound of claim 3 having formula (I) or formula (II), or a pharmaceutically acceptable salt, prodrug, or salt of a prodrug thereof, in which $R^1$ is alkyl, —(CH$_2$)alkynyl, or —(CH$_2$)alkynyl substituted with thienyl, in which the thienyl is substituted with pyridyl; $R^2$ is hydrogen; $R^3$ is ((phenyl)carbonyl)oxy; $R^4$ is hydrogen; $R^5$ is hydrogen or alkyl; $R^6$ is hydrogen; $R^7$ is =O; $R^8$ and $R^9$ together are =O; $R^{10}$ is hydrogen; and $X^1$ is hydrogen.

11. The compound of claim 3 having formula (I) or formula (II), or a pharmaceutically acceptable salt, prodrug, or salt of a prodrug thereof, in which $R^1$ is methyl, prop-2-ynyl or prop-2-ynyl substituted with thienyl, in which the thienyl is substituted with pyridyl; $R^2$ is hydrogen; $R^3$ is ((phenyl)carbonyl)oxy; $R^4$ is hydrogen; $R^5$ is hydrogen or methyl; $R^6$ is hydrogen; $R^7$ is =O; $R^8$ and $R^9$ together are =O; $R^{10}$ is hydrogen; and $X^1$ is hydrogen.

12. The compound of claim 10 having formula (I) or formula (II), or a pharmaceutically acceptable salt, prodrug, or salt of a prodrug thereof, in which $R^1$ is methyl; $R^2$ is hydrogen; $R^3$ is ((phenyl)carbonyl)oxy; $R^4$ is hydrogen; $R^5$ is hydrogen or methyl; $R^6$ is hydrogen; $R^7$ is =O; $R^8$ and $R^9$ together are =O; $R^{10}$ is hydrogen; and $X^1$ is hydrogen.

13. The compound of claim 10 having formula (I) or formula (II), or a pharmaceutically acceptable salt, prodrug, or salt of a prodrug thereof, in which $R^1$ is prop-2-ynyl; $R^2$ is hydrogen; $R^3$ is ((phenyl)carbonyl)oxy; $R^4$ is hydrogen; $R^5$ is hydrogen or methyl; $R^{is\ 6}$ hydrogen; $R^7$ is =O; $R^8$ and $R^9$ together are =O; $R^{10}$ is hydrogen; and $X^1$ is hydrogen.

14. The compound of claim 10 having formula (I) or formula (II), or a pharmaceutically acceptable salt, prodrug, or salt of a prodrug thereof, in which $R^1$ is 3-(5-pyridin-2-ylthien-2-yl)prop-2-ynyl; $R^2$ is hydrogen; $R^3$ is ((phenyl)carbonyl)oxy; $R^4$ is hydrogen; $R^5$ is hydrogen or methyl; $R^6$ is hydrogen; $R^7$ is =O; $R^8$ and $R^9$ together are =O; $R^{10}$ is hydrogen; and $X^1$ is hydrogen.

15. A composition for treatment of bacterial infections in a fish or a mammal comprising a therapeutically effective amount of a compound of claim 1 and an excipient.

16. A method for treatment of bacterial infections in a fish or a mammal comprising administering to the fish of the mammal a therapeutically effective amount of a compound of claim 1.

17. A process for making a compound having formula (I)-b

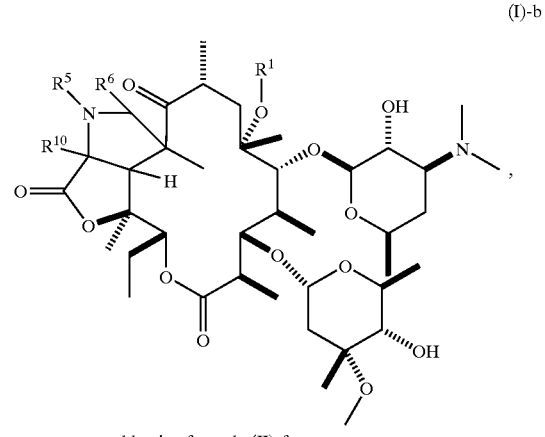

or a compound having formula (II)-f

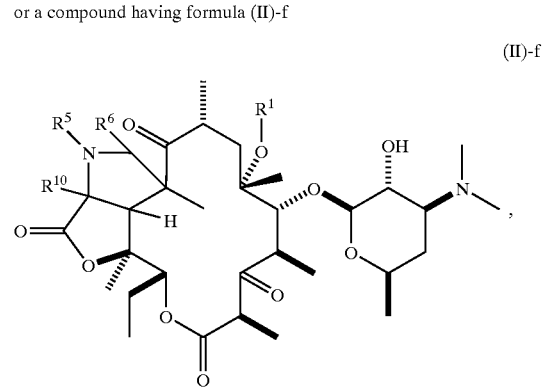

or a salt, prodrug, or salt of a prodrug thereof, in which $R^1$ is hydrogen, —$R^{11}$, —C(O)O$R^{11}$, —C(O)NH$_2$, —C(O)NH$R^{12}$, —C(O)N$R^{12}R^{13}$, —CH$_2R^{14}$, —C(O)OCH$_2R^{14}$, —C(O)NHCH$_2R^{14}$, or —C(O)N(CH$_2R^{14}$)$_2$;

$R^5$ is hydrogen, —$R^{19}$, —C(O)O$R^{19}$, —C(O)NH$_2$, —C(O)NH$R^{20}$, —C(O)N$R^{20}R^{21}$, —CH$_2R^{22}$, —C(O)OCH$_2R^{22}$, —C(O)NHCH$_2R^{22}$, or —OC(O)N(CH$_2R^{22}$)$_2$;

$R^6$ and $R^{10}$ are independently hydrogen or —$R^{23}$;

$R^{11}$ and $R^{19}$ are independently alkyl, —(CH$_2$)alkenyl, —(CH$_2$)alkynyl, alkyl substituted with one, two, or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

$R^{12}$, $R^{13}$, $R^{20}$, and $R^{21}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NH$R^{30}$, and —N$R^{30}R^{31}$, —(CH$_2$)alkenyl substituted with one substituent selected from the group consisting of cycloalkyl, aryl, heteroaryl, heterocyclyl, —NH$_2$, —NH$R^{30}$, and —N$R^{30}R^{31}$, or —(CH$_2$)alkynyl substituted with one substituent selected from the group consisting of cycloalkyl, aryl, heteroaryl, heterocyclyl, —NH$_2$, —NHR$^{30}$, and —NR$^{30}$R$^{31}$; or R$^{12}$ and R$^{13}$ together, or R$^{20}$ and R$^{21}$ together are independently C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NHR$^{30}$, and —NR$^{30}$R$^{31}$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NHR$^{30}$, and —NR$^{30}$R$^{31}$;

R$^{14}$ and R$^{22}$ are independently alkyl interrupted with one or two or three moieties independently selected from the group consisting of —O—, —NH—, —N(alkyl)-, —S—, —S(O)—, and —SO$_2$— or alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

R$^{23}$ is alkyl, alkenyl, alkynyl, aryl, heteroaryl, heterocyclyl, alkyl substituted with one, two, or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one, two, or three substituents independently selected from the group consisting of cycloalkyl, aryl, heteroaryl, and heterocyclyl, alkyl interrupted with one or two or three moieties independently selected from the group consisting of —O—, —NH—, —N(alkyl)-, —S—, —S(O)—, and —SO$_2$—, alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkenyl interrupted with one or two moieties independently selected from the group consisting of —O—, —NH—, —N(alkyl)-, —S—, —S(O)—, and —SO$_2$—, alkenyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkynyl interrupted with one or two moieties independently selected from the group consisting of —O—, —NH—, —N(alkyl)-, —S—, —S(O)—, and —SO$_2$—, or alkynyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$; and R$^{30}$ and R$^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting .of cycloalkyl, aryl, heteroaryl, heterocyclyl, —NH$_2$, —NH(alkyl), and —N(alkyl)$_2$; or R$^{30}$ and R$^{31}$ together are C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NH(alkyl), and —N(alkyl)$_2$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$, the process comprising the steps of:

(a) reacting a compound having formula (X)

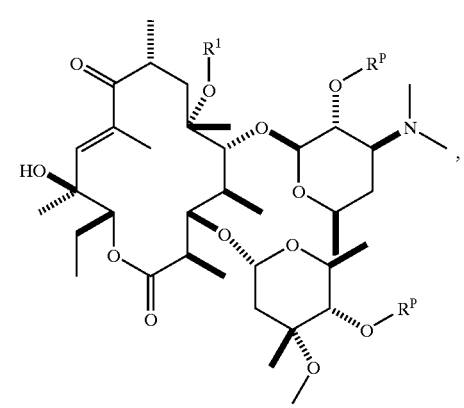

(X)

or a compound having formula (IX)

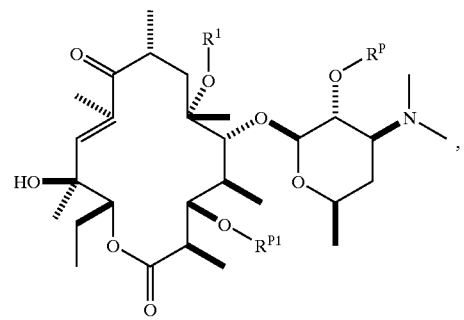

(IX)

in which R$^P$ is a hydroxyl protecting moiety and R$^{P1}$ is trimethylsilyl or triethylsilyl, a compound having formula (X$^2$CHR$^{10}$CO)$_2$O, in which X$^2$ is —Cl or —Br, and a second base, with or without 4-(N,N-dimethylamino)pyridine, to provide a compound having formula (XI)

(XI)

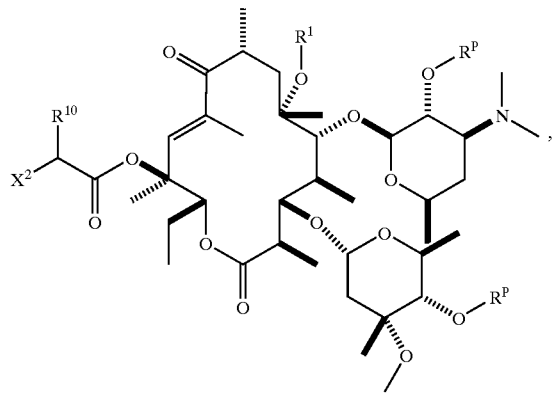

or a compound having formula (XIII)

(XIII)

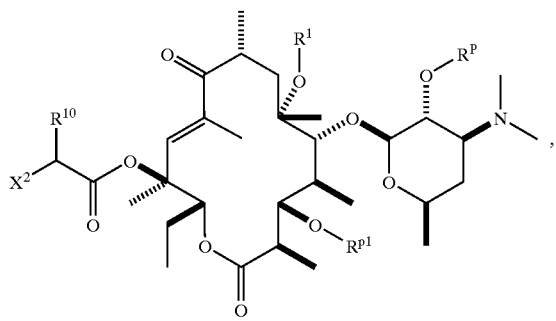

respectively;

(b) reacting the product of step (a) and a compound having formula $R^5NH_2$ to provide a compound having formula (XII)

(XII)

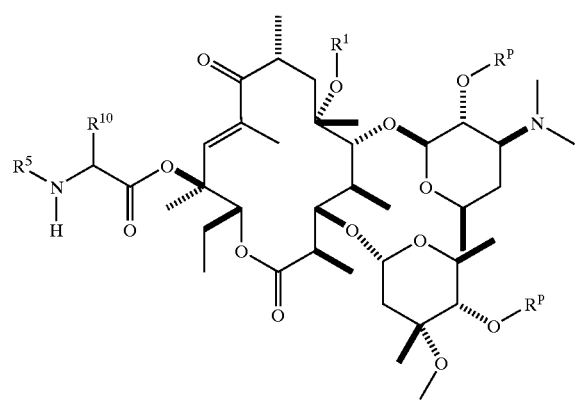

or a compound having formula (XIV)

-continued (XIV)

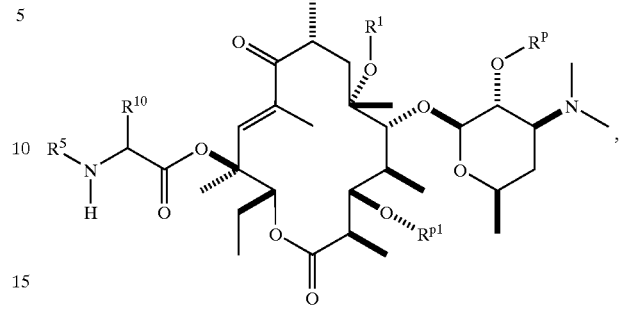

respectively;

(c) reacting the product of step (b), a compound having formula $R^6CHO$, and a first acid, between about 75° C. and about 120° C., to provide a compound having formula (I)-a (I)-a

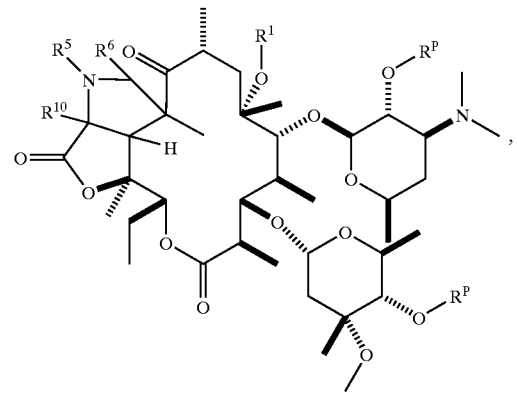

or a compound having formula (XV), (XV)

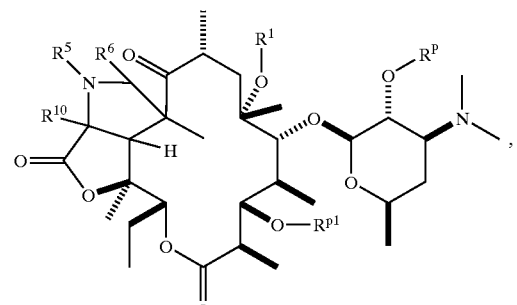

respectively;

(d) reacting the compound having formula (XV) and a fluoride-donating agent then reacting the product obtained therefrom and an oxidant, with or without a second base, to provide a compound having formula (II)-c

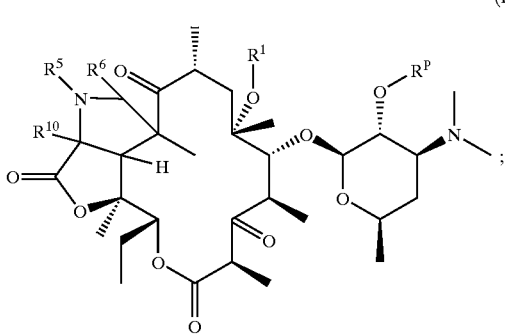

(II)-c and
(e)-(1) reacting the compound having formula (I)-a and a deprotecting agent, or
(e)-(2) reacting the compound having formula (II)-c and a deprotecting agent.

18. A process for making a compound having formula (II)-g

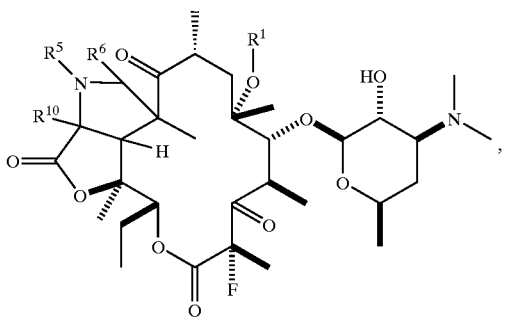

(II)-g or a salt, prodrug, or salt of a prodrug thereof, in which
$R^1$ is hydrogen, $-R^{11}$, $-C(O)OR^{11}$, $-C(O)NH_2$, $-C(O)NHR^{12}$, $-C(O)NR^{12}R^{13}$, $-CH_2R^{14}$, $-C(O)OCH_2R^{14}$, $-C(O)NHCH_2R^{14}$, or $-C(O)N(CH_2R^{14})_2$;
$R^5$ is hydrogen, $-R^{19}$, $-C(O)OR^{19}$, $-C(O)NH_2$, $-C(O)NHR^{20}$, $-C(O)NR^{20}R^{21}$, $-CH_2R^{22}$, $-C(O)OCH_2R^{22}$, $-C(O)NHCH_2R^{22}$, or $-OC(O)N(CH_2R^{22})_2$;
$R^6$ and $R^{10}$ are independently hydrogen or $-R^{23}$;
$R^{11}$ and $R^{19}$ are independently alkyl, $-(CH_2)$alkenyl, $-(CH_2)$alkynyl, alkyl substituted with one, two, or three substituents independently selected from the group consisting of cycloalkyl, halo, aryl, heteroaryl, and heterocyclyl, $-(CH_2)$alkenyl substituted with one or two or three substituents independently selected from the group consisting of cycloalkyl, halo, aryl, heteroaryl, and heterocyclyl, or $-(CH_2)$alkynyl substituted with one or two or three substituents independently selected from the group consisting of cycloalkyl, aryl, heteroaryl, and heterocyclyl;
$R^{12}$, $R^{13}$, $R^{20}$, and $R^{21}$ are independently alkyl, cycloalkyl, $-(CH_2)$alkenyl, $-(CH_2)$alkynyl, aryl, heteroaryl, heterocyclyl, alkyl substituted with one substituent selected from the group consisting of cycloalkyl, aryl, heteroaryl, heterocyclyl, $-NH_2$, $-NHR^{30}$, and $-NR^{30}R^{31}$, $-(CH_2)$alkenyl substituted with one substituent selected from the group consisting of cycloalkyl, aryl, heteroaryl, heterocyclyl, $-NH_2$, $-NHR^{30}$, and $-NR^{30}R^{31}$, or $-(CH_2)$alkynyl substituted with one substituent selected from the group consisting of cycloalkyl, aryl, heteroaryl, heterocyclyl, $-NH_2$, $-NHR^{30}$, and $-NR^{30}R^{31}$; or
$R^{12}$ and $R^{13}$ together, or $R^{20}$ and $R^{21}$ together are $C_3$–$C_6$-alkylene, $C_5$–$C_6$-alkylene interrupted with one moiety selected from the group consisting of $-O-$, $-NH-$, $-N(alkyl)$-, $-S-$, $-S(O)-$, and $-SO_2$, $-C_3$–$C_6$-alkylene substituted with one substituent selected from the group consisting of $-OH$, $-O(alkyl)$, $=O$, $-NH_2$, $-NHR^{30}$, and $-NR^{30}R^{31}$, or $C_5$–$C_6$-alkylene interrupted with one moiety selected from the group consisting of $-O-$, $-NH-$, $-N(alkyl)$-, $-S-$, $-S(O)-$, and $-SO_2-$ and substituted with one substituent selected from the group consisting of $-OH$, $-O(alkyl)$, $=O$, $-NH_2$, $-NHR^{30}$, and $-NR^{30}R^{31}$;
$R^{14}$ and $R^{22}$ are independently alkyl interrupted with one or two or three moieties independently selected from the group consisting of $-O-$, $-NH-$, $-N(alkyl)$-, $-S-$, $-S(O)-$, and $-SO_2-$ or alkyl interrupted with one or two or three moieties independently selected from the group consisting of $-O-$, $-NH-$, $-N(alkyl)$-, $-S-$, $-S(O)-$, and $-SO_2-$ and substituted with one or two or three substituents independently selected from the group consisting of cycloalkyl, halo, aryl, heteroaryl, heterocyclyl, $-OH$, $=O$, $-O(alkyl)$, $-NH_2$, $-NHR^{30}$, and $-NR^{30}R^{31}$;
$R^{23}$ is alkyl, alkenyl, alkynyl, aryl, heteroaryl, heterocyclyl, alkyl substituted with one, two, or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one, two, or three substituents independently selected from the group consisting of cycloalkyl, aryl, heteroaryl, and heterocyclyl, alkyl interrupted with one or two or three moieties independently selected from the group consisting of $-O-$, $-NH-$, $-N(alkyl)$-, $-S-$, $-S(O)-$, and $-SO_2-$, alkyl interrupted with one or two or three moieties independently selected from the group consisting of $-O-$, $-NH-$, $-N(alkyl)$-, $-S-$, $-S(O)-$, and $-SO_2-$ and substituted with one or two or three substituents independently selected from the group consisting of cycloalkyl, halo, aryl, heteroaryl, heterocyclyl, $-OH$, $=O$, $-O(alkyl)$, $-NH_2$, $-NHR^{30}$, and $-NR^{30}R^{31}$, alkenyl interrupted with one or two moieties independently selected from the group consisting of $-O-$, $-NH-$, $-N(alkyl)$-, $-S-$, $-S(O)-$, and $-SO_2-$, alkenyl interrupted with one or two moieties independently selected from the group consisting of $-O-$, $-NH-$, $-N(alkyl)$-, $-S-$, $-S(O)-$, and $-SO_2-$ and substituted with one or two or three substituents independently selected from the group consisting of cycloalkyl, halo, aryl, heteroaryl, heterocyclyl, $-OH$, $=O$, $-O(alkyl)$, —NH₂, —NHR³⁰, and —NR³⁰R³¹, alkynyl interrupted with one or two moieties independently selected from the group consisting of —O—, —NH—, —N(alkyl)-, —S—, —S(O)—, and —SO₂—, or alkynyl interrupted with one or two moieties independently selected from the group consisting of —O—, —NH—, —N(alkyl)-, —S—, —S(O)—, and —SO₂— and substituted with one or two or three substituents independently selected from the group consisting of cycloalkyl, halo, aryl, heteroaryl, heterocyclyl, —OH, =O, —O(alkyl), —NH₂, —NHR³⁰, and —NR³⁰R³¹; and R³⁰ and R³¹ are independently alkyl, cycloalkyl, aryl, heteroaryl, heterocyclyl, —(CH₂)alkenyl, —(CH₂)alkynyl, cycloalkyl, alkyl substituted with one substituent selected from the group consisting of cycloalkyl, aryl, heteroaryl, heterocyclyl, —NH₂, —NH(alkyl), and —N(alkyl)₂, —(CH₂)alkenyl substituted with one substituent selected from the group consisting of cycloalkyl, aryl, heteroaryl, heterocyclyl, —NH₂, —NH(alkyl), and —N(alkyl)₂, or —(CH₂)alkynyl substituted with one substituent selected from the group consisting of cycloalkyl, aryl, heteroaryl, heterocyclyl, —NH₂, —NH(alkyl), and —N(alkyl)₂;

or

R³⁰ and R³¹ together are C₃–C₆-alkylene, C₅–C₆-alkylene interrupted with one moiety selected from the group consisting of —O—, —NH—, —N(alkyl)-, —S—, —S(O)—, and —SO₂—, C₃–C₆-alkylene substituted with one substituent selected from the group consisting of —OH, —O(alkyl), =O, —NH₂, —NH(alkyl), and —N(alkyl)₂, or C₅–C₆-alkylene interrupted with one moiety selected from the group consisting of —O—, —NH—, —N(alkyl)-, —S—, —S(O)—, and —SO₂— and substituted with one substituent selected from the group consisting of —OH, —O(alkyl), =O, —NH₂, —NH(alkyl), and —N(alkyl)₂, the process comprising the steps of:

(a) reacting a compound having formula (II)-c (II)-c

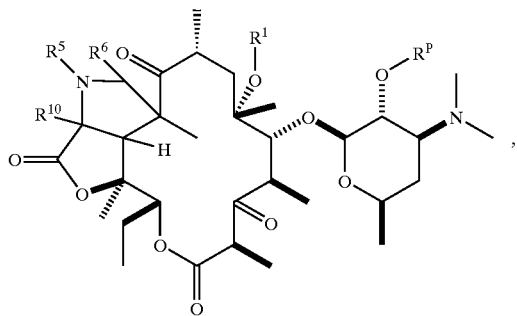

in which

R^P is a hydroxyl protecting moiety, and a fluorinating agent, with or without a fourth base; and (b) reacting the product of step (a) and a deprotecting agent.

19. A compound having formula (XI)

(XI)

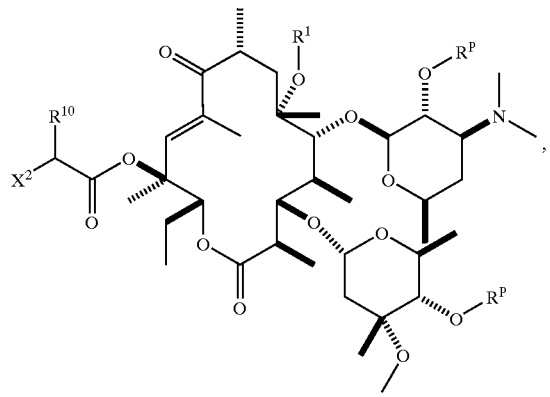

or a compound having formula (XII), (XII)

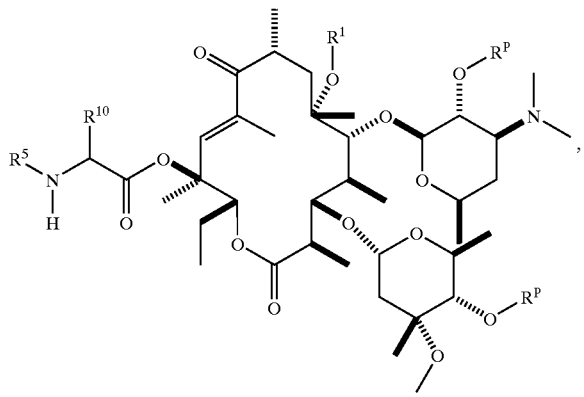

or a salt thereof, in which

R¹ is hydrogen, —R¹¹, —C(O)OR¹¹, —C(O)NH₂, —C(O)NHR¹², —C(O)NR¹²R¹³, —CH₂R¹⁴, —C(O)OCH₂R¹⁴, —C(O)NHCH₂R¹⁴, or —C(O)N(CH₂R¹⁴)₂;

R⁵ is hydrogen, —R¹⁹, —C(O)OR¹⁹, —C(O)NH₂, —C(O)NHR²⁰, —C(O)NR²⁰R²¹, —CH₂R²², —C(O)OCH₂R²², —C(O)NHCH₂R²², or —OC(O)N(CH₂R²²)₂;

R¹⁰ is hydrogen or —R²³;

R¹¹ and R¹⁹ are independently alkyl, —(CH₂)alkenyl, —(CH₂)alkynyl, alkyl substituted with one or two or three substituents independently selected from the group consisting of cycloalkyl, halo, aryl, heteroaryl, and heterocyclyl, —(CH₂)alkenyl substituted with one or two or three substituents independently selected from the group consisting of cycloalkyl, halo, aryl, heteroaryl, and heterocyclyl, or —(CH₂)alkynyl substituted with one or two or three substituents independently selected from the group consisting of cycloalkyl, aryl, heteroaryl, and heterocyclyl;

R¹², R¹³, R²⁰, and R²¹ are independently alkyl, cycloalkyl, —(CH₂)alkenyl, —(CH₂)alkynyl, aryl, heteroaryl, heterocyclyl, alkyl substituted with one substituent selected from the group consisting of cycloalkyl, aryl, heteroaryl, heterocyclyl, —NH₂, —NHR³⁰, and NR³⁰R³¹, —(CH₂)alkenyl substituted with one substituent selected from the group consisting of cycloalkyl, aryl, heteroaryl, heterocyclyl, —NH$_2$, —NHR$^{30}$, and —NR$^{30}$R$^{31}$, or —(CH$_2$)alkynyl substituted with one substituent selected from the group consisting of cycloalkyl, aryl, heteroaryl, heterocyclyl, —NH$_2$, —NHR$^{30}$, and —NR$^{30}$R$^{31}$; or R$^{12}$ and R$^{13}$ together, or R$^{20}$ and R$^{21}$ together are independently C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NHR$^{30}$, and —NR$^{30}$R$^{31}$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NHR$^{30}$, and —NR$^{30}$R$^{31}$;

R$^{14}$ and R$^{22}$ are independently alkyl interrupted with one or two or three moieties independently selected from the group consisting of —O—, —NH—, —N(alkyl)-, —S—, —S(O)—, and —SO$_2$— or alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

R$^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one or two or three substituents independently selected from the group consisting of cycloalkyl, aryl, heteroaryl, and heterocyclyl, alkyl interrupted with one or two or three moieties independently selected from the group consisting of —O—, —NH—, —N(alkyl)-, —S—, —S(O)—, and —SO$_2$—, alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkenyl interrupted with one or two moieties independently selected from the group consisting of —O—, —NH—, —N(alkyl)-, —S—, —S(O)—, and —SO$_2$—, alkenyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkynyl interrupted with one or two moieties independently selected from the group consisting of —O—, —NH—, —N(alkyl)-, —S—, —S(O)—, and —SO$_2$—, or alkynyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

R$^{30}$ and R$^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; or R$^{30}$ and R$^{31}$ together are C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NH(alkyl), and —N(alkyl)$_2$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$;

R$^P$ is (methyl)carbonyl or (phenyl)carbonyl; and

X$^2$ is chloride or bromide.

20. A compound having formula (XIII)

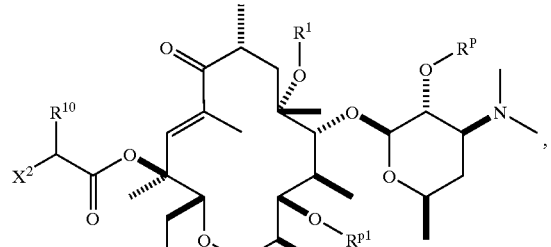

(XIII)

or a compound having formula (XIV)

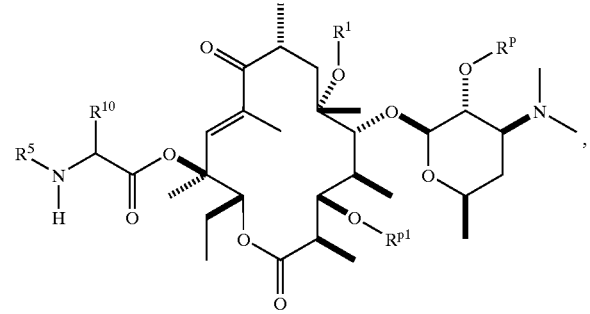

(XIV)

or a salt thereof, in which

R$^1$ is hydrogen, —R$^{11}$, —C(O)OR$^{11}$, —C(O)NH$_2$, —C(O)NHR$^{12}$, —C(O)NR$^{12}$R$^{13}$, —CH$_2$R$^{14}$, —C(O)OCH$_2$R$^{14}$, —C(O)NHCH$_2$R$^{14}$, or —C(O)N(CH$_2$R$^{14}$)$_2$;

R$^5$ is hydrogen, —R$^{19}$, —C(O)OR$^{19}$, —C(O)NH$_2$, —C(O)NHR$^{20}$, —C(O)NR$^{20}$R$^{21}$, —CH$_2$R$^{22}$, —C(O)OCH$_2$R$^{22}$, —C(O)NHCH$_2$R$^{22}$, or —OC(O)N(CH$_2$R$^{22}$)$_2$;

R$^{10}$ is hydrogen or —R$^{23}$;

R$^{11}$ and R$^{19}$ are independently alkyl, —(CH$_2$)alkenyl, —(CH$_2$)alkynyl, alkyl substituted with one or two or three substituents independently selected from the group consisting of cycloalkyl, halo, aryl, heteroaryl, and heterocyclyl, —(CH$_2$)alkenyl substituted with one or two or three substituents independently selected from the group consisting of cycloalkyl, halo, aryl, heteroaryl, and heterocyclyl, or —(CH$_2$)alkynyl substituted with one or two or three substituents independently selected from the group consisting of cycloalkyl, aryl, heteroaryl, and heterocyclyl;

R$^{12}$, R$^{13}$, R$^{20}$, and R$^{21}$, are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR$^{30}$, and —NR$^{30}$R$^{31}$, —(CH$_2$)alkenyl substituted with one substituent selected from the group consisting of cycloalkyl, aryl, heteroaryl, heterocyclyl, —NH$_2$, —NHR$^{30}$, and —NR$^{30}$R$^{31}$, or —(CH$_2$)alkynyl substituted with one substituent selected from the group consisting of cycloalkyl, aryl, heteroaryl, heterocyclyl, —NH$_2$, —NHR$^{30}$, and —NR$^{30}$R$^{31}$; or R$^{12}$ and R$^{13}$ together, or R$^{20}$ and R$^{21}$ together are independently C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NHR$^{30}$, and —NR$^{30}$R$^{31}$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NHR$^{30}$, and —NR$^{30}$R$^{31}$;

R$^{14}$ and R$^{22}$ are independently alkyl interrupted with one or two or three moieties independently selected from the group consisting of —O—, —NH—, —N(alkyl)-, —S—, —S(O)—, and —SO$_2$— or alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

R$^{23}$ is alkyl, alkenyl, alkynyl, aryl, heteroaryl, heterocyclyl, alkyl substituted with one or two or three substituents independently selected from the group consisting of cycloalkyl, halo, aryl, heteroaryl, and heterocyclyl, alkenyl substituted with one or two or three substituents independently selected from the group consisting of cycloalkyl, halo, aryl, heteroaryl, and heterocyclyl, alkynyl substituted with one or two or three substituents independently selected from the group consisting of cycloalkyl, aryl, heteroaryl, and heterocyclyl, alkyl interrupted with one or two or three moieties independently selected from the group consisting of —O—, —NH—, —N(alkyl)-, —S—, —S(O)—, and —SO$_2$—, alkyl interrupted with one or two or three moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkenyl interrupted with one or two moieties independently selected from the group consisting of —O—, —NH—, —N(alkyl)-, —S—, —S(O)—, and —SO$_2$—, alkenyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$, alkynyl interrupted with one or two moieties independently selected from the group consisting of —O—, —NH—, —N(alkyl)-, —S—, —S(O)—, and —SO$_2$—, or alkynyl interrupted with one or two moieties independently selected from the group consisting of —O—, —NH—, —N(alkyl)-, —S—, —S(O)—, and —SO$_2$— and substituted with one or two or three substituents independently selected from the group consisting of cycloalkyl, halo, aryl, heteroaryl, heterocyclyl, —OH, =O, —O(alkyl), —NH$_2$, —NHR$^{30}$, and —NR$^{30}$R$^{31}$;

R$^{30}$ and R$^{31}$ are independently alkyl, cycloalkyl, aryl, heteroaryl, heterocyclyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; or R$^{30}$ and R$^{31}$ together are C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NH(alkyl), and —N(alkyl)$_2$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$;

R$^P$ is (methyl)carbonyl or (phenyl)carbonyl;

R$^{P1}$ is trimethylsilyl or triethylsilyl; and

X$^2$ is chloride or bromide.

21. A compound or a pharmaceutically acceptable salt, prodrug, or salt of a prodrug thereof, which is (2aR,4aS,6R,8S,9R,10R,12R,15R,15aS,15bS)-15-ethyl-12-fluoro-8-methoxy-3,4a,6,8,10,12,15a-heptamethyl-2,5,11,13-tetraoxohexadecahydro-2H-1,14-dioxa-3azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-8-methoxy-4a,6,8,10,12,15a-hexamethyl-2,5,11,13-tetraoxohexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-8-methoxy-4a,6,8,10,12,15a-hexamethyl-2,5,11,13-tetraoxohexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-8-methoxy-3,4a,6,8,10,12,15a-heptamethyl-2,5,13-trioxo-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-8-methoxy-4a,6,8,10,12,15a-hexamethyl-2,5,13-trioxo-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-8-methoxy-4a,6,8,10,12,15a-hexamethyl-2,5,13-trioxo-9-((3,4,6-trideoxy-3-(dimethylamino)-β-D-xylo-hexapyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-12-fluoro-8-methoxy-4a,6,8,10,12,15a-hexamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-3,4a,6,8,10,12,15a-heptamethyl-2,5,11,13tetraoxo-8-(prop-2-ynyloxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6,8,10,12,15a-hexamethyl-2,5,11,13-tetraoxo-8-(prop-2-ynyloxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,6,8,10,12,15a-hexamethyl-2,5,11,13-tetraoxo-8-(prop-2-ynyloxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-(prop-2-ynyloxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-(prop-2-ynyloxy)hexadecahydro-2H-1,14-dioxa3-azacyclotetradeca(1,2,3-cd)pentalen-9-yl 3,4,6-trideoxy-3-(dimethyamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,13-trioxo-8-(prop-2-ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6dideoxy-3-C-methyl-3-O-methyl-α-L-ribo-hexopyranoside;

(2aR,4aS,6R,8S,9R,10R,12R,15R,15aS,15bS)-3-allyl-15-ethyl-4a,6,8,10,12,15a-hexamethyl-2,5,13-trioxo-8-(prop-2-ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-(prop-2ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-12-fluoro-3,4a,6,8,10,12,15a-heptamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl -4a,6,8,10,12,15a-hexamethyl-2,5,11,13-tetraoxo-8-((3-(5-(pyridin-2-yl)thien-2-yl)prop-2-ynyl)oxy)hexadecahydro2H- 1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,6,8,10,12,15a-hexamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethyamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,13-trioxo-8-((3-(5-(pyridin-2-yl)thien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-4a,6,8,10,12,15a-hexamethyl-2,5,13-trioxo-8-((3-(5-(pyridin-2-yl)thien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-β-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-((3-(5-(pyridin-2-yl)thien--2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-3,4a,6,8,10,12,15a-heptamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6,8,10,12,15a-hexamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,6,8,10,12,15a-hexamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-((3(5-pyrimidin-2-ylthien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-((3-(5-pyrimidin-2-ylthien-2-yl)prop-2-ynyl)oxy)hexadecahydro-2H-1,14-dioxa-3-azacyclotetradeca(1,2,3cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,13-trioxo-8-((3-(5-pyrimidin-2-ylthien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-4a,6,8,10,12,15a-hexamethyl-2,5,13-trioxo-8-((3-(5-pyrimidin-2-ylthien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-((3-(5-(pyridin-2-yl)thien-2-yl)prop-2-ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-3,4a,6,8,10,12,15a-heptamethyl-2,5,11,13-tetraoxo-8-((3-(3-pyridin-2-ylisoxazol5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6, 8, 10, 12,15a-hexamethyl-2,5,11,13-tetraoxo-8-((3-(3-pyridin-2-ylisoxazol5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,6,8,10,12,15a-hexamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-((3-(3-pyridin-2-ylisoxazol-5-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,83, 9R,10R,12R,15R,15aS,15bS)-15-ethyl-3,4a,6,8,10,12,15a-heptamethyl-2,5,13-trioxo-8-((3(3-pyridin-2-ylisoxazol-5-yl)prop-2ynyl)oxy)9-((3,4,6-trideoxy-3-(dimethylamino)-β-D-xylo-hexopyranosyl)oxy)hexadecahydro-2H-1,14-dioxa-3-azacyclotetradeca(1,2,3-cd)-pentalen- 11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-4a,6,8,10,12,15a-hexamethyl-2,5,13-trioxo-8-((3-(3-pyridin-2-ylisoxazol-5-yl)prop-2ynyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)-pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-((3-(3-pyridin-2-ylisoxazol-5-yl)prop-2ynyl)oxy)-9-((3,4,6-trideoxy-3-(dimethylamino)-β-D-xylo-hexopyranosyl)oxy)hexadecahydro-2H-1,14-dioxa-3- azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-3,4a,6,8,10,12,15a-heptamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-4a,6,8,10,12,15a-hexamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-3-allyl-15-ethyl-12-fluoro-4a,6,8,10,12,15a-hexamethyl-2,5,11,13-tetraoxo-8-(((2E)-3-quinolin-3-ylprop-2-enyl)oxy)-hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-4a,6,8,10,12,15a-hexamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-12-fluoro-4a,6,8,10,12,15a-hexamethyl-2,5,11,13-tetraoxo-8-(((2E)-3-quinolin-3-ylprop-2-enyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-3,4a,6,8,10,12,15a-heptamethyl-2,5,13-trioxo-8-(((2E)3-quinolin-3-ylprop-2-enyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-3-allyl-15-ethyl-4a,6,8,10,12,15a-hexamethyl-2,5,13-trioxo-8-(((2E)3-quinolin-3-ylprop-2-enyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-4a,6,8,10,12,15a-hexamethyl-2,5,13-trioxo-8-(((2E)-3-quinolin-3-ylprop-2-enyl)oxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-((3-(5-(pyridin-2-yl)thien-2-yl)prop-2-ynyloxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-8-methoxy-3,4a,6,8,10,12,15a-heptamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aS,4aR,6R,8S,9R,10R,12R,15R,15aS,15bR)15-ethyl-8-methoxy-3,4a,6,8,10,12,15a-heptamethyl-2,5,11,13-tetraoxohexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,10S,11S,12R,15R,15aS,15bS)-15-ethyl-3,4a,6,8,10,12,15a-heptamethyl-2,5,13-trioxo-8-(prop-2-ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 4-O-benzoyl-2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-(prop-2-ynyloxy)hexadecahydro-2H-1,14-dioxa-3-azacyclotetradeca-(1,2,3-cd)pentalen-9-yl 3,4,6-trideoxy-3-(dimethylamino)-β-D-xylo-hexopyranoside; or (2aR,4aS,6R,8S,9R,10R,12R,15R,15aS,15bS)-15-ethyl-8-methoxy-4a,6,8,10,12,15a-hexamethyl-2,5,11,13-tetraoxohexa-decahydro-2H-1,14-dioxa-3-azacyclotetradeca(1,2,3-cd)-pentalen-9-yl 3,4,6-trideoxy-3-(dimethylamino)-β-D-xylo-hexopyranoside.

22. The compound of claim 21, or a pharmaceutically acceptable salt, prodrug, or salt of a prodrug thereof, which is (2aR,4aS,6R,8S,9R,10R,12R,15R,15aS,15bS)-15-ethyl-3,4a,6,8,10,12,15a-heptamethyl-2,5,11,13-tetraoxo-8-((3-(5-(pyridin-2-yl)thien-2-yl)prop-2-ynyl)oxy)hexadecahydro-2H-1,14-dioxa-3-azacyclotetradeca(1,2,3-cd)pentalen-9-yl 3,4,6-trideoxy-3-(dimethylamino)-β-D-xylo-hexopyranoside;

(2aR,4aS,6R,8S,9R,10R,12R,15R,15aS,15bS)-15-ethyl-8-methoxy-3,4a,6,8,10,12,15a-heptamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aS,4aR,6R,8S,9R,10R,12R,15R,15aS,15bR)-15-ethyl-8-methoxy-3,4a,6,8,10,12,15a-heptamethyl-2,5,11,13-tetraoxohexadecahydro-2H-1,14-dioxa-3-azacyclotetradeca-(1,2,3-cd)pentalen-9-yl 3,4,6-trideoxy-3-(dimethylamino)-β-D-xylo-hexopyranoside;

(2aR,4aS,6R,8S,9R,10S,11S,12R,15R,15aS,15bS)-15-ethyl-3,4a,6,8,10,12,15a-heptamethyl-2,5,13-trioxo-8-(prop-2-ynyloxy)-9-((3,4,6-trideoxy-3-(dimethylamino)-β-D-xylo-hexopyranosyl)oxy)hexadecahydro-2H-1,14-dioxa-3-azacyclotetradeca(1,2,3-cd)pentalen-11-yl 4-O-benzoyl-2,6-dideoxy-3-C-methyl-3-O-methyl-α-L-ribo-hexopyranoside;

(2aR,4aS,6R,8S,9R,10R,12R,15R,15aS,15bS)-15-ethyl-3,4a,6,8,10,12,15a-heptamethyl-2,5,11,13-tetraoxo-8-(prop-2-ynyloxy)-hexadecahydro-2H-1,14-dioxa-3-azacyclotetradeca-(1,2,3-cd)pentalen-9-yl 3,4,6-trideoxy-3-(dimethylamino)-β-D-xylo-hexopyranoside; or (2aR,4aS,6R,8S,9R,10R,12R,15R,15aS,15bS)-15-ethyl-8-methoxy-4a,6,8,10,12,15a-hexamethyl-2,5,11,13-tetraoxohexadecahydro-2H-1,14-dioxa-3-azacyclotetradeca( 1,2,3-cd)pentalen-9-yl 3,4,6-trideoxy-3-(dimethylamino)-β-D-xylo-hexopyranoside.

\* \* \* \* \*